(12) United States Patent
Ivosevic et al.

(10) Patent No.: US 10,022,301 B2
(45) Date of Patent: Jul. 17, 2018

(54) CONNECTION SYSTEM FOR MEDICAL DEVICE COMPONENTS

(71) Applicant: Becton Dickinson and Company Limited, Dun Laoghaire (IE)

(72) Inventors: Milan Ivosevic, Kinnelon, NJ (US); Paul Paia Marici, Piscataway, NJ (US)

(73) Assignee: Becton Dickinson and Company Ltd., Dun Laoghaire (IE)

( * ) Notice: Subject to any disclaimer, the term of this patent is extended or adjusted under 35 U.S.C. 154(b) by 723 days.

(21) Appl. No.: 14/204,468

(22) Filed: Mar. 11, 2014

(65) Prior Publication Data

US 2014/0276649 A1 Sep. 18, 2014

Related U.S. Application Data

(60) Provisional application No. 61/787,674, filed on Mar. 15, 2013, provisional application No. 61/895,168, filed on Oct. 24, 2013, provisional application No. 61/895,182, filed on Oct. 24, 2013, provisional application No. 61/895,187, filed on Oct. 24, 2013.

(51) Int. Cl.
*A61J 1/20* (2006.01)
*A61M 39/12* (2006.01)
*A61M 39/14* (2006.01)
*A61M 39/10* (2006.01)

(52) U.S. Cl.
CPC .......... *A61J 1/2096* (2013.01); *A61J 1/201* (2015.05); *A61J 1/2048* (2015.05); *A61J 1/2082* (2015.05); *A61M 39/12* (2013.01); *A61M 39/14* (2013.01); *A61J 1/2055* (2015.05); *A61J 1/2065* (2015.05); *A61J 1/2072* (2015.05); *A61M 2039/1027* (2013.01); *A61M 2039/1044* (2013.01); *A61M 2039/1072* (2013.01); *Y10T 29/49217* (2015.01)

(58) Field of Classification Search
CPC ........ A61J 1/201; A61J 1/2055; A61J 1/2065; A61J 1/2072; A61J 1/2096; A61J 1/2048; A61J 1/2082; A61M 2039/1027; A61M 2039/1044; A61M 2039/1072; A61M 39/12; A61M 39/14; Y10T 29/49217
See application file for complete search history.

(56) References Cited

U.S. PATENT DOCUMENTS 4,564,054 A 1/1986 Gustavsson
4,673,404 A 6/1987 Gustavsson
(Continued)

FOREIGN PATENT DOCUMENTS

EP 2462971 A1 6/2012
JP 201005461 A 1/2010
(Continued)

*Primary Examiner* — Brandy S Lee
(74) *Attorney, Agent, or Firm* — The Webb Law Firm

(57) ABSTRACT

A connection system for connecting a first medical device component to a second medical device component is disclosed. The connection system of the present disclosure provides for quick and intuitive coupling and decoupling of two opposing medical device components through the use of a connection path and a disconnection path, the connection path being distinct from the disconnection path. Furthermore, the connection system of the present disclosure provides audible and tactile connection feedback through the use of elastically deformable connection elements.

24 Claims, 56 Drawing Sheets

(56) References Cited

U.S. PATENT DOCUMENTS

| | | | |
|---|---|---|---|
| 4,932,937 A | 6/1990 | Gustavsson et al. |
| 5,122,129 A | 6/1992 | Olson et al. |
| 5,280,876 A | 1/1994 | Atkins |
| 5,290,254 A | 3/1994 | Vaillancourt |
| 5,334,188 A | 8/1994 | Inoue et al. |
| 5,360,011 A | 11/1994 | McCallister |
| 5,395,348 A | 3/1995 | Ryan |
| 5,437,650 A | 8/1995 | Larkin et al. |
| 5,464,123 A | 11/1995 | Scarrow |
| 5,472,430 A | 12/1995 | Vaillancourt et al. |
| 5,478,328 A | 12/1995 | Silverman et al. |
| 5,487,728 A | 1/1996 | Vaillancourt |
| 5,507,733 A | 4/1996 | Larkin et al. |
| 5,509,911 A | 4/1996 | Cottone, Sr. et al. |
| 5,545,152 A | 8/1996 | Funderburk et al. |
| 5,607,392 A | 3/1997 | Kanner |
| 5,609,584 A | 3/1997 | Gettig et al. |
| 5,611,792 A | 3/1997 | Gustafsson |
| 5,647,845 A | 7/1997 | Haber et al. |
| 5,685,866 A | 11/1997 | Lopez |
| 5,807,347 A | 9/1998 | Bonaldo |
| 5,897,526 A | 4/1999 | Vaillancourt |
| 6,063,068 A | 5/2000 | Fowles et al. |
| 6,089,541 A | 7/2000 | Weinheimer et al. |
| 6,113,583 A | 9/2000 | Fowles et al. |
| 6,132,404 A | 10/2000 | Lopez |
| 6,139,534 A | 10/2000 | Niedospial, Jr. et al. |
| 6,221,041 B1 | 4/2001 | Russo |
| 6,221,056 B1 | 4/2001 | Silverman |
| 6,343,629 B1 | 2/2002 | Wessman et al. |
| 6,358,236 B1 | 3/2002 | DeFoggi et al. |
| 6,409,708 B1 | 6/2002 | Wessman |
| 6,474,375 B2 | 11/2002 | Spero et al. |
| 6,478,788 B1 | 11/2002 | Aneas |
| 6,544,246 B1 | 4/2003 | Niedospial, Jr. |
| 6,551,299 B2 | 4/2003 | Miyoshi et al. |
| 6,585,695 B1 | 7/2003 | Adair et al. |
| 6,599,273 B1 | 7/2003 | Lopez |
| 6,610,040 B1 | 8/2003 | Fowles et al. |
| 6,629,958 B1 | 10/2003 | Spinello |
| 6,656,433 B2 | 12/2003 | Sasso |
| 6,715,520 B2 | 4/2004 | Andreasson et al. |
| 6,814,726 B1 | 11/2004 | Lauer |
| 6,852,103 B2 | 2/2005 | Fowles et al. |
| 6,875,203 B1 | 4/2005 | Fowles et al. |
| 6,875,205 B2 | 4/2005 | Leinsing |
| 6,911,025 B2 | 6/2005 | Miyahara |
| 6,997,917 B2 | 2/2006 | Niedospial, Jr. et al. |
| 7,040,598 B2 | 5/2006 | Raybuck |
| 7,083,605 B2 | 8/2006 | Miyahara |
| 7,097,209 B2 | 8/2006 | Unger et al. |
| 7,261,707 B2 | 8/2007 | Frezza et al. |
| 7,306,584 B2 | 12/2007 | Wessman et al. |
| 7,326,194 B2 | 2/2008 | Zinger et al. |
| 7,350,535 B2 | 4/2008 | Liepold et al. |
| 7,354,427 B2 | 4/2008 | Fangrow |
| 7,452,349 B2 | 11/2008 | Miyahara |
| 7,547,300 B2 | 6/2009 | Fangrow |
| 7,628,772 B2 | 12/2009 | McConnell et al. |
| 7,648,491 B2 | 1/2010 | Rogers |
| 7,658,734 B2 | 2/2010 | Adair et al. |
| 7,743,799 B2 | 6/2010 | Mosler et al. |
| 7,744,581 B2 | 6/2010 | Wallen et al. |
| 7,758,560 B2 | 7/2010 | Connell et al. |
| 7,803,140 B2 | 9/2010 | Fangrow, Jr. |
| 7,867,215 B2 | 1/2011 | Akerlund et al. |
| 7,879,018 B2 | 2/2011 | Zinger et al. |
| 7,900,659 B2 | 3/2011 | Whitley et al. |
| 7,927,316 B2 | 4/2011 | Proulx et al. |
| 7,942,860 B2 | 5/2011 | Horppu |
| 7,975,733 B2 | 7/2011 | Horppu et al. |
| 8,096,525 B2 | 1/2012 | Ryan |
| 8,122,923 B2 | 2/2012 | Kraus et al. |
| 8,123,738 B2 | 2/2012 | Vaillancourt |
| 8,137,332 B2 | 3/2012 | Pipelka |
| 8,167,863 B2 | 5/2012 | Yow |
| 8,177,768 B2 | 5/2012 | Leinsing |
| 8,196,614 B2 | 6/2012 | Kriheli |
| 8,206,367 B2 | 6/2012 | Warren et al. |
| 8,211,069 B2 | 7/2012 | Fangrow, Jr. |
| 8,226,628 B2 | 7/2012 | Muramatsu et al. |
| 8,257,286 B2 | 9/2012 | Meyer et al. |
| 8,267,127 B2 | 9/2012 | Kriheli |
| 8,277,424 B2 | 10/2012 | Pan |
| 8,317,741 B2 | 11/2012 | Kraushaar |
| 8,317,743 B2 | 11/2012 | Denenburg |
| 8,398,607 B2 | 3/2013 | Fangrow, Jr. |
| 8,403,905 B2 | 3/2013 | Yow |
| 8,425,487 B2 | 4/2013 | Beiriger et al. |
| 8,449,521 B2 | 5/2013 | Thorne, Jr. et al. |
| 8,454,579 B2 | 6/2013 | Fangrow, Jr. |
| 2003/0070726 A1 | 4/2003 | Andreasson et al. |
| 2004/0141886 A1 | 7/2004 | Py et al. |
| 2005/0065495 A1 | 3/2005 | Zambaux |
| 2005/0182383 A1 | 8/2005 | Wallen |
| 2005/0215976 A1 | 9/2005 | Wallen |
| 2006/0118749 A1 | 6/2006 | Ryan et al. |
| 2007/0079894 A1 | 4/2007 | Kraus et al. |
| 2008/0045919 A1 | 2/2008 | Jakob et al. |
| 2008/0287914 A1 | 11/2008 | Wyatt et al. |
| 2009/0159485 A1 | 6/2009 | Jakob et al. |
| 2010/0179506 A1 | 7/2010 | Shemesh et al. |
| 2010/0217226 A1 | 8/2010 | Shemesh |
| 2010/0241088 A1 | 9/2010 | Ranalletta et al. |
| 2011/0004183 A1 | 1/2011 | Carrez et al. |
| 2011/0062703 A1 | 3/2011 | Lopez et al. |
| 2011/0074148 A1 | 3/2011 | Imai |
| 2011/0106046 A1 | 5/2011 | Hiranuma et al. |
| 2011/0125128 A1* | 5/2011 | Nord ............... A61J 1/2096 604/414 |
| 2011/0257621 A1 | 10/2011 | Fangrow |
| 2011/0291406 A1 | 12/2011 | Kraft et al. |
| 2012/0035580 A1 | 2/2012 | Fangrow |
| 2012/0046636 A1 | 2/2012 | Kriheli |
| 2012/0123381 A1 | 5/2012 | Kraus et al. |
| 2012/0192968 A1 | 8/2012 | Bonnal et al. |
| 2012/0192976 A1 | 8/2012 | Rahimy et al. |
| 2012/0203193 A1 | 8/2012 | Rogers |
| 2012/0265163 A1 | 10/2012 | Cheng et al. |
| 2012/0279884 A1 | 11/2012 | Tennican et al. |
| 2012/0316536 A1 | 12/2012 | Carrez et al. |
| 2013/0006211 A1 | 1/2013 | Takemoto |
| 2013/0012908 A1 | 1/2013 | Yeung |
| 2013/0066293 A1 | 3/2013 | Garfield et al. |
| 2013/0072893 A1 | 3/2013 | Takemoto |
| 2013/0076019 A1 | 3/2013 | Takemoto |
| 2013/0079744 A1 | 3/2013 | Okiyama et al. |

FOREIGN PATENT DOCUMENTS

| | | |
|---|---|---|
| JP | 2012520742 A | 9/2012 |
| WO | 2005011781 A1 | 2/2005 |
| WO | 2006103074 A1 | 10/2006 |
| WO | 2009024807 A1 | 2/2009 |
| WO | 2009090627 A1 | 7/2009 |
| WO | 2011050333 A1 | 4/2011 |
| WO | 2012069401 A1 | 5/2012 |
| WO | 2012119225 A1 | 9/2012 |
| WO | 2012168235 A1 | 12/2012 |
| WO | 2013025946 A1 | 2/2013 |
| WO | 2013054323 A1 | 4/2013 |
| WO | 2013066779 A1 | 5/2013 |
| WO | 2013115730 A1 | 8/2013 |
| WO | 2013179596 A1 | 12/2013 |

* cited by examiner

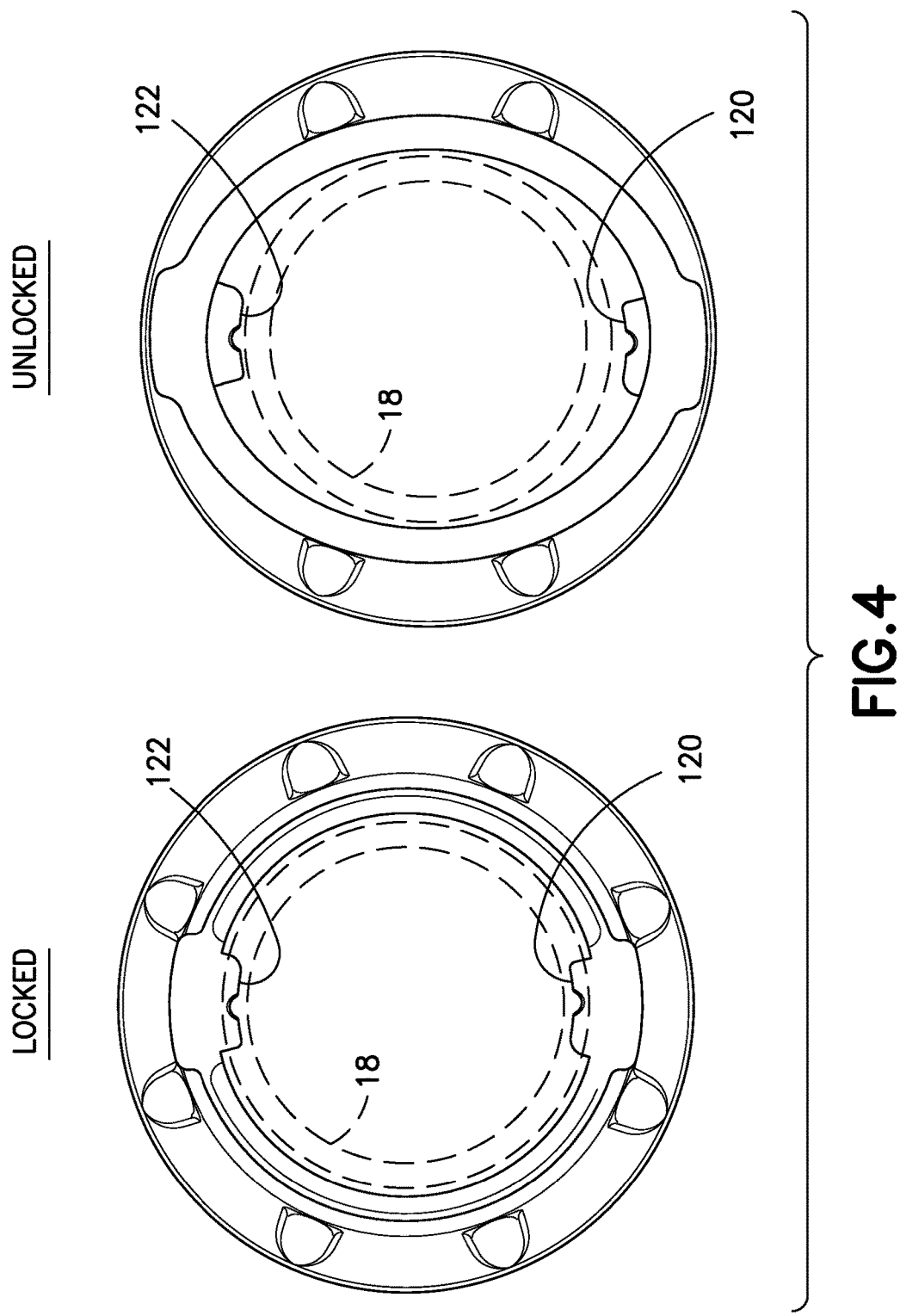

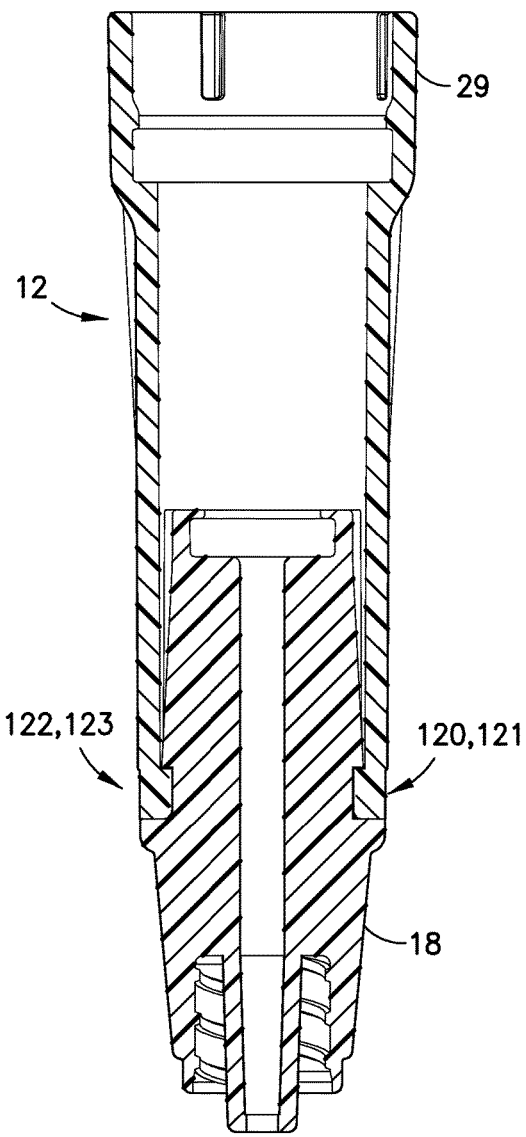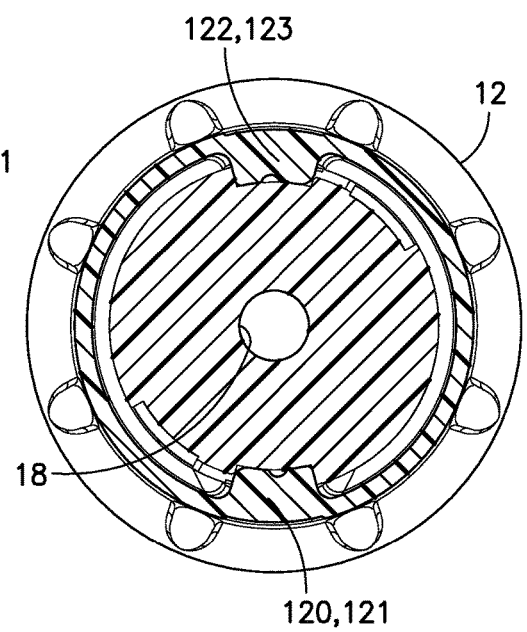
FIG.5B
FIG.5C

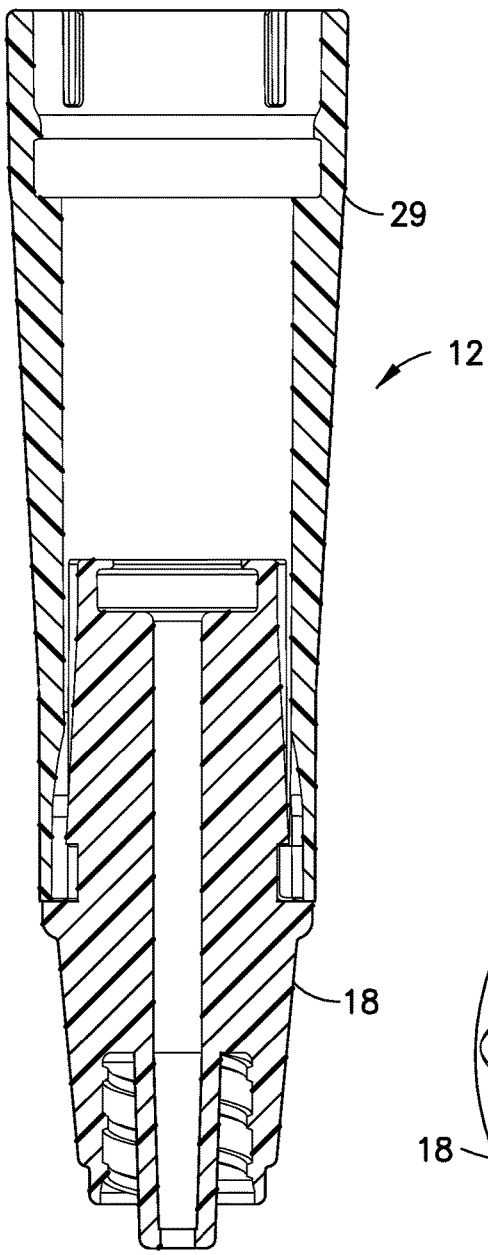
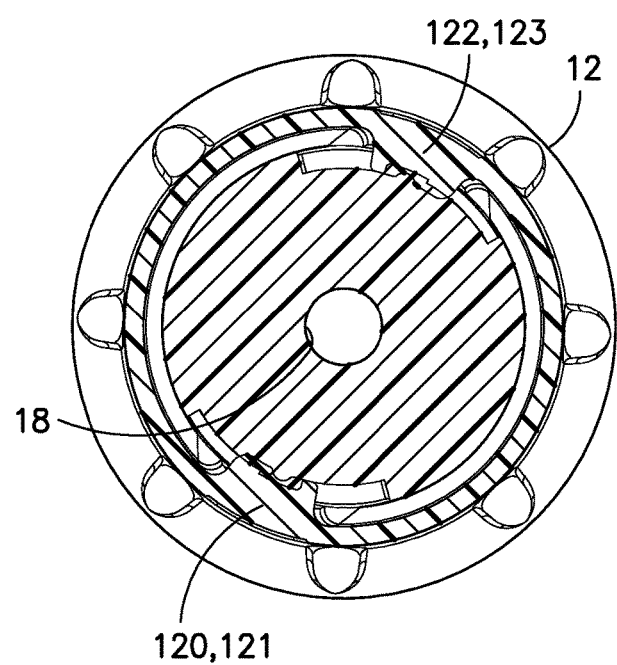
FIG.6B
FIG.6C

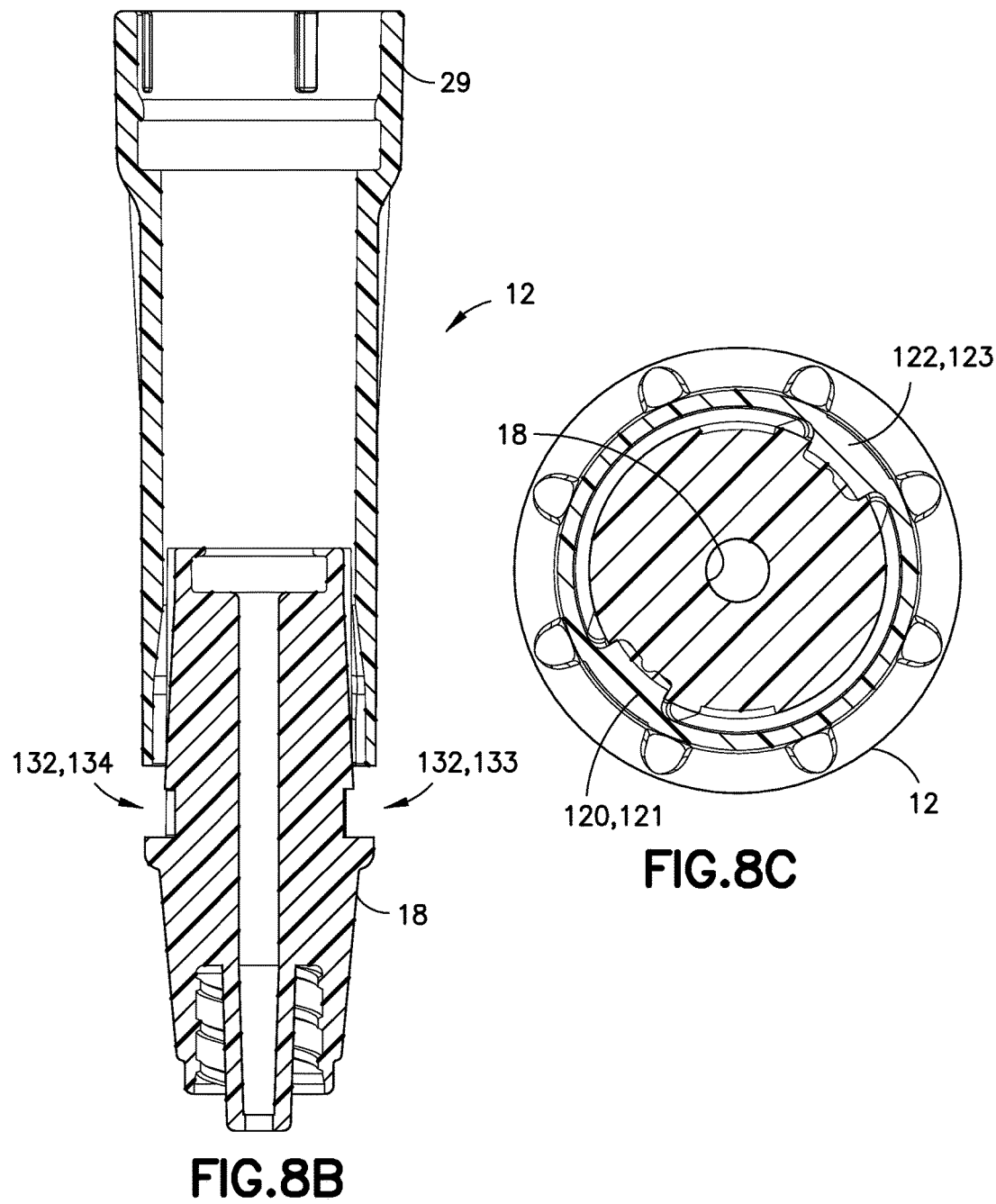

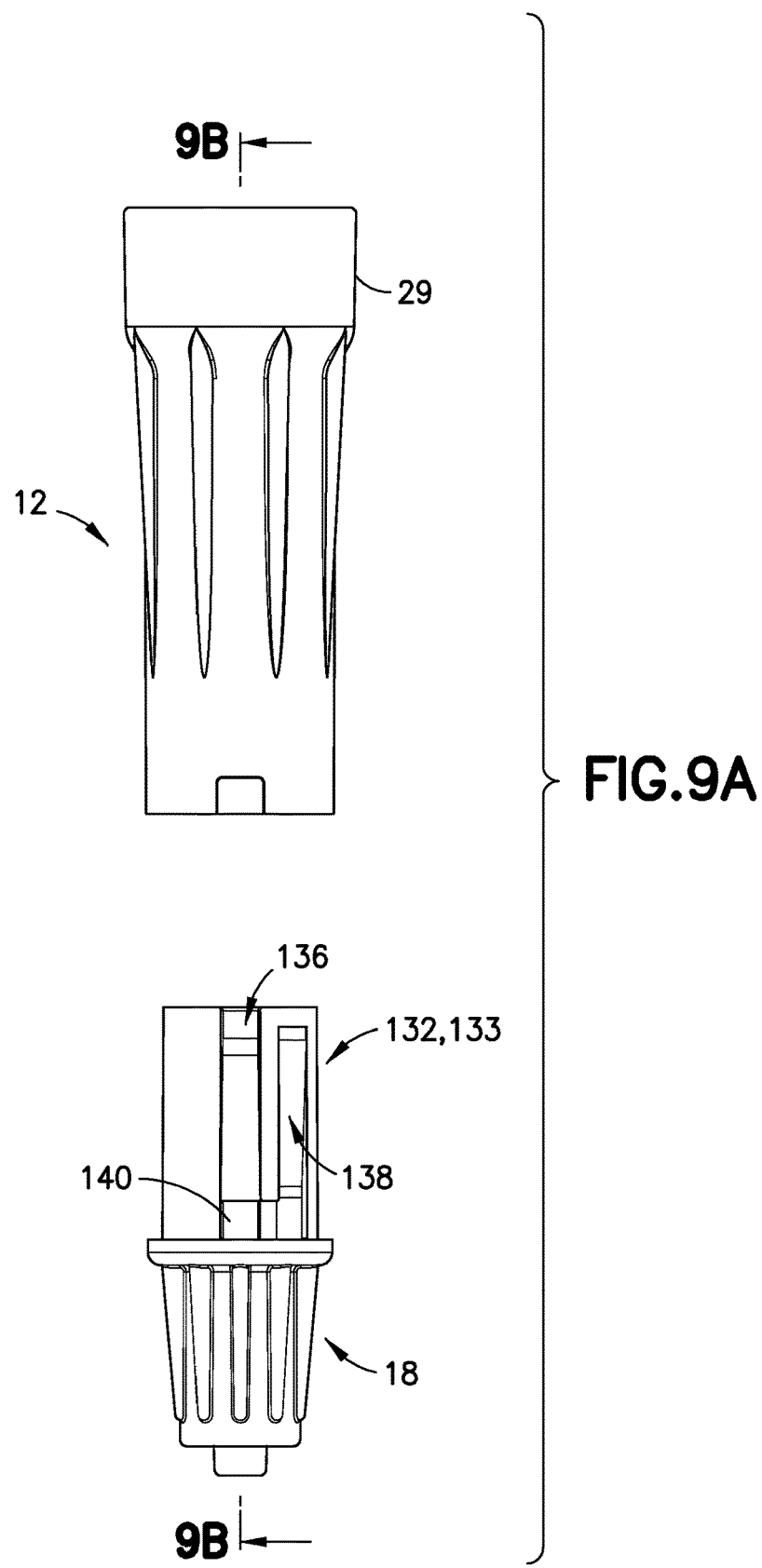

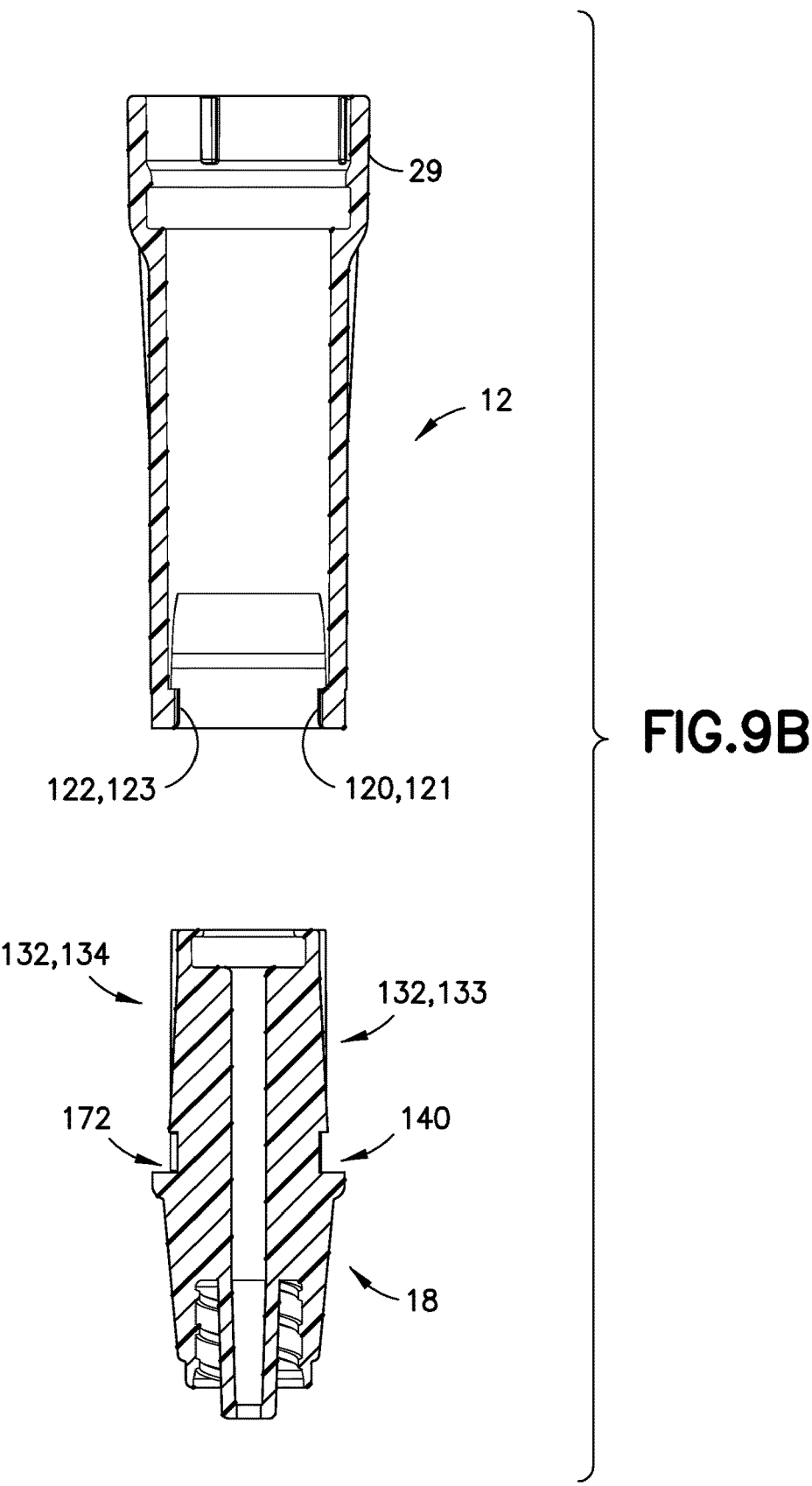

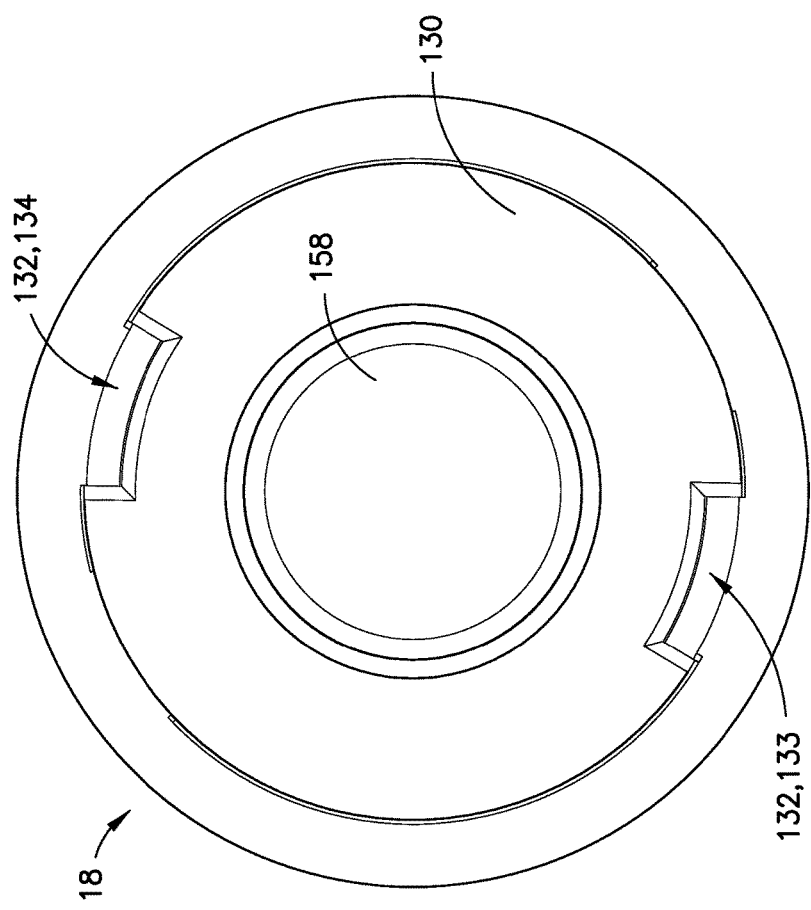

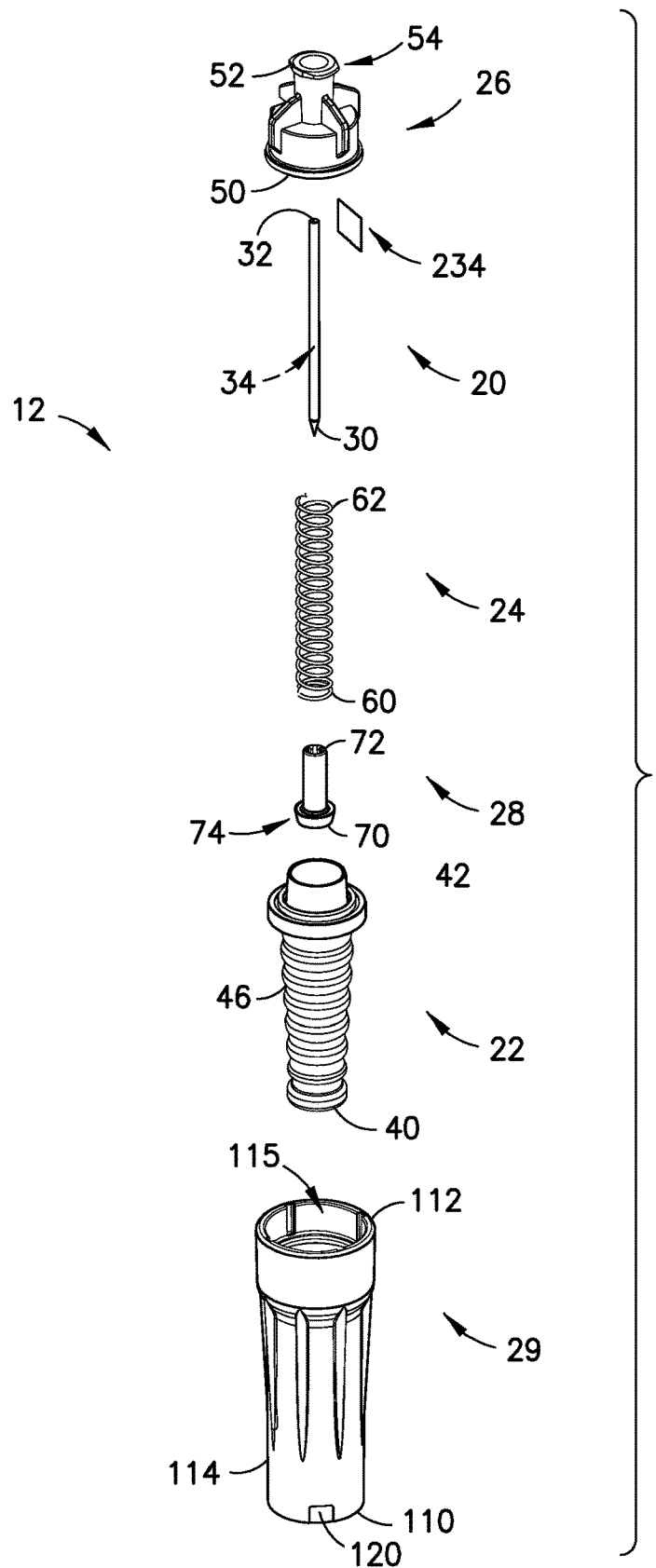

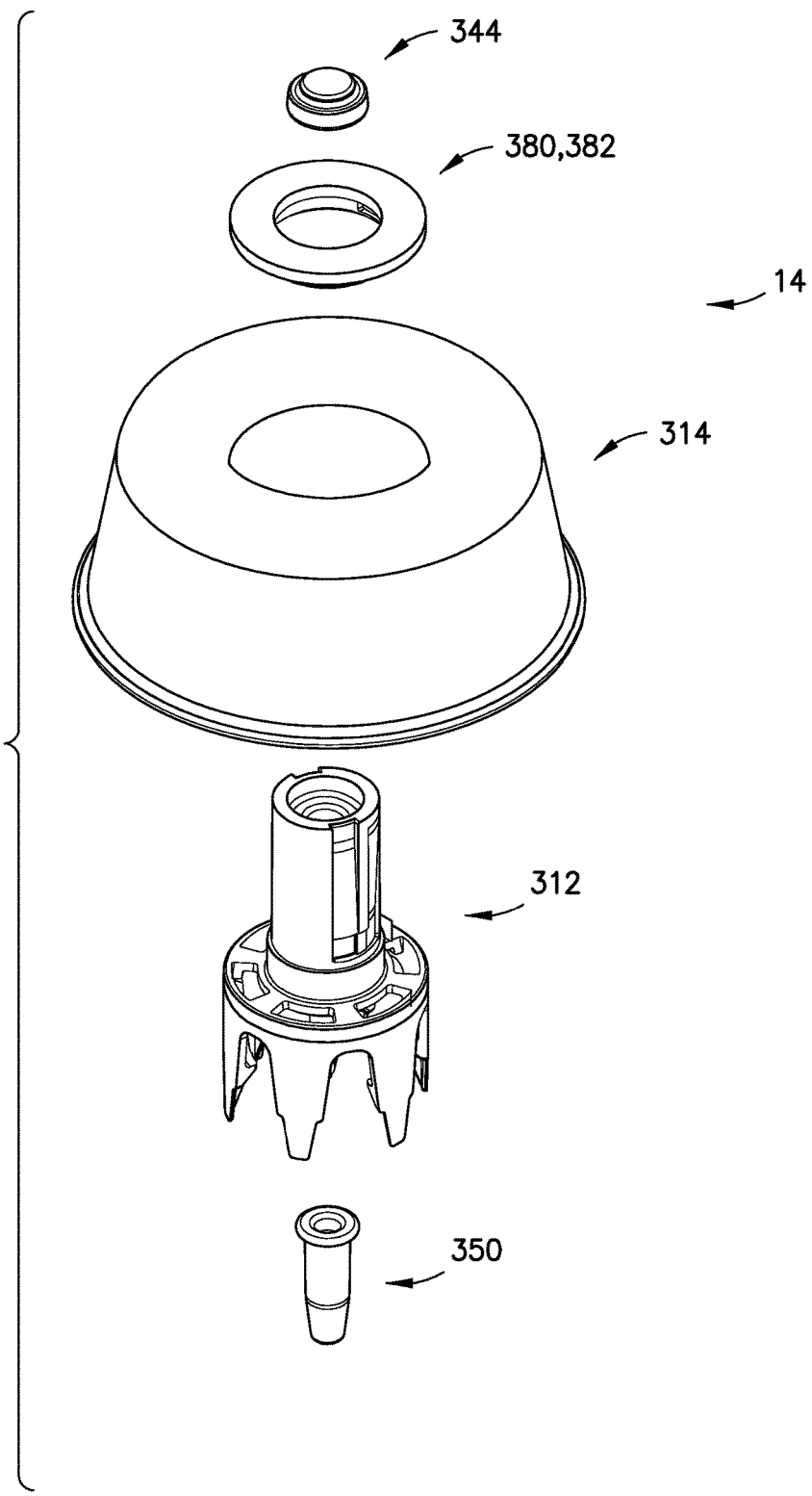

CONNECTION SYSTEM FOR MEDICAL DEVICE COMPONENTS

CROSS-REFERENCE TO RELATED APPLICATION

This application claims priority to U.S. Provisional Application No. 61/787,674, filed Mar. 15, 2013, and to U.S. Provisional Application Nos. 61/895,168, 61/895,182, and 61/895,187, which were each filed on Oct. 24, 2013. The disclosures of the provisional patent applications mentioned above are each hereby incorporated by reference in its entirety.

BACKGROUND OF THE INVENTION

1. Field of the Disclosure

The present disclosure relates generally to a connection system. More particularly, the present disclosure relates to a connection system for a first medical device component and a second medical device component.

2. Description of the Related Art

Some medical components, such as intravenous line connectors, require connection to other components, such as to intravenous lines or to syringe adapter or injector assemblies. Typical connection systems for medical device components include a single path for connection and disconnection. Such connection systems involve reverse movements in the same path for connection and disconnection. There is a need for a connection system for medical device components that is intuitive to connect and disconnect while minimizing the risk of inadvertent disconnection.

SUMMARY OF THE INVENTION

The present disclosure provides a connection system for connecting a first medical device component to a second medical device component. The connection system of the present disclosure provides for quick and intuitive coupling and decoupling of two opposing medical device components through the use of a connection path and a disconnection path, the connection path being distinct from the disconnection path. Furthermore, the connection system of the present disclosure provides audible and tactile connection feedback through the use of elastically deformable connection elements.

In accordance with an embodiment of the present invention, a system includes a first medical device component having a first end, a second end, and a sidewall extending therebetween, the sidewall having an exterior surface and an interior surface, the interior surface of the sidewall having a first projecting element; and a second medical device component having a first connection channel, a first disconnection channel, and a first securement element disposed between the first connection channel and the first disconnection channel, the first connection channel distinct from the first disconnection channel, wherein with the first projecting element of the first medical device component received within the first connection channel of the second medical device component, the first connection channel guides the first projecting element to the first securement element, wherein with the first projecting element engaged with the first securement element, the first medical device component is secured to the second medical device component, and wherein with the first projecting element of the first medical device component received within the first disconnection channel of the second medical device component, the first disconnection channel guides the first projecting element out from the first disconnection channel thereby disengaging the first medical device component from the second medical device component In one configuration, the first medical device component is an injector adapter and the second medical device component is a vial adapter. In another configuration, the first medical device component is an injector adapter and the second medical device component is an IV line adapter. In yet another configuration, the interior surface of the sidewall of the first medical device component includes a second projecting element spaced from the first projecting element. In one configuration, the second medical device component further includes a second connection channel, a second disconnection channel, and a second securement element disposed between the second connection channel and the second disconnection channel, the second connection channel distinct from the second disconnection channel. In another configuration, with the second projecting element of the first medical device component received within the second connection channel of the second medical device component, the second connection channel guides the second projecting element to the second securement element, wherein with the second projecting element engaged with the second securement element, the first medical device component is secured to the second medical device component, and wherein with the second projecting element of the first medical device component received within the second disconnection channel of the second medical device component, the second disconnection channel guides the second projecting element out from the second disconnection channel thereby disengaging the first medical device component from the second medical device component. In yet another configuration, the second medical device component further includes a first step member disposed between the first securement element and the first disconnection channel and a second step member disposed between the second securement element and the second disconnection channel. In one configuration, with the first projecting element engaged with the first securement element, rotation of the first medical device component in a counter-clockwise direction relative to the second medical device component disengages the first projection element from the first securement element and moves the first projection element over the first step member and into the first disconnection channel. In another configuration, with the second projecting element engaged with the second securement element, rotation of the first medical device component in a counter-clockwise direction relative to the second medical device component disengages the second projection element from the second securement element and moves the second projection element over the second step member and into the second disconnection channel. In yet another configuration, with the first projecting element engaged with the first securement element, rotation of the first medical device component in a clockwise direction relative to the second medical device component disengages the first projection element from the first securement element and moves the first projection element over the first step member and into the first disconnection channel. In another configuration, with the second projecting element engaged with the second securement element, rotation of the first medical device component in a clockwise direction relative to the second medical device component disengages the second projection element from the second securement element and moves the second projection element over the second step member and into the second disconnection channel. In yet another configuration, the first projecting element includes an elastically deformable tab. In one configuration, the first securement element includes a recess.

In accordance with another embodiment of the present invention, a system includes an injector adapter enclosing a cannula, the injector adapter having a first end, a second end, and a sidewall extending therebetween, the sidewall having an exterior surface and an interior surface, the interior surface of the sidewall having a first projecting element; and a vial adapter attachable to a vial, the vial adapter having a vial seal, a first connection channel, a first disconnection channel, and a first securement element disposed between the first connection channel and the first disconnection channel, the first connection channel distinct from the first disconnection channel, wherein with the first projecting element of the injector adapter received within the first connection channel of the vial adapter, the first connection channel guides the first projecting element to the first securement element, wherein with the first projecting element engaged with the first securement element, the injector adapter is secured to the vial adapter, and wherein with the first projecting element of the injector adapter received within the first disconnection channel of the vial adapter, the first disconnection channel guides the first projecting element out from the first disconnection channel thereby disengaging the injector adapter from the vial adapter.

In one configuration, the interior surface of the sidewall of the injector adapter includes a second projecting element spaced from the first projecting element. In another configuration, the vial adapter further includes a second connection channel, a second disconnection channel, and a second securement element disposed between the second connection channel and the second disconnection channel, the second connection channel distinct from the second disconnection channel. In yet another configuration, with the second projecting element of the injector adapter received within the second connection channel of the vial adapter, the second connection channel guides the second projecting element to the second securement element, wherein with the second projecting element engaged with the second securement element, the injector adapter is secured to the vial adapter, and wherein with the second projecting element of the injector adapter received within the second disconnection channel of the vial adapter, the second disconnection channel guides the second projecting element out from the second disconnection channel thereby disengaging the injector adapter from the vial adapter. In one configuration, the vial adapter further includes a first step member disposed between the first securement element and the first disconnection channel and a second step member disposed between the second securement element and the second disconnection channel. In another configuration, with the first projecting element engaged with the first securement element, rotation of the injector adapter in a counter-clockwise direction relative to the vial adapter disengages the first projection element from the first securement element and moves the first projection element over the first step member and into the first disconnection channel. In yet another configuration, with the second projecting element engaged with the second securement element, rotation of the injector adapter in a counter-clockwise direction relative to the vial adapter disengages the second projection element from the second securement element and moves the second projection element over the second step member and into the second disconnection channel. In another configuration, with the first projecting element engaged with the first securement element, rotation of the injector adapter in a clockwise direction relative to the vial adapter disengages the first projection element from the first securement element and moves the first projection element over the first step member and into the first disconnection channel. In yet another configuration, with the second projecting element engaged with the second securement element, rotation of the injector adapter in a clockwise direction relative to the vial adapter disengages the second projection element from the second securement element and moves the second projection element over the second step member and into the second disconnection channel. In one configuration, the first projecting element includes an elastically deformable tab. In another configuration, the second projecting element includes an elastically deformable tab. In yet another configuration, the first securement element includes a recess. In one configuration, the second securement element includes a recess.

In a further embodiment, a membrane for a medical connector includes a body having a first end and a second end with a sidewall extending between the first end and the second end, the sidewall of the body defining an annular recess, the second end of the body defining a cavity that extends toward the first end of the body, and the annular recess configured to receive a portion of a medical connector.

The first end of the body may include a convex surface. The cavity of the body may have a first end and terminate at a second end with the second end positioned at least about half a length of the body from the first end of the cavity. The second end of the cavity may define a concave surface. The cavity may be wider at the first end of the cavity than at the second end of the cavity. An annular projection may extend from the second end of the body. An inside corner defining the annular recess may be radiused.

In another embodiment, a medical connector includes a connector body defining an interior space, and a membrane body having a first end and a second end with a sidewall extending between the first end and the second end of the membrane body. The second end of the membrane body defining a cavity that extends toward the first end of the body, where the membrane body is secured to the connector body via an interference fit, and where a portion of the membrane body is received within the interior space of the connector body.

The sidewall of the membrane body may define an annular recess and the connector body may include a projection extending into the interior space of the connector body, with the projection of the connector body received within the annular recess of the membrane body. The sidewall and the annular recess of the membrane body may establish the interference fit with the connector body. The first end of the membrane body may extend beyond the connector body. The first end of the membrane body may include a convex surface.

In yet another embodiment, a method of assembling a medical connector includes: providing a connector body defining an interior space; positioning a membrane adjacent to the connector body with the membrane comprising a membrane body having a first end and a second end with a sidewall extending between the first end and the second end of the membrane body, and the second end of the membrane body defining a cavity that extends toward the first end of the body; and inserting a portion of the membrane body within the interior space of the connector body and elastically deforming the membrane body to secure the membrane to the connector body via an interference fit.

The method may include: positioning an assembly tool on a first end of the connector body adjacent to the interior space, the assembly tool having a conical surface; and elastically deforming the membrane body prior to inserting the portion of the membrane body within the interior space of the connector body by engaging the conical surface of the assembly tool with the portion of the membrane body. The sidewall of the membrane body may define an annular recess and the connector body may include a projection extending into the interior space of the connector body, with the method further including positioning the projection of the connector body within the annular recess of the membrane body.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 4 is a front elevation view of a first medical device component and a second medical device component including a connection system of the present disclosure illustrating an elastically deformable portion in accordance with an embodiment of the present invention.

FIG. 5B is a cross-sectional view of the system of FIG. 5A taken along line 5B-5B of FIG. 5A in accordance with an embodiment of the present invention.

FIG. 5C is a cross-sectional view of the system of FIG. 5A taken along line 5C-5C of FIG. 5A in accordance with an embodiment of the present invention.

FIG. 6B is a cross-sectional view of the system of FIG. 6A taken along line 6B-6B of FIG. 6A in accordance with an embodiment of the present invention.

FIG. 6C is a cross-sectional view of the system of FIG. 6A taken along line 6C-6C of FIG. 6A in accordance with an embodiment of the present invention.

FIG. 8B is a cross-sectional view of the system of FIG. 8A in accordance with an embodiment of the present invention.

FIG. 8C is a cross-sectional view of the system of FIG. 8A taken along line 8C-8C of FIG. 8A in accordance with an embodiment of the present invention.

FIG. 9A is an exploded, perspective view of a first medical device component and a second medical device component in accordance with an embodiment of the present invention.

FIG. 9B is a cross-sectional view of the system of FIG. 9A taken along line 9B-9B of FIG. 9A in accordance with an embodiment of the present invention.

FIG. 12B is a top view of an intravenous line adapter in accordance with an embodiment of the present invention.

FIG. 15 is an exploded, perspective view of an injector adapter in accordance with an embodiment of the present invention.

FIG. 19A is an exploded, perspective view of a vial adapter in accordance with an embodiment of the present invention.

DETAILED DESCRIPTION

Figure 1:
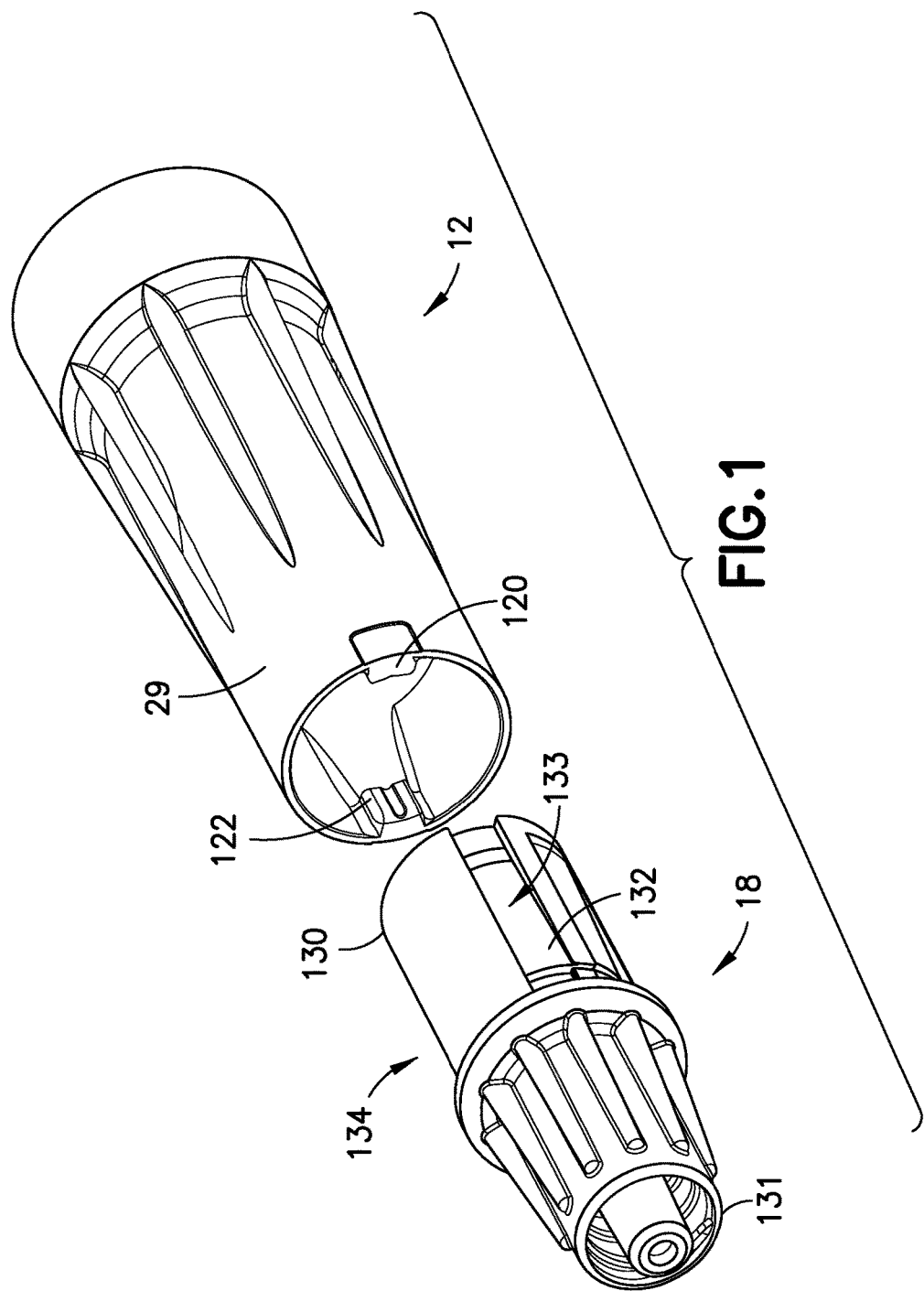
FIG. 1 is an exploded, perspective view of a first medical device component and a second medical device component including a connection system in accordance with an embodiment of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 11A:
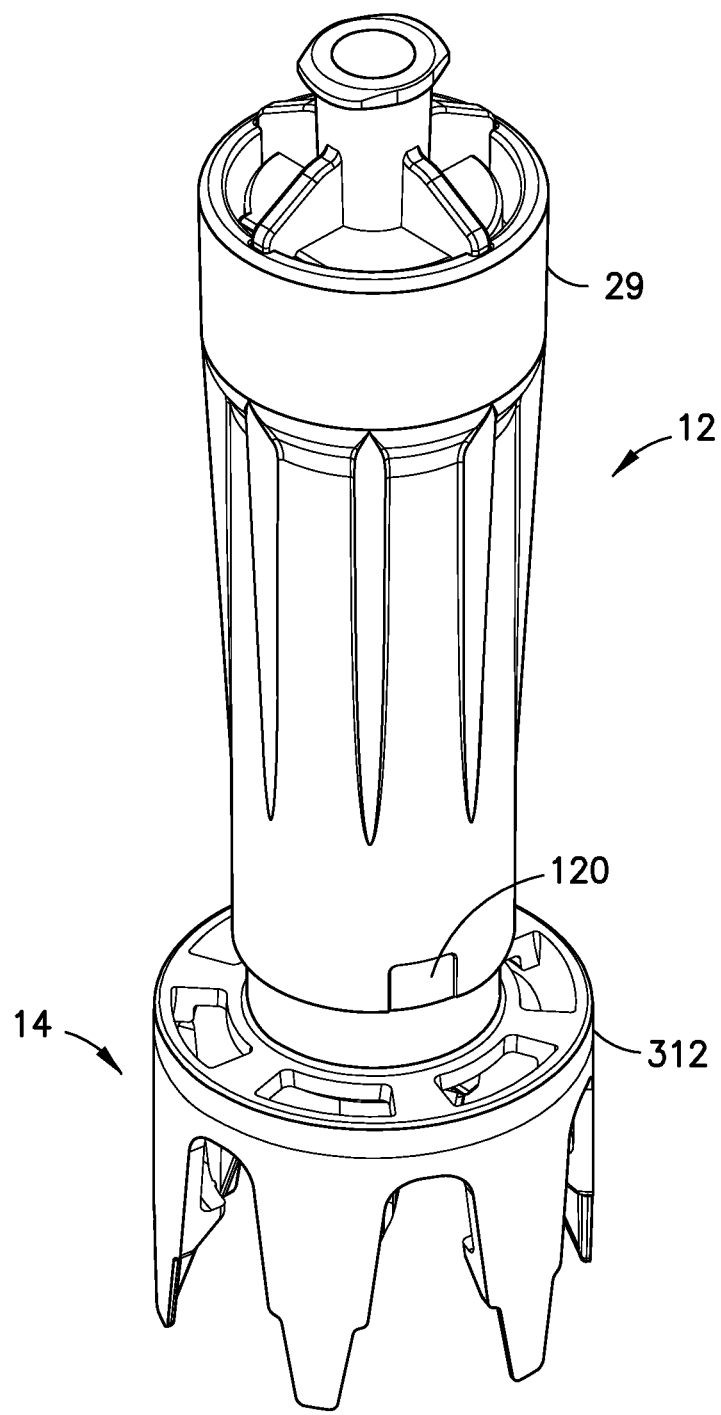
FIG. 11A is a perspective view of a first medical device component connected to a second medical device component by a connection system in accordance with another embodiment of the present invention.

The present disclosure provides a connection system for connecting a first medical device component to a second medical device component. FIG. 1 illustrates the connection system of the present disclosure connecting the housing of an injector adapter to an intravenous line adapter according to an exemplary embodiment of the present disclosure. FIG. 11A illustrates the connection system of the present disclosure connecting the housing of an injector adapter to a vial adapter according to another exemplary embodiment of the present disclosure. Furthermore, the connection system of the present disclosure may be used to connect other medical device components.

Figure 24:
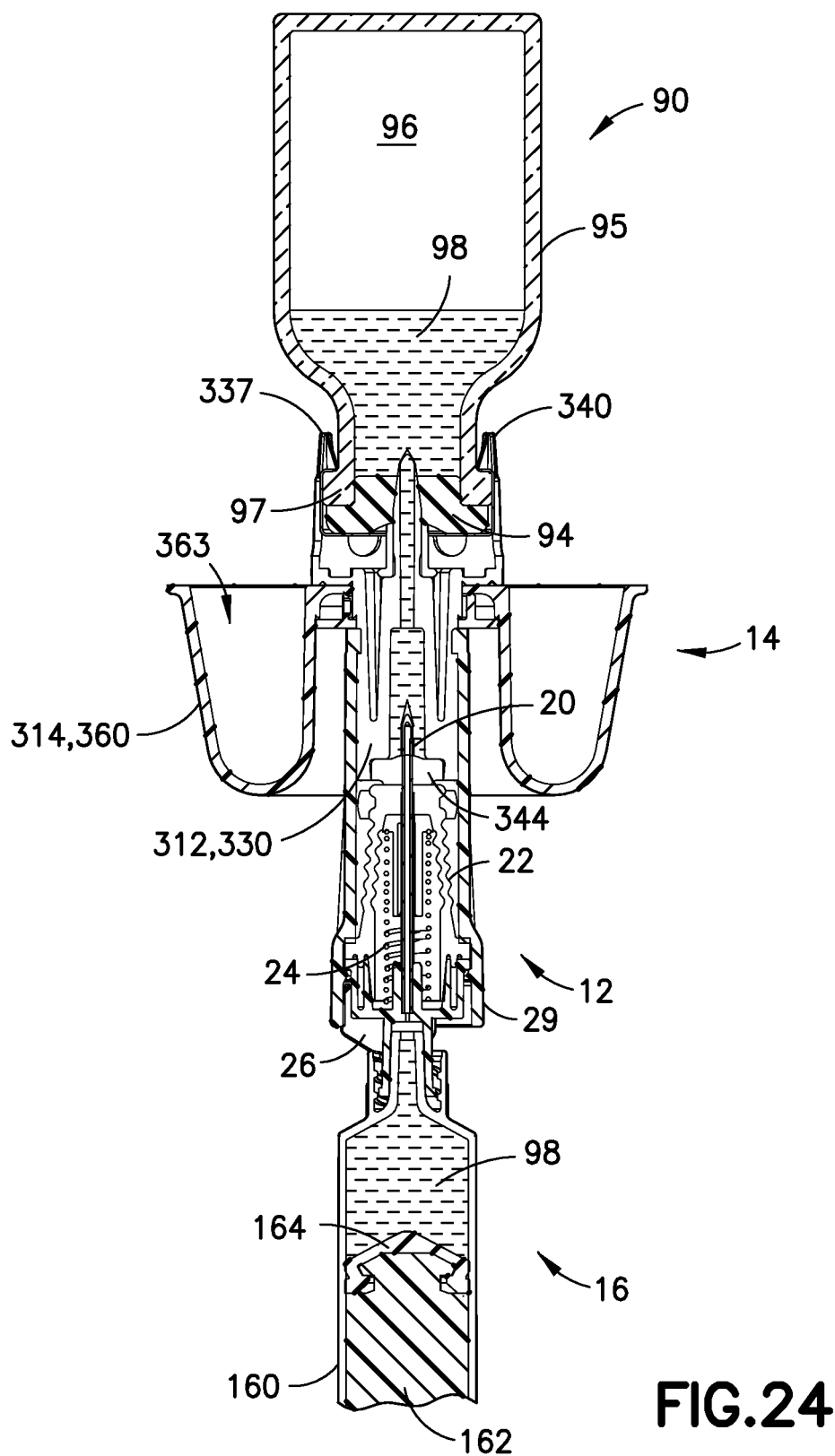
FIG. 24 is a cross-sectional view of the system of FIG. 22 with the system inverted and a cannula seal in communication with a vial seal and a cannula in fluid communication with a substance contained within a vial chamber in accordance with an embodiment of the present invention.

Referring to FIGS. 15-18, injector adapter 12 generally includes a cannula 20, a cannula seal 22, a spring 24, a needle hub 26, a cannula stabilizing member 28, a housing 29, a gliding ring 31, a one-way valve 232, and a filter 234. Referring to FIG. 15, cannula 20 includes a distal end 30, a proximal end 32, and a lumen 34 extending therebetween. Distal end 30 is in fluid communication with proximal end 32 via lumen 34 of cannula 20. As shown in FIG. 24, distal end 30 of cannula 20 is capable of piercing cannula seal 22 and a vial seal membrane 344 to place a vial chamber 96 in fluid communication with a barrel chamber 176 via cannula 20. In one embodiment, distal end 30 of cannula 20 defines a sharp point.

Injector adapter 12 is compatible with a system for the closed transfer of fluids that provides substantially leak-proof sealing and pressure balancing during engagement of a cannula with a vial, during transfer of a substance from a vial chamber to a barrel chamber via the cannula, and during disengagement of the cannula from the vial. Such a leak-proof sealing of the system substantially prevents leakage of both air and liquid during use of the system. The system is compatible with a needle and syringe assembly for accessing a medication contained within a vial for administering the medication to a patient. The system is also compatible to be used with a drug reconstitution system.

Figure 25:
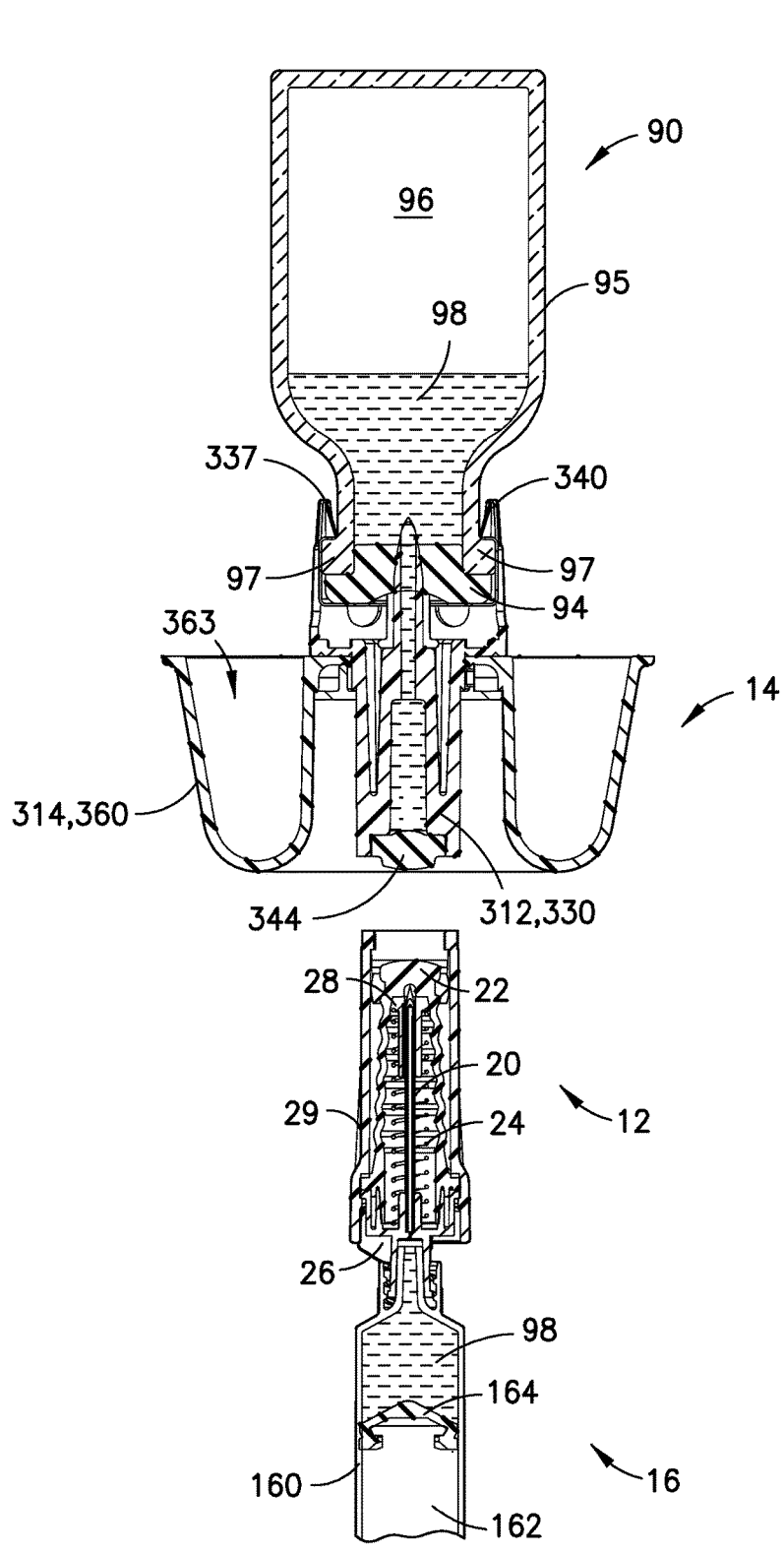
FIG. 25 is a cross-sectional view of the system of FIG. 22 with the system inverted and a cannula seal not in communication with a vial seal and a portion of a substance contained within a vial chamber transferred to a barrel chamber via a cannula in accordance with an embodiment of the present invention.
Figure 26:
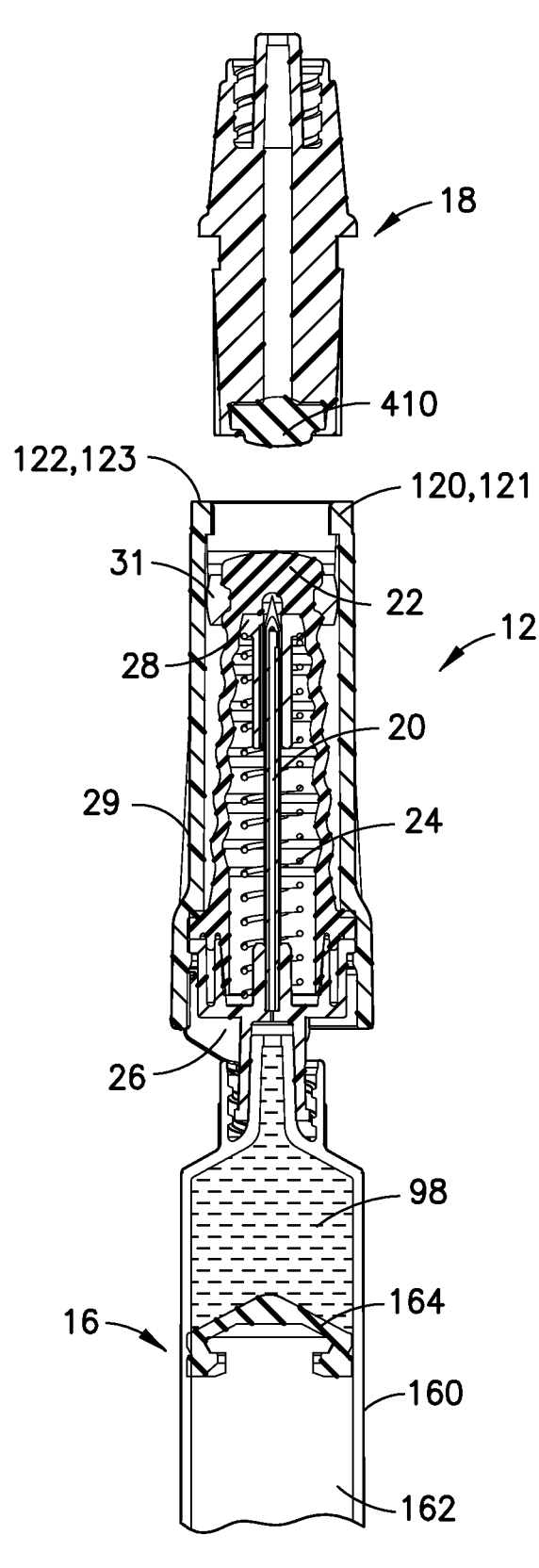
FIG. 26 is a cross-sectional view of the system of FIG. 25 with a portion of a substance contained within a vial chamber transferred to a barrel chamber via a cannula and the injector adapter positioned adjacent an intravenous line adapter in accordance with an embodiment of the present invention.

Referring to FIGS. 15-18, cannula seal 22 generally includes a self-sealing seal secured over cannula 20 so that cannula seal 22 encloses cannula 20 in a sealed position (FIG. 25) to provide a substantially leak-proof seal preventing any liquid, air, or medication residue from being exposed to a health care provider transferring, reconstituting, transporting, or administering a drug using injector adapter 12. Referring to FIG. 25, with cannula seal 22 in the sealed position, cannula seal 22 encloses cannula 20 to also prevent accidental needle stick injuries to a user of injector adapter 12. Cannula seal 22 includes a distal end 40, a proximal end 42, annular ribbed members 46 extending therebetween, and a shoulder portion 44 (FIG. 16) located on an interior wall 48 near distal end 40 of cannula seal 22. In one embodiment, distal end 40 of cannula seal 22 includes an annular cavity 41. The distal end 40 of cannula seal 22 defines a convex surface and has a transverse cross-sectional shape that is generally circular, although it is contemplated that other shapes and sizes of distal end 40 may be used. For example, distal end 40 of cannula seal 22 can have other multi-sided polygon cross-sectional shapes, such as square or oval cross-sectional shapes. The cannula seal 22 may have a length that is about equal to a length of the cannula 20 and, upon assembly of the injector adapter 12, the cannula seal 22 may extend about the entire length of the cannula 20.

In one embodiment, cannula seal 22 comprises a resilient material. For example, cannula seal 22 is preferably a unitary device molded of any flexible, elastomeric material conventionally used for fabricating gas-proof closures. Cannula seal 22 may be formed of a natural rubber material, polyurethane elastomers, butyl rubbers, or similar materials. It is contemplated that cannula seal 22 is formed of a material having a Shore A hardness of approximately 10 to 50. It is also envisioned that cannula seal 22 can have other material hardness values that would provide an appropriate self-sealing material to provide a substantially leak-proof seal with cannula seal 22 in the sealed position, thereby preventing any liquid or medication residue from being exposed to a health care provider transferring, reconstituting, transporting, or administering a drug using injector adapter 12. In one embodiment, cannula seal 22 comprises a resilient sleeve.

Figure 16:
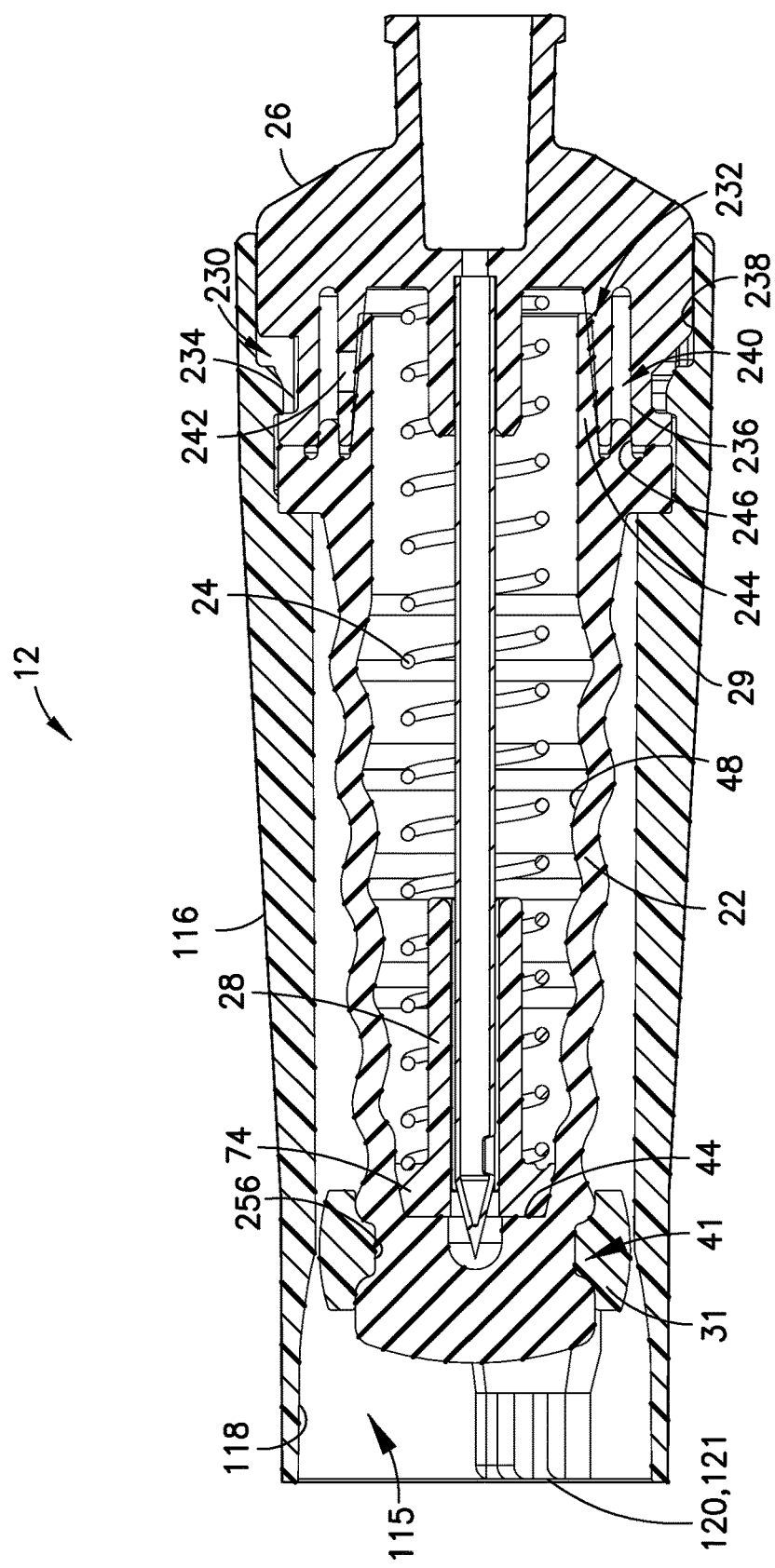
FIG. 16 is an assembled, cross-sectional view of the injector adapter of FIG. 15 in accordance with an embodiment of the present invention.

Referring to FIG. 15, spring 24 includes a distal end 60 and a proximal end 62. Spring 24 provides a biasing force that promotes cannula seal 22 to enclose cannula 20 in the sealed position as will be described in more detail below. Referring to FIG. 16, spring 24 is disposed over cannula 20 such that spring 24 is radially positioned between cannula 20 and cannula seal 22, i.e., cannula seal 22 encloses spring 24 and cannula 20.

Referring to FIG. 16, spring 24 is disposed over cannula 20 and within cannula seal 22 such that distal end 60 of spring 24 engages shoulder portion 44 of cannula seal 22. In this manner, spring 24 exerts the biasing force on shoulder portion 44 of cannula seal 22. Shoulder portion 44 of cannula seal 22 also ensures that spring 24 is secured between shoulder portion 44 and needle hub 26.

Referring to FIGS. 15-18, needle hub 26 generally includes a distal end 50 and a proximal end 52. Proximal end 52 of needle hub 26 includes a barrel connection portion 54. In one embodiment, barrel connection portion 54 is a female luer connector that is configured to mate with a male luer connector, although other suitable connectors may be utilized. The barrel connection portion 54 includes a projection that is configured to be received by a corresponding threaded portion of the male luer connector. Other arrangements for the barrel connection portion 54 may be utilized that deter undesired disconnection from the needle hub 26. Needle hub 26 supports and is secured to a portion of cannula 20. In one embodiment, the needle hub 26 is secured to the cannula 20 via an adhesive, such as an epoxy, although other suitable arrangements for securing the cannula 20 to the needle hub 26 may be utilized. Distal end 50 of needle hub 26 also provides a connection with proximal end 62 of spring 24 so that distal end 60 of spring 24 may be compressed relative to proximal end 62 of spring 24 when cannula 20 pierces cannula seal 22 as will be described in more detail below. With spring 24 compressed, spring 24 exerts a biasing force that promotes cannula seal 22 to elastically enclose cannula 20. Referring to FIG. 25, in one embodiment, with cannula seal 22 in the sealed position, spring 24 is loaded between shoulder portion 44 of cannula seal 22 and needle hub 26 in a slightly compressed position so that spring 24 exerts a biasing force that retains cannula seal 22 in the sealed position.

In one embodiment, referring to FIGS. 15-18, annular ribbed members 46 of cannula seal 22 provide an additional biasing force that retains cannula seal 22 in the sealed position. Referring to FIG. 23C, as cannula 20 is brought into contact with vial adapter 14, annular ribbed members 46 of cannula seal 22 and spring 24 are compressed as cannula 20 pierces cannula seal 22 and vial adapter 14. With annular ribbed members 46 of cannula seal 22 compressed, annular ribbed members 46 exert an additional biasing force that promotes cannula seal 22 to elastically enclose cannula 20.

Referring to FIGS. 15-18, housing 29 generally includes a distal or first end 110, a proximal or second end 112, and a sidewall 114 extending therebetween. Sidewall 114 of housing 29 defines a housing chamber 115. Housing chamber 115 is sized and shaped to contain and house the components of injector adapter 12. The sidewall 114 of housing 29 includes an exterior wall surface 116 and an interior wall surface 118. In one embodiment, the interior wall surface 118 of the sidewall 114 includes a connection element 120. Referring to FIG. 16, connection element 120 extends inwardly from interior wall surface 118 of sidewall 114 into housing chamber 115 adjacent distal end 110. As discussed in detail below, connection element 120 is engageable with a connection element of a vial adapter or an IV line adapter to secure injector adapter 12 to a vial adapter or an IV line adapter such that significant relative movement between injector adapter 12 and the vial adapter or IV line adapter is prevented. In one embodiment, connection element 120 comprises a first projecting member 121. In one embodiment, first projecting member 121 includes an elastically deformable tab for engagement with a connection element of a vial adapter or an IV line adapter as described in more detail below. In one embodiment, referring to FIG. 4, housing 29 also includes an elastically deformable portion for engagement with a connection element of a vial adapter or an IV line adapter as described in more detail below.

Figure 17:
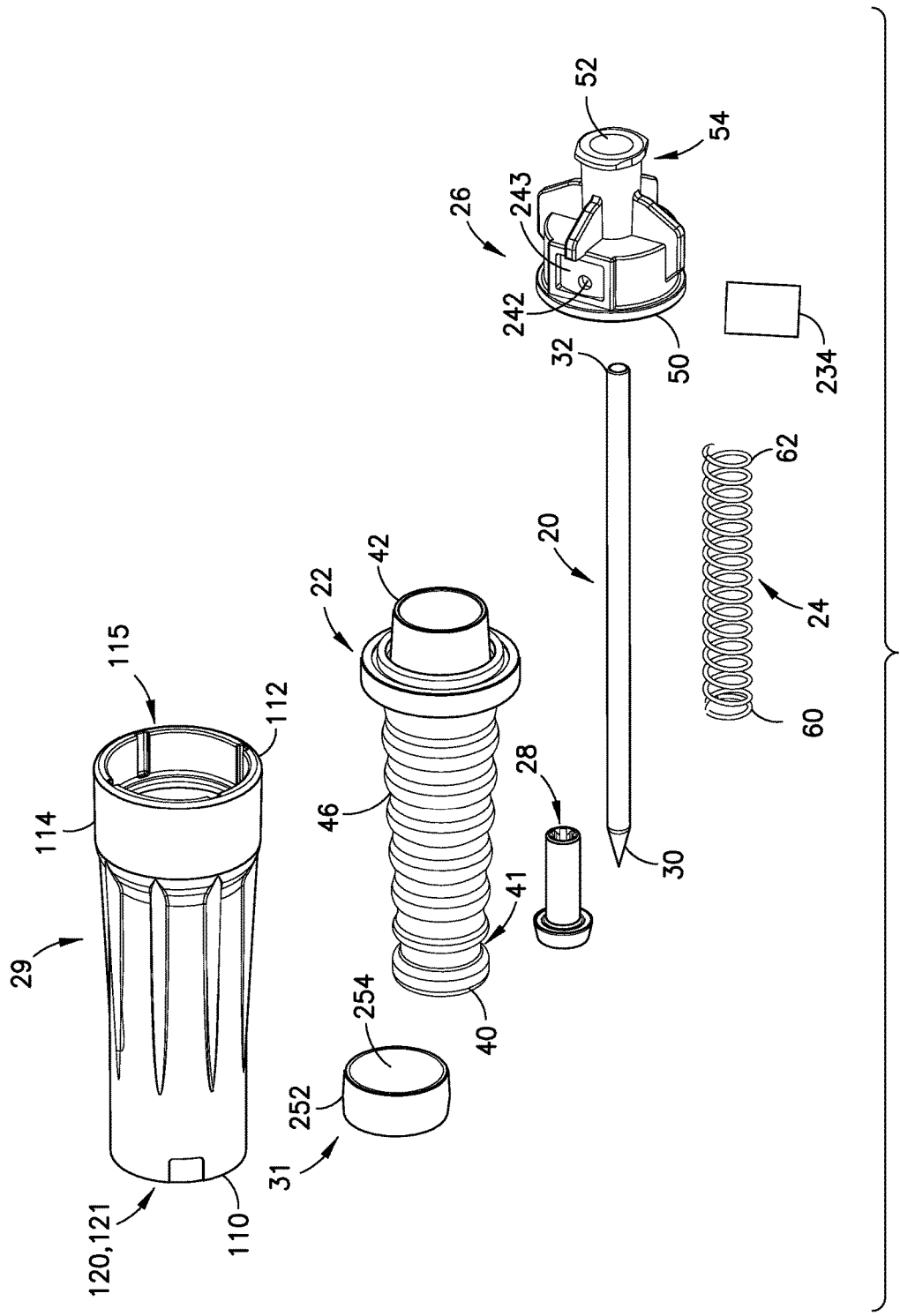
FIG. 17 is another exploded, perspective view of an injector adapter in accordance with an embodiment of the present invention.
Figure 18:
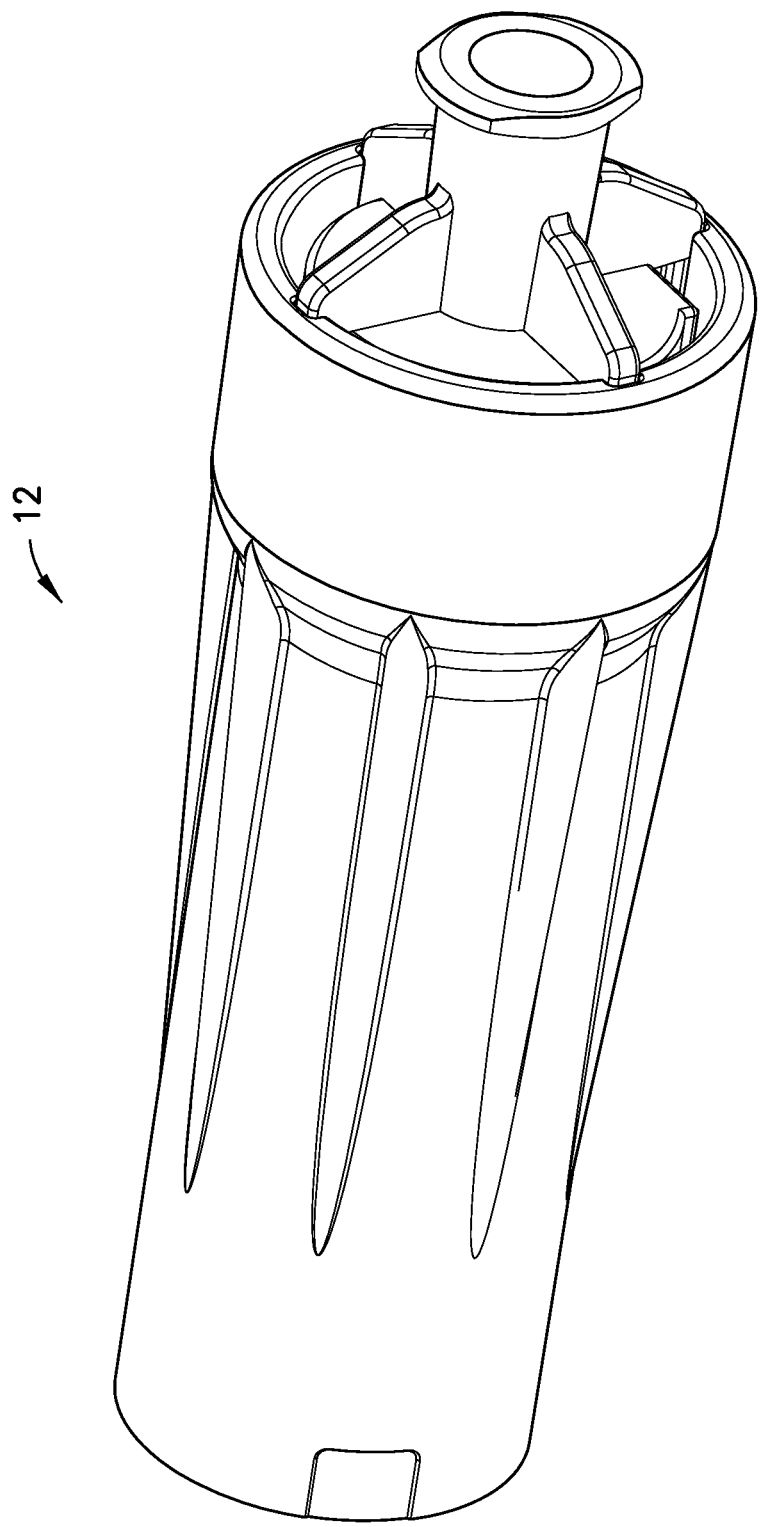
FIG. 18 is a perspective view of an injector adapter in accordance with an embodiment of the present invention.

In one embodiment, the interior wall surface 118 of the sidewall 114 includes a second connection element 122. Referring to FIG. 17, second connection element 122 extends inwardly from interior wall surface 118 of sidewall 114 into housing chamber 115 adjacent distal end 110. Second connection element 122 is spaced a distance from first connection element 120. In one embodiment, second connection element 122 is spaced approximately 180 degrees (180°) from first connection element 120. Second connection element 122 is engageable with a connection element of a vial adapter or an IV line adapter to secure injector adapter 12 to a vial adapter or an IV line adapter. In one embodiment, second connection element 122 comprises a second projecting member 123. In one embodiment, second projecting member 123 includes an elastically deformable tab for engagement with a connection element of a vial adapter or an IV line adapter as described in more detail below.

The first and second connection elements 120, 122 of injector adapter 12 form a first portion of a connection system of the present disclosure which is compatible with connection elements of a vial adapter or an IV line adapter which form a second portion of a connection system of the present disclosure as discussed in more detail below.

In one embodiment, a material that is capable of elastic flexing without cracking is used to form first and second connection elements 120, 122 of injector adapter 12. It is contemplated that flexible polymers may be used to form first and second connection elements 120, 122 of injector adapter 12. For example, flexible polymers such as polyolefines may be used, e.g., polypropylene, polyethylene, and their co-polymers.

Housing 29 provides a protective housing which seals the components of injector adapter 12 within housing 29, i.e., housing 29 provides a leak prevention and protection enclosure, protects the components of injector adapter 12 contained within housing 29, and/or maintains a sealed, sterilized environment within housing 29. Housing 29 also provides connection elements 120, 122 which provide for engagement with a connection element of a vial adapter or an IV line adapter to secure injector adapter 12 to a vial adapter or an IV line adapter. In one embodiment, referring to FIG. 4, housing 29 also includes an elastically deformable portion for engagement with a connection element of a vial adapter or an IV line adapter as described in more detail below.

Referring to FIGS. 15-18, in one embodiment, injector adapter 12 includes cannula stabilizing member 28. Cannula stabilizing member 28 includes a distal end 70, a proximal end 72, and an annular ring 74 therebetween. Referring to FIG. 16, cannula stabilizing member 28 is disposed within cannula seal 22 such that annular ring 74 of cannula stabilizing member 28 engages shoulder portion 44 of cannula seal 22. In this position, cannula stabilizing member 28 supports a portion of cannula 20 and provides stability to cannula 20 during engagement of cannula 20 with a vial or other device. With cannula stabilizing member 28 positioned within cannula seal 22, spring 24 is disposed over cannula 20 and within cannula seal 22 such that distal end 60 of spring 24 engages annular ring 74 of cannula stabilizing member 28. In this manner, spring 24 exerts the biasing force on annular ring 74 of cannula stabilizing member 28 which exerts the biasing force on shoulder portion 44 of cannula seal 22.

Referring to FIGS. 16 and 17, in one embodiment, injector adapter 12 includes gliding ring 31. Gliding ring 31 includes an exterior wall surface, i.e., a gliding surface 252 and an interior surface 254. In one embodiment, the interior surface 254 of gliding ring 31 includes an annular protrusion 256. The annular protrusion 256 extends radially inwards from interior surface 254. Referring to FIG. 16, gliding ring 31 is disposed within housing 29 such that annular protrusion 256 is received within annular cavity 41 of cannula seal 22 to secure the gliding ring 31 to the cannula seal 22 such that the gliding ring 31 is positioned between cannula seal 22 and interior wall surface 118 of housing 29. In this position, gliding ring 31 supports a portion of cannula seal 22 and provides stability to cannula seal 22 within housing 29 during engagement of cannula 20 with a vial or other device. Gliding ring 31 also provides stability to cannula seal 22 with cannula seal 22 moving within housing 29.

Referring to FIGS. 15-18, in one embodiment, injector adapter 12 is configured to provide an aspiration arrangement 230 to allow air to enter the injector adapter 12 for aspirating air into a syringe barrel while using seal and pressure equalization system 10. In particular, the aspiration arrangement 230 allows a user to aspirate air into the barrel chamber 176 after injector adapter 12 is secured to the barrel assembly 16. In, one embodiment, the aspiration arrangement 230 includes a one-way valve 232 and filter 234. As shown in FIG. 16, the needle hub 26 includes an inner wall 236 and an outer wall 238 that defines an annular recess 240. The needle hub 26 further defines at least one passageway 242 that extends perpendicularly to a longitudinal axis of the hub 26. The passageway 242 extends through the inner wall 236. The outer wall 238 defines a cutout 243 that is configured to receive the filter 234. The cutout 243 is in fluid communication with the passageway 242 and the annular recess 240. In one embodiment, as shown in FIGS. 15-17, the filter 234 is a flat filter sheet positioned within the cutout 243, although other suitable arrangements may be utilized. For example, the filter 234 may be ring-shaped and fitted within the annular recess 240 rather than being positioned within the cutout 243. The filter 234 may be any suitable commercially available filter, such as a particulate air filter having a pore size of 0.2 µm or larger. The filter 234 may be configured remove viable micro-organisms.

Referring again to FIG. 16, in one embodiment, the one-way valve 232 is embodied as an extension 244 of the cannula seal 22 that extends into the needle hub 26. The extension 244 is formed integrally with the cannula seal 22, although the extension 244 may be formed separately. The extension 244 of the cannula seal 22 abuts and extends along at least a portion of an inner surface 246 of the inner wall 236. The extension 244 is configured to selectively allow the flow of outside air through the passageway 242 and the filter 234 and into the cannula seal 22. In particular, in response to a pressure drop within the cannula seal 22 caused by aspiration, the extension 244 will deflect inwardly to open the passageway 242 and allow outside air to be drawn into the barrel chamber 176 of barrel assembly 16. After aspiration, the extension 244 will return to its original position to block or close the passageways 242. When the cannula seal 22 is under a positive pressure, the extension 244 is forced radially outward and continues to block and seal the passageway 242. Air may first be injected into the vial chamber 96 of vial 90 prior to withdrawing fluid, such as substance 98, from the vial chamber 96. Accordingly, the one-way valve 232 and filter 234 allows a user to aspirate air into the barrel chamber 176 after the injector adapter 12 is secured to the barrel assembly 16. Furthermore, the filter 234 is configured to filter the outside air that is aspirated into the barrel assembly 16, which advantageously allows clean filter air to be injected into the vial chamber 96.

Referring to FIGS. 22-26, proximal end 52 of needle hub 26 is attached to a barrel 160 of barrel assembly 16. With needle hub 26 supporting a portion of cannula 20 and with proximal end 52 of needle hub 26 attached to barrel 160 of barrel assembly 16, needle hub 26 attaches cannula 20 to barrel assembly 16 such that cannula 20 is in fluid communication with barrel chamber 176 of barrel 160.

Figure 23A:
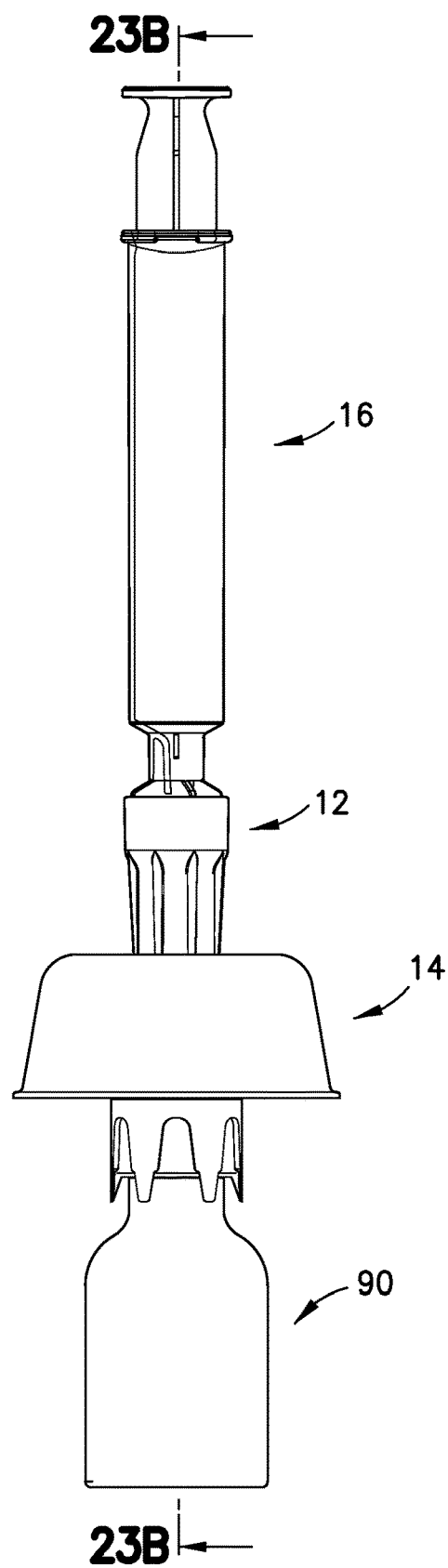
FIG. 23A is an assembled, perspective view of a system in accordance with an embodiment of the present invention.
Figure 23B:
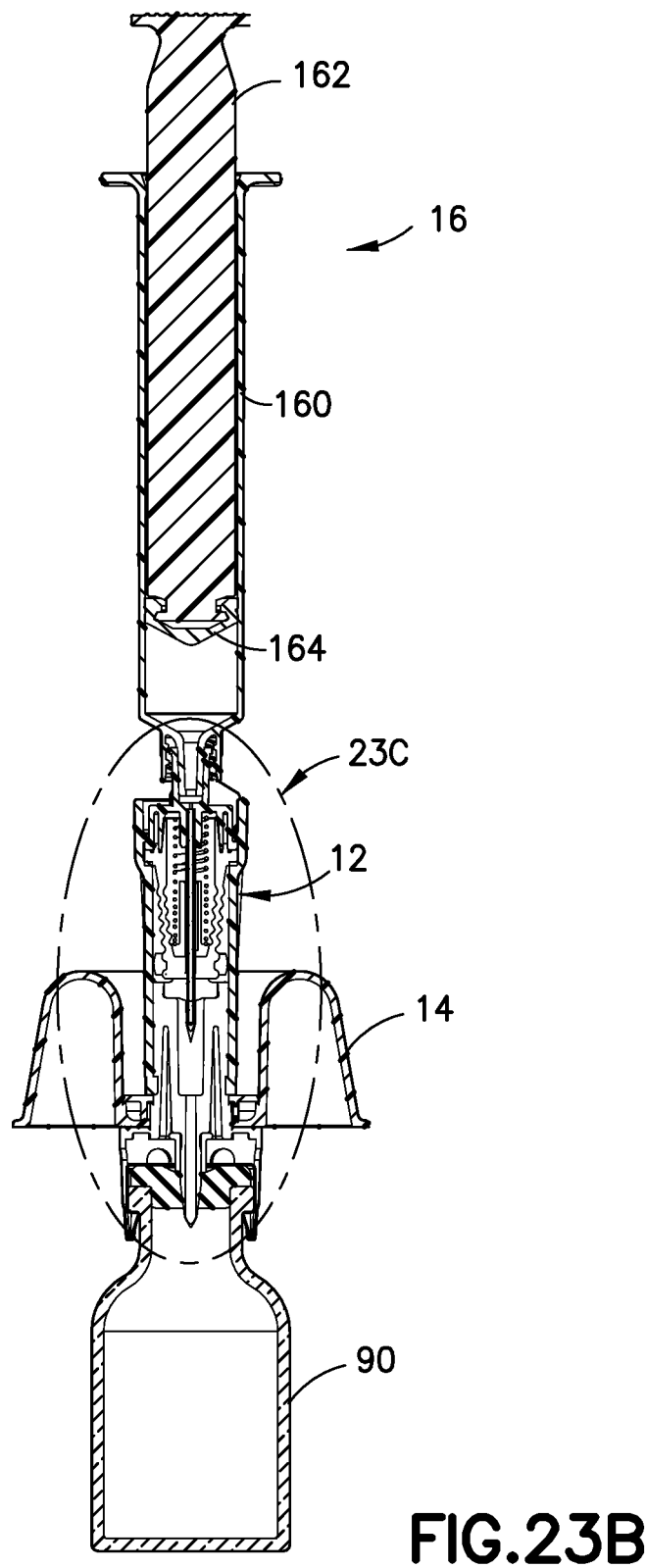
FIG. 23B is a cross-sectional view of the system taken along line 23B-23B of FIG. 23A in accordance with an embodiment of the present invention.
Figure 23C:
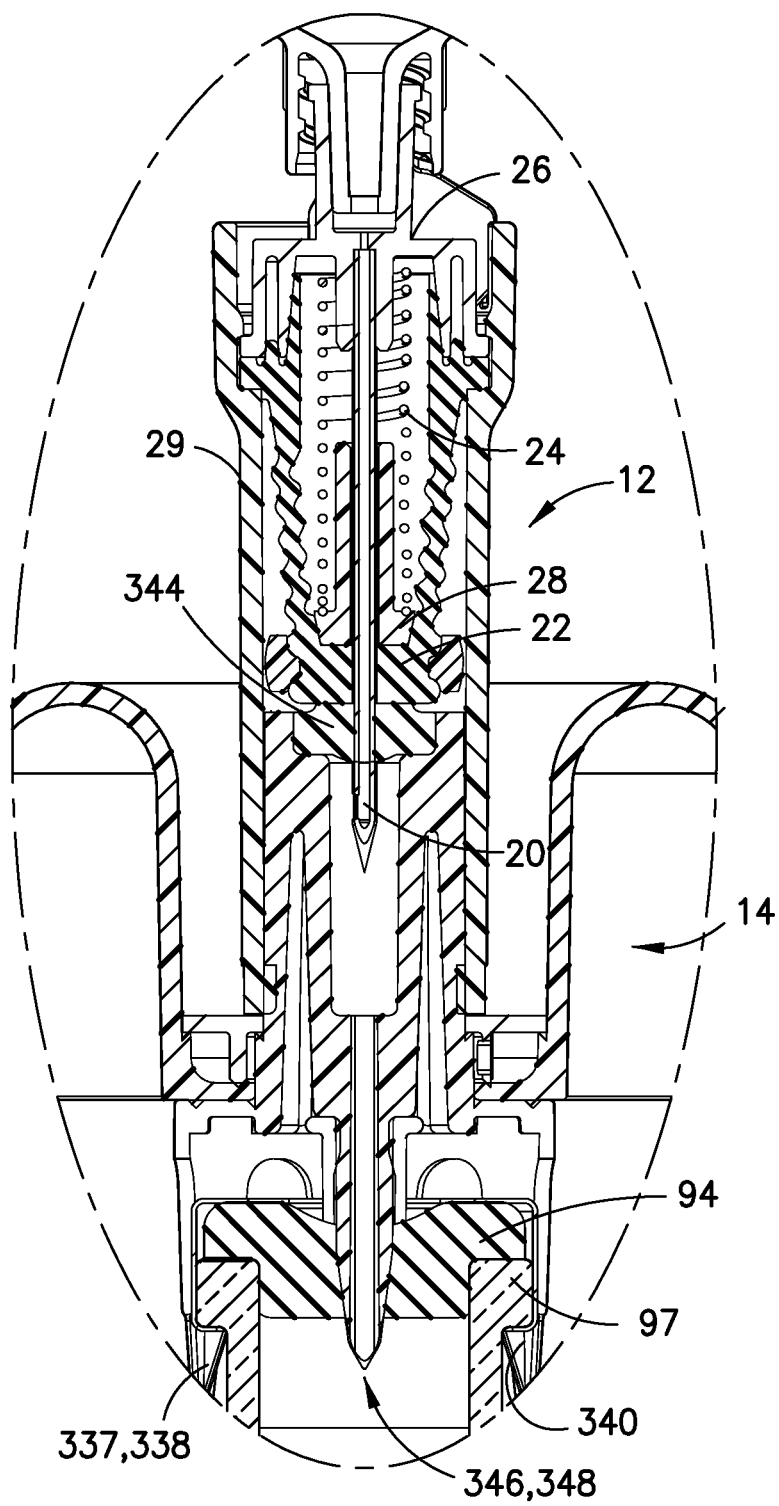
FIG. 23C is a detailed, fragmentary view of FIG. 23B in accordance with an embodiment of the present invention.

Referring to FIG. 23B, barrel assembly 16 includes barrel 160, a plunger rod 162, and a stopper 164. Barrel assembly 16 may be adapted for the dispensing and delivery of a fluid and/or collection of a fluid. For example, barrel assembly 16 may be used for injection or infusion of fluid such as a medication into a patient. Barrel assembly 16 is contemplated for use in connection with a needle, such as by connecting barrel assembly 16 to cannula 20 as described, connecting barrel assembly 16 to a separate needle assembly (not shown), or alternatively, for connection with an intravenous (IV) connection assembly such as IV line adapter 18. It can be appreciated that the present disclosure can be used with any type of syringe assembly, including, but not limited to, metered dose syringes, aspiration syringes for withdrawing fluid from a patient or medication from a container or vial, and the like.

Referring to FIGS. 12A-14B, IV line adapter 18 includes first end 130 and opposing second end 131. IV line adapter 18 provides a compact and accessible connector for connecting a cartridge or barrel containing a reconstituted drug to an intravenous line or an injection apparatus for administering the drug to a patient.

First end 130 of IV line adapter 18 includes a connection system 132. Connection system 132 of IV line adapter 18 forms a portion of a connection system of the present disclosure which is compatible with a connection system 120, 122 of injector adapter 12 which form another portion of a connection system of the present disclosure as discussed in more detail below.

Figure 12A:
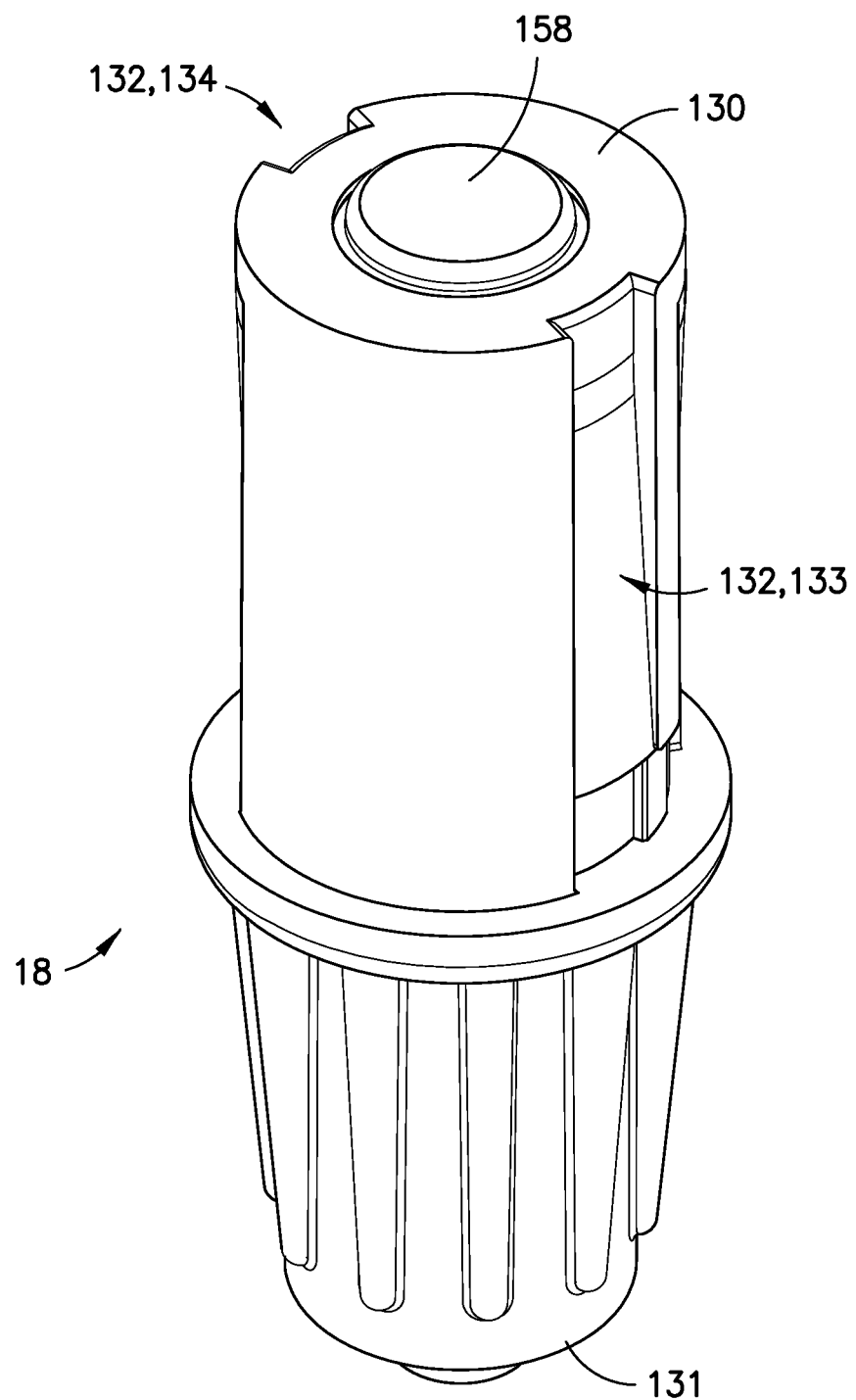
FIG. 12A is a perspective view of an intravenous line adapter in accordance with an embodiment of the present invention.
Figure 12C:
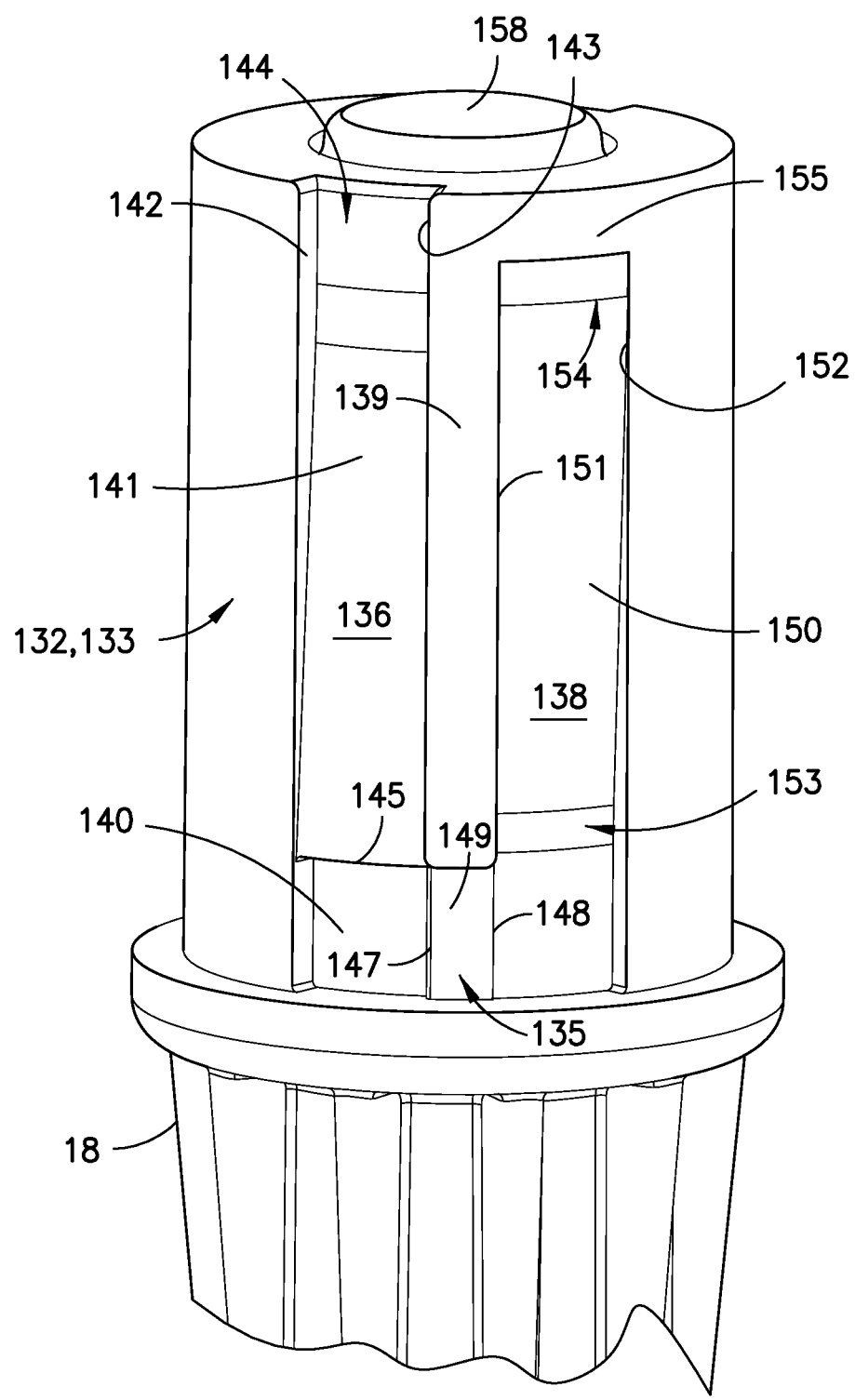
FIG. 12C is a perspective view of a first side of an intravenous line adapter in accordance with an embodiment of the present invention.

Referring to FIGS. 12A-12C, in one embodiment, connection system 132 includes a first connection element 133 disposed at first end 130 of IV line adapter 18 which is engageable with a connection element 120, 122 of an injector adapter 12 to secure the injector adapter 12 to IV line adapter 18. In one embodiment, first end 130 of IV line adapter 18 includes a second connection element 134. Second connection element 134 is spaced a distance from first connection element 133. In one embodiment, second connection element 134 is spaced approximately 180 degrees (180°) from first connection element 133. Second connection element 134 is engageable with a connection element 120, 122 of an injector adapter 12 to secure the injector adapter 12 to IV line adapter 18 such that significant relative movement between injector adapter 12 and IV line adapter 18 is prevented.

Referring to FIGS. 12A-12C, first connection element 133 of connection system 132 includes a first connection path 136, a first disconnection path 138, and a first securement element 140 disposed between the first connection path 136 and first disconnection path 138. In one embodiment, first connection path 136, first disconnection path 138, and first securement element 140 together generally define a U-shaped path. First connection path 136 is distinct from first disconnection path 138. In this manner, the distinct connection and disconnection paths allow for the fine tuning of tactile and audible responses separately for connection and disconnection movements. In one embodiment, divider wall 139 is disposed between first connection path 136 and first disconnection path 138.

It is contemplated that most polymers may be used for first connection element 133 of IV line adapter 18. In one embodiment, a wide variety of thermoplastic and thermosetting polymers and similar materials may be used to form first connection element 133 of IV line adapter 18. In one embodiment, first connection element 133 of IV line adapter 18 is made from a rigid material such as a hard plastic, metal, or ceramic material. The important characteristics of the materials used to make first connection element 133 of IV line adapter 18 is that they are a more rigid material than the materials used to form connection element 120 of injector adapter 12.

In one embodiment, first connection path 136 comprises a first connection channel. In one embodiment, first disconnection path 138 comprises a first disconnection channel. In one embodiment, first securement element 140 comprises a locking recess.

First connection path 136 includes a connection guide surface 141, a first connection guide wall 142, and a second connection guide wall 143 which together form a channel that guides connection element 120 of injector adapter 12 to enter engagement with IV line adapter 18 as described in more detail below. Connection guide surface 141 includes an entry portion 144 and an exit portion 145 adjacent securement element 140. In one embodiment, guide surface 141 tapers upwards from entry portion 144 to exit portion 145. In this manner, guide surface 141 receives, guides, and deforms connection element 120 of injector adapter 12 as described in more detail below.

First connection path 136 includes a step member 135 disposed between first securement element 140 and first disconnection path 138. Step member 135 includes an exit recess step 147, an enter disconnection path step 148, and a top step surface 149 disposed therebetween. Step member 135 provides a component that allows connection element 120 of injector adapter to be rotated out from engagement with securement element 140. Also, step member 135 can be used to tune resistance and provide tactile feel during a disconnection movement as described in more detail below.

First disconnection path 138 includes a disconnection guide surface 150, a first disconnection guide wall 151, and a second disconnection guide wall 152 which together form a channel that guides connection element 120 of injector adapter 12 to exit IV line adapter 18 as described in more detail below. Disconnection guide surface 150 includes an entry portion 153 adjacent step member 135 and an exit portion 154 that includes a barrier exit wall 155. In one embodiment, guide surface 150 tapers upwards from entry portion 153 to exit portion 154. In this manner, guide surface 150 receives, guides, and deforms connection element 120 of injector adapter 12 as described in more detail below.

Figure 12D:
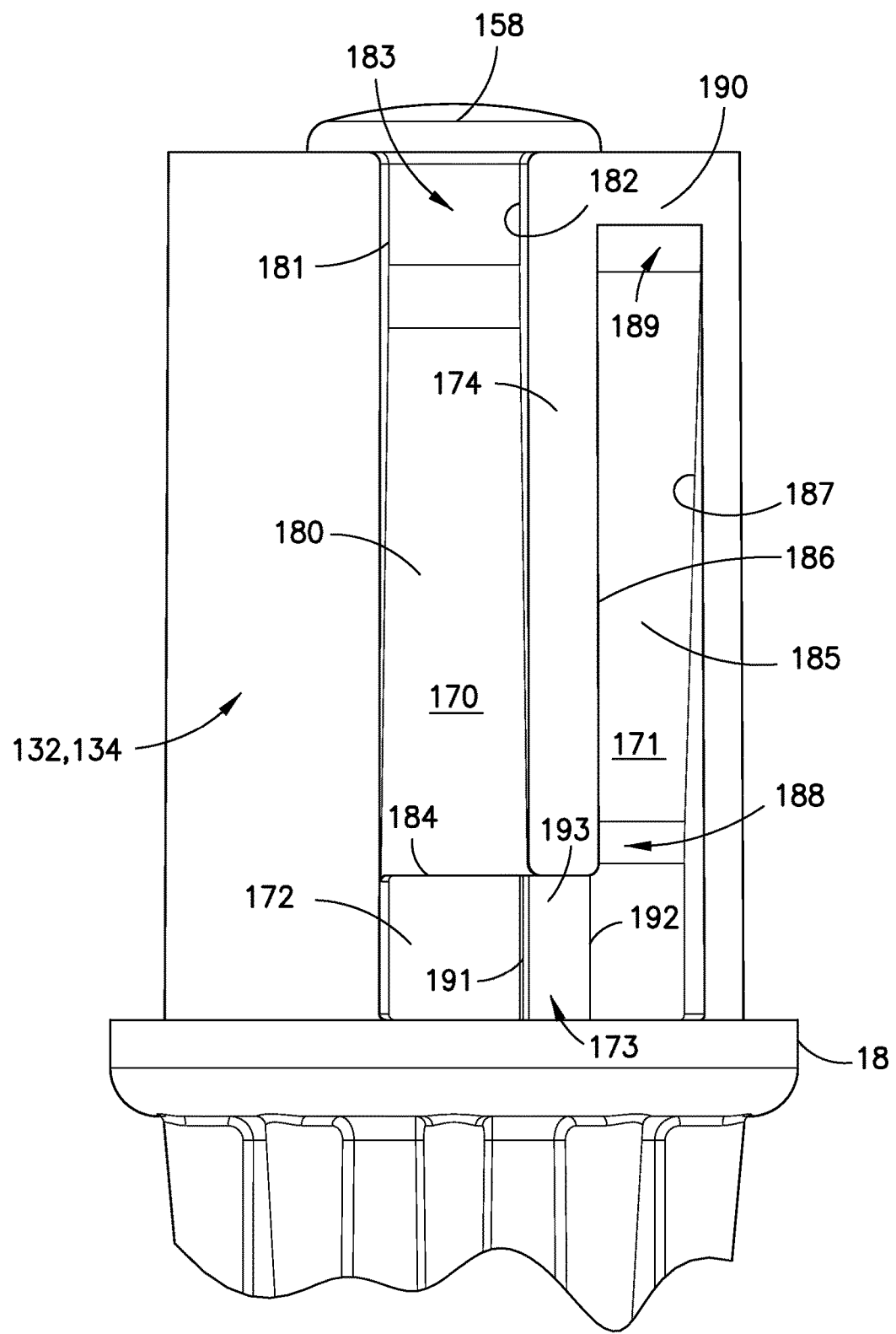
FIG. 12D is a perspective view of a second side of an intravenous line adapter in accordance with an embodiment of the present invention.
Figure 13A:
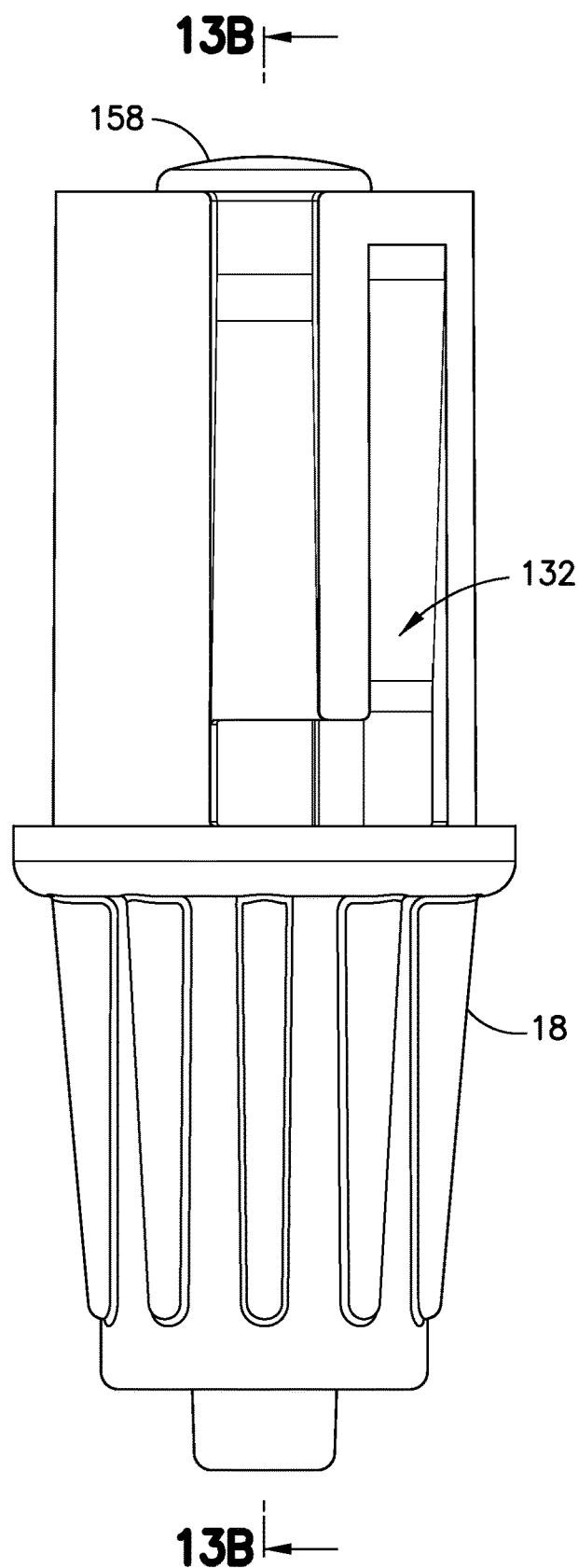
FIG. 13A is a perspective view of an intravenous line adapter in accordance with an embodiment of the present invention.
Figure 13B:
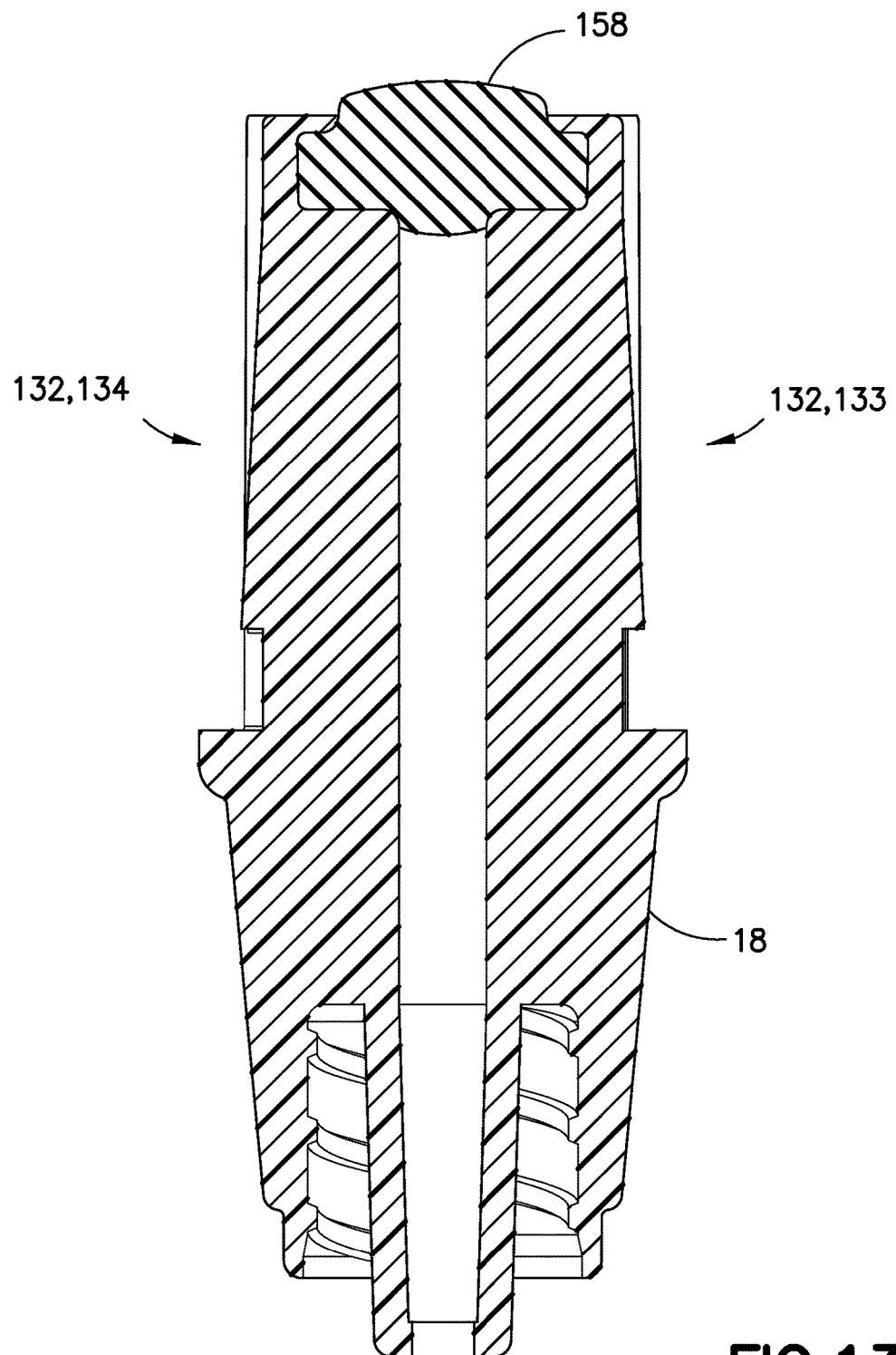
FIG. 13B is a cross-sectional view of the intravenous line adapter of FIG. 13A taken along line 13B-13B of FIG. 13A in accordance with an embodiment of the present invention.
Figure 14A:
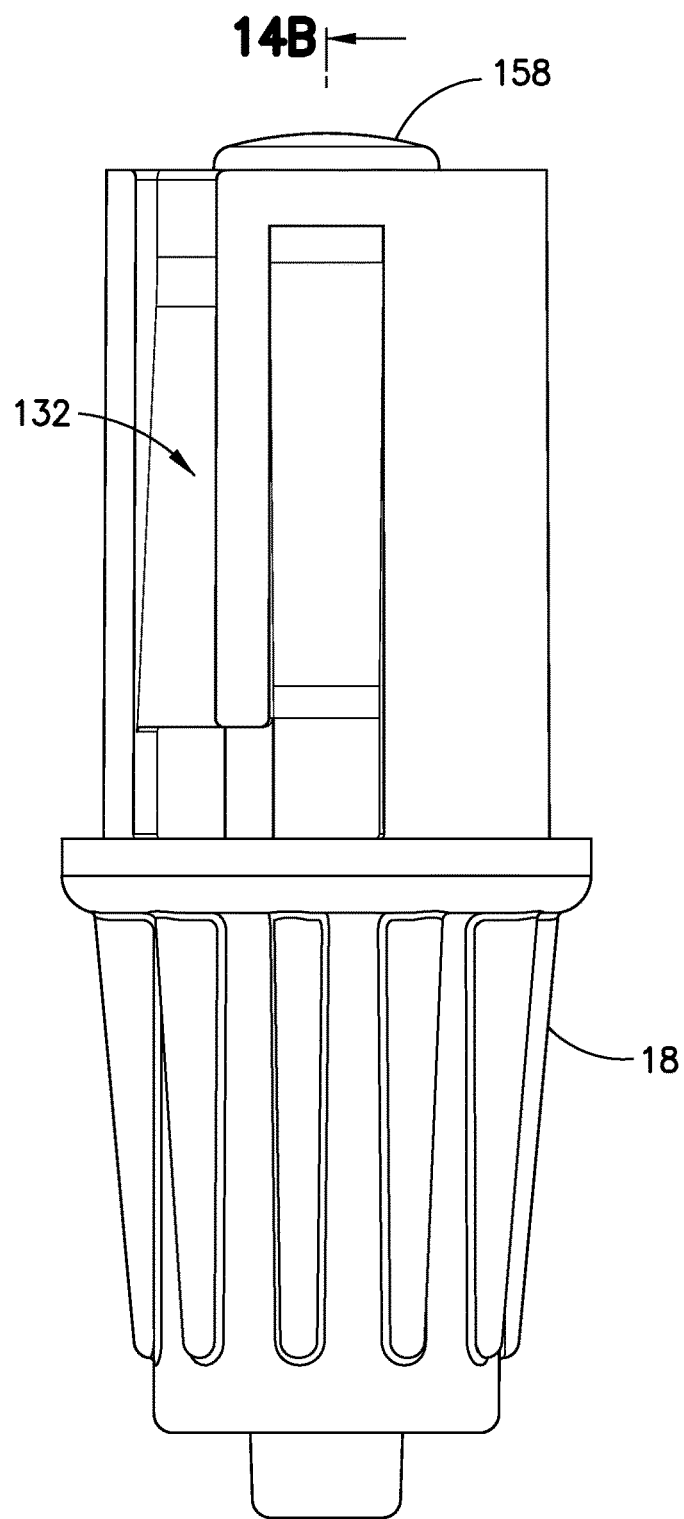
FIG. 14A is a perspective view of an intravenous line adapter in accordance with an embodiment of the present invention.
Figure 14B:
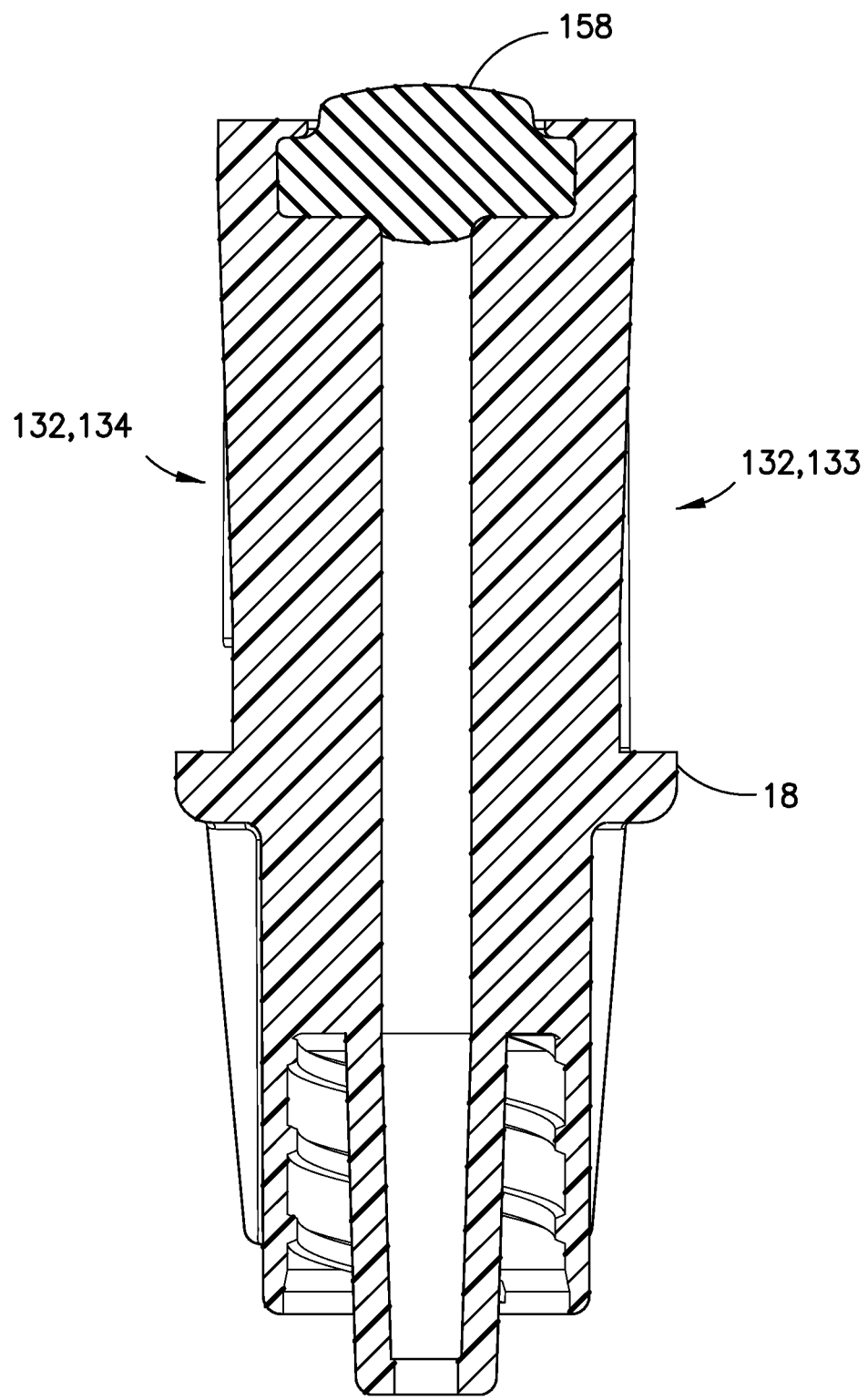
FIG. 14B is a cross-sectional view of the intravenous line adapter of FIG. 14A taken along line 14B-14B of FIG. 14A in accordance with an embodiment of the present invention.

Referring to FIGS. 12B and 12D, second connection element 134 of connection system 132 includes a second connection path 170, a second disconnection path 171, and a second securement element 172 disposed between the second connection path 170 and second disconnection path 171. In one embodiment, second connection path 170, second disconnection path 171, and second securement element 172 together generally define a U-shaped path. Second connection path 170 is distinct from second disconnection path 171. In this manner, the distinct connection and disconnection paths allow for the fine tuning of tactile and audible responses separately for connection and disconnection movements. In one embodiment, divider wall 174 is disposed between second connection path 170 and second disconnection path 171.

It is contemplated that most polymers may be used for second connection element 134 of IV line adapter 18. In one embodiment, a wide variety of thermoplastic and thermosetting polymers and similar materials may be used to form second connection element 134 of IV line adapter 18. In one embodiment, second connection element 134 of IV line adapter 18 is made from a rigid material such as a hard plastic, metal, or ceramic material. The important characteristics of the materials used to make second connection element 134 of IV line adapter 18 is that they are a more rigid material than the materials used to form second connection element 122 of injector adapter 12.

In one embodiment, second connection path 170 comprises a second connection channel. In one embodiment, second disconnection path 171 comprises a second disconnection channel. In one embodiment, second securement element 172 comprises a locking recess.

Second connection path 170 includes a connection guide surface 180, a first connection guide wall 181, and a second connection guide wall 182 which together form a channel that guides second connection element 122 of injector adapter 12 to enter engagement with IV line adapter 18 as described in more detail below. Connection guide surface 180 includes an entry portion 183 and an exit portion 184 adjacent securement element 172. In one embodiment, guide surface 180 tapers upwards from entry portion 183 to exit portion 184. In this manner, guide surface 180 receives, guides, and deforms second connection element 122 of injector adapter 12 as described in more detail below.

Second connection path 170 includes a step member 173 disposed between second securement element 172 and second disconnection path 171. Step member 173 includes an exit recess step 191, an enter disconnection path step 192, and a top step surface 193 disposed therebetween. Step member 173 provides a component that allows second connection element 122 of injector adapter 12 to be rotated out from engagement with securement element 172. Also, step member 173 can be used to tune resistance and provide tactile feel during a disconnection movement as described in more detail below.

Second disconnection path 171 includes a disconnection guide surface 185, a first disconnection guide wall 186, and a second disconnection guide wall 187 which together form a channel that guides second connection element 122 of injector adapter 12 to exit IV line adapter 18 as described in more detail below. Disconnection guide surface 185 includes an entry portion 188 adjacent step member 173 and an exit portion 189 that includes a barrier exit wall 190. In one embodiment, guide surface 185 tapers upwards from entry portion 188 to exit portion 189. In this manner, guide surface 185 receives, guides, and deforms second connection element 122 of injector adapter 12 as described in more detail below.

First end 130 of IV line adapter 18 includes a pierceable barrier membrane 158. The pierceable barrier membrane 158 provides for a liquid and gas tight seal between a piercing member of a barrel assembly and the pierceable barrier membrane 158 during fluid transfer of a medication to a patient so to minimize leakage and thereby prevent exposure of hazardous medicaments to a user. Barrier membrane 158 provides a self-sealing seal that, with a barrel assembly attached to IV line adapter 18, provides a leak-proof seal preventing any substance being administered to a patient from being exposed to a health care provider administering the medication. In one embodiment, barrier membrane 158 comprises a resilient material. For example, barrier membrane 158 is preferably a unitary device molded of any flexible, elastomeric material conventionally used for fabricating gas-proof closures. Barrier membrane 158 may be formed of a natural rubber material, polyurethane elastomers, butyl rubbers, or similar materials.

Figure 19B:
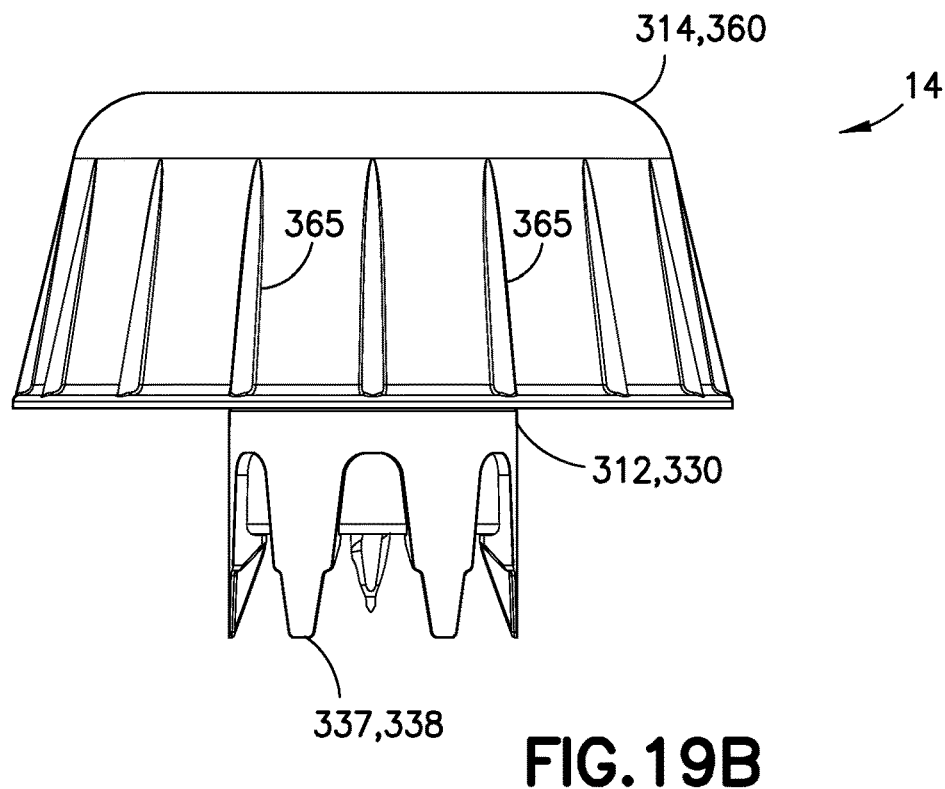
FIG. 19B is a side, perspective view of a vial adapter in accordance with an embodiment of the present invention.
Figure 19C:
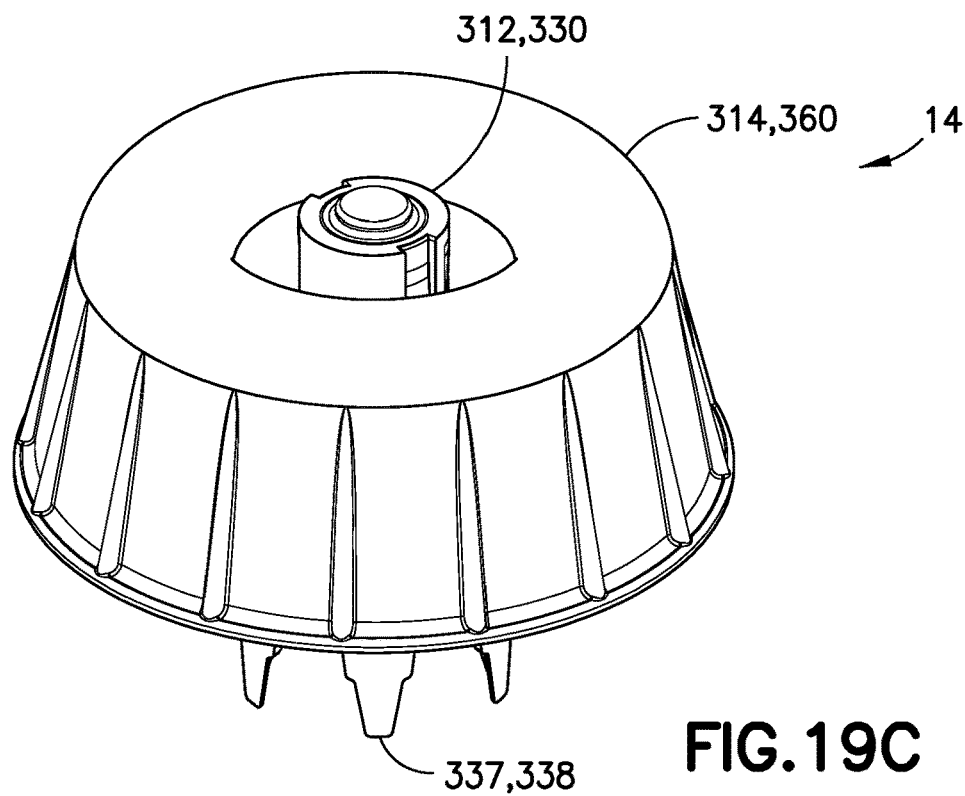
FIG. 19C is a perspective view of a vial adapter in accordance with an embodiment of the present invention.
Figure 19D:
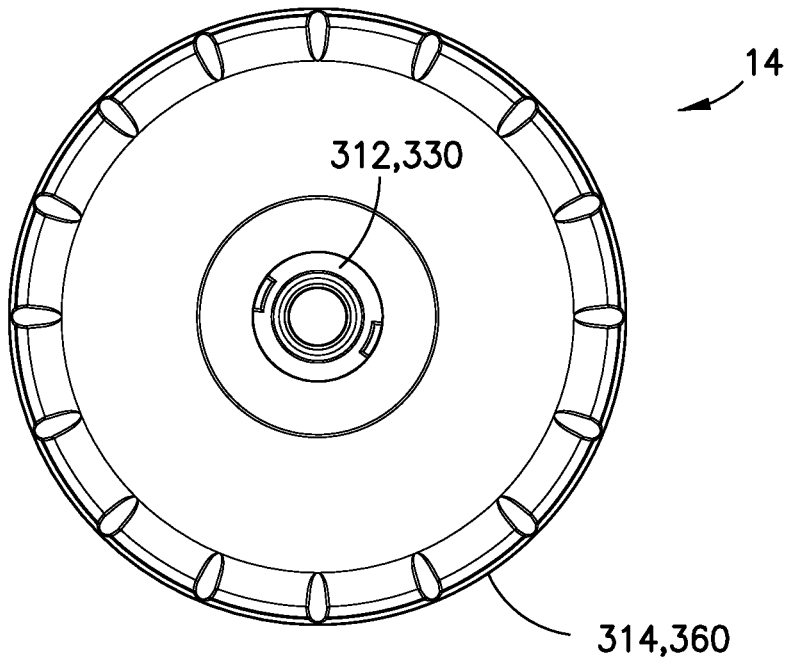
FIG. 19D is a plan view of a vial adapter in accordance with an embodiment of the present invention.
Figure 19E:
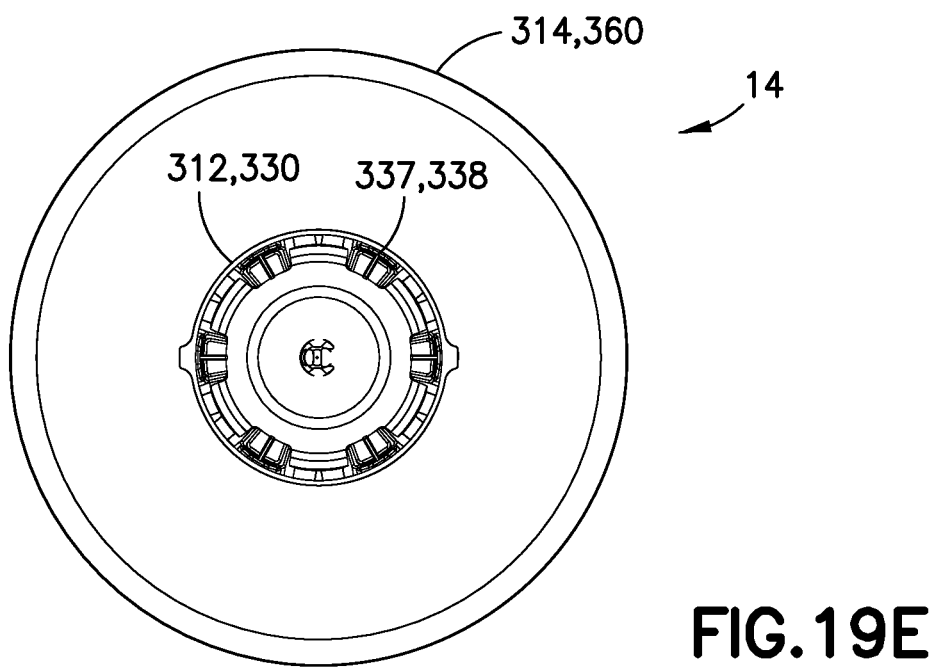
FIG. 19E is a bottom view of a vial adapter in accordance with an embodiment of the present invention.
Figure 19F:
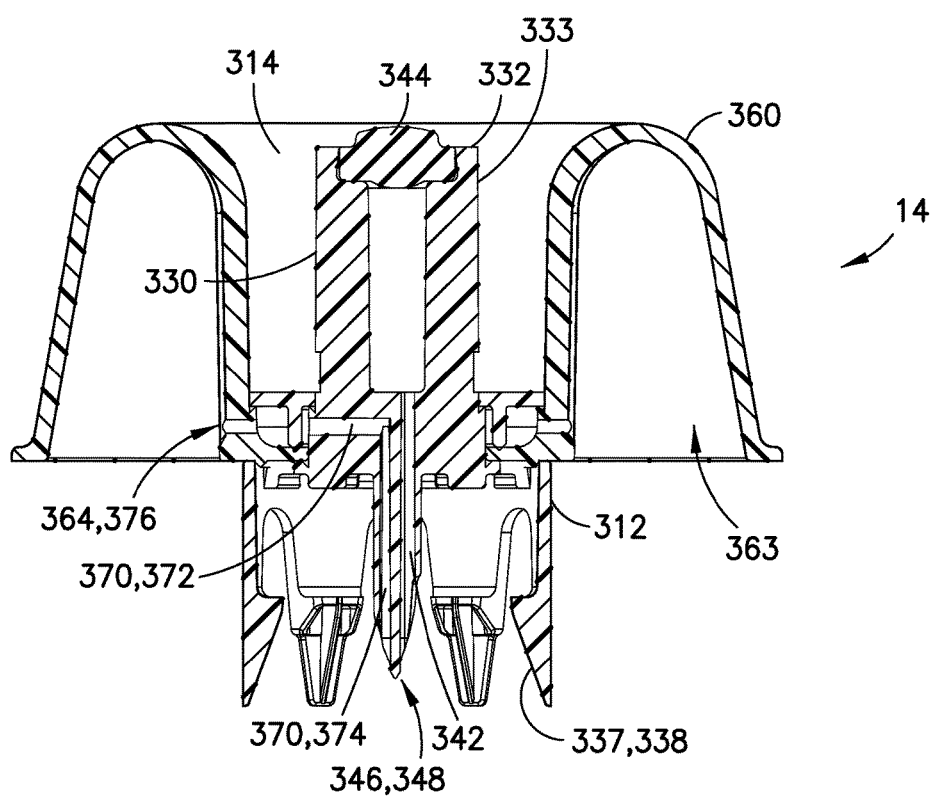
FIG. 19F is a cross-sectional view of the vial adapter of FIG. 19B in accordance with an embodiment of the present invention.

Referring to FIGS. 19A-19G, vial adapter 14 includes a vial access system 312 and a pressure equalization system 314. Vial adapter 14 is configured to establish fluid communication between a first container and a second container. For example, vial adapter 14 is attachable to a vial 90. Referring to FIGS. 20A and 20B, vial 90 may be a standard drug vial of any type having an open head portion 93 covered by a pierceable septum 94 of an elastomeric material. Walls 95 of vial 90 define vial chamber 96 for containing a substance 98. Vial septum 94 is engaged with head portion 93 of vial 90 to seal the substance 98 within vial chamber 96.

Vial adapter 14 is compatible with a system for the closed transfer of fluids that provides substantially leak-proof sealing and pressure balancing during engagement of a cannula with a vial, during transfer of a substance from a vial chamber to a barrel chamber via the cannula, and during disengagement of the cannula from the vial.

As shown in FIGS. 19A-19F, with pressure equalization system 314 secured to vial access system 312, vial adapter 14 includes first end 302, opposing second end 303, and wall 304 extending between first end 302 and second end 303. Wall 304 defines an exterior profile 306 as will be described in more detail below. With vial adapter 14 attached to a vial 90, the vial adapter 14 provides a leak-proof seal and pressure equalization system that prevents any substance contained within a chamber of the vial from being exposed to a health care provider reconstituting, transporting, or administering a drug.

The fit between vial adapter 14 and the packaging member provides a secure fit therebetween, such that, with vial adapter 14 received within the packaging member, the packaging member can be used as an interface between the hand of a user and vial adapter 14 so that vial adapter 14 can be placed onto a vial without taking vial adapter 14 out of the packaging member.

Figure 19G:
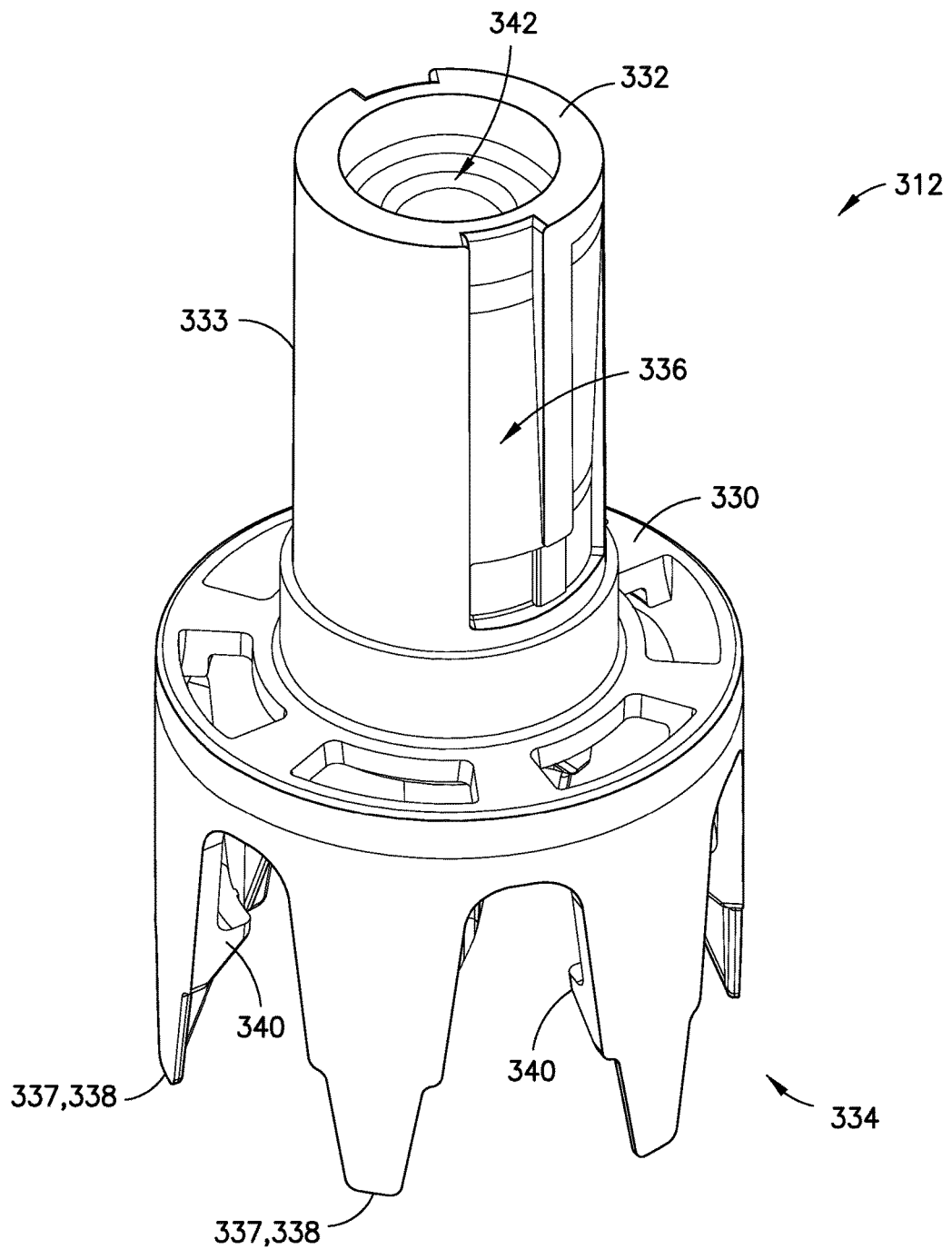
FIG. 19G is a perspective view of a vial access system in accordance with an embodiment of the present invention.
Figure 20A:
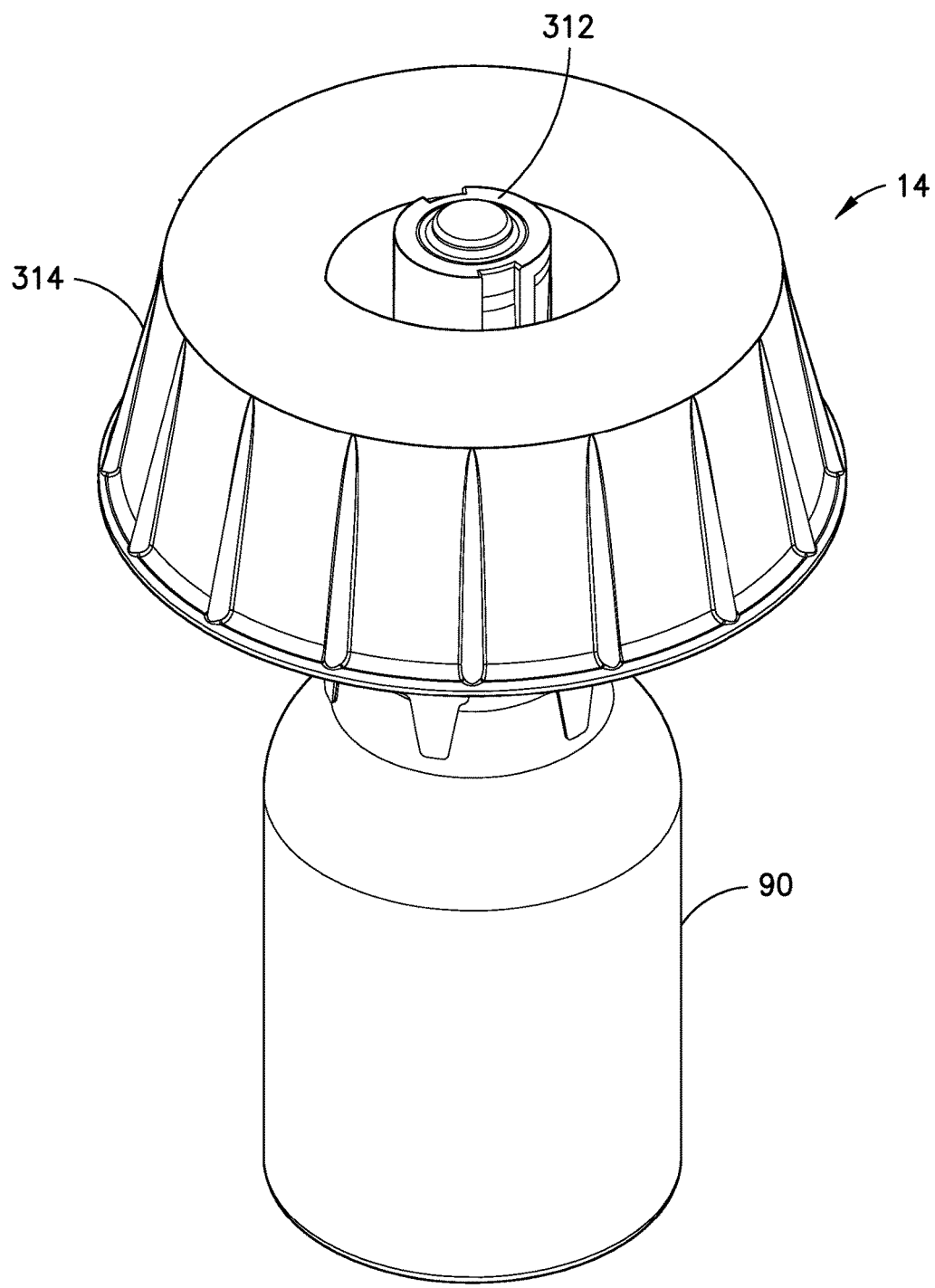
FIG. 20A is a perspective view of a vial adapter connected to a vial in accordance with an embodiment of the present invention.
Figure 20B:
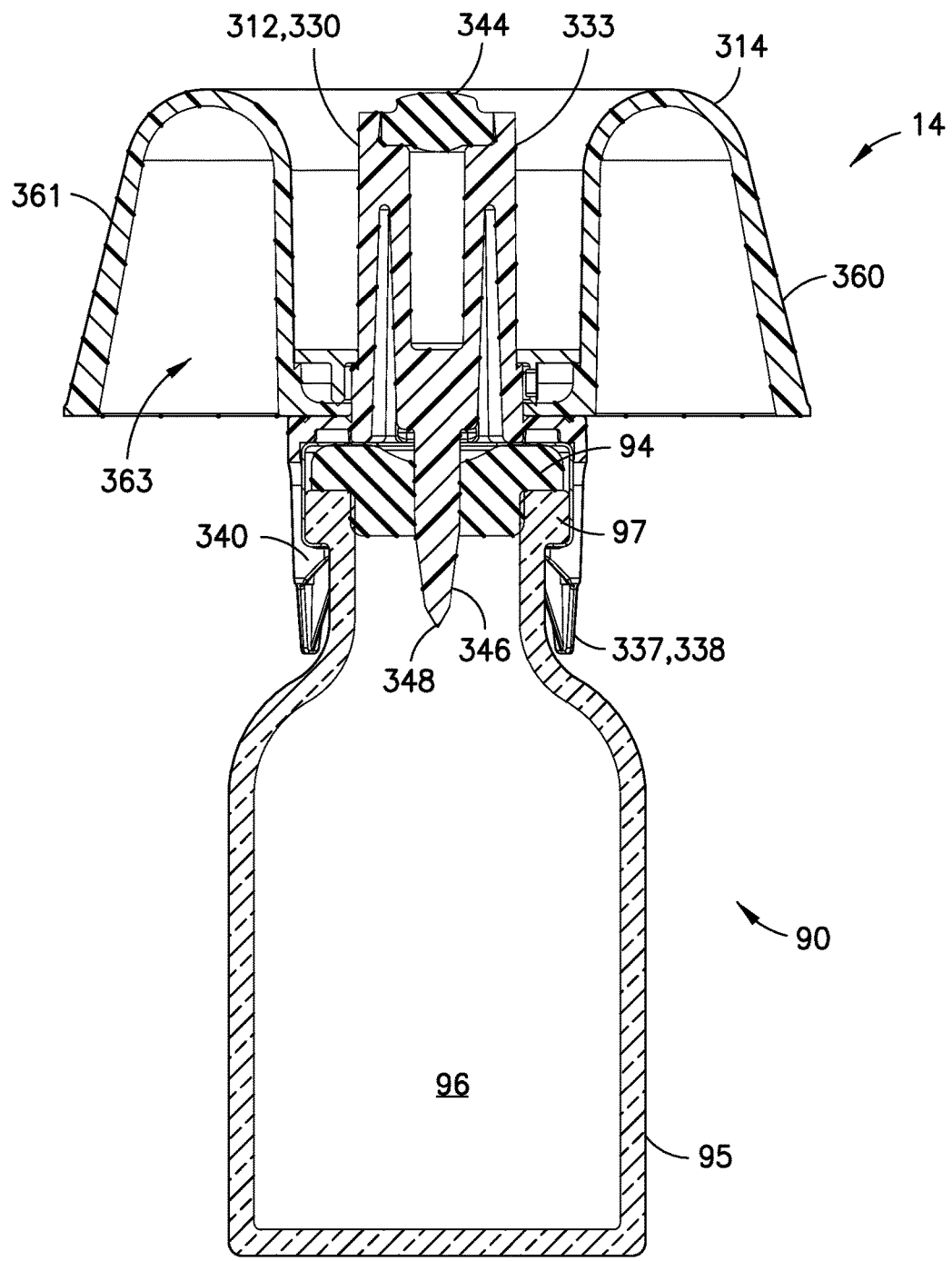
FIG. 20B is a cross-sectional view of the vial adapter connected to the vial of FIG. 20A in accordance with an embodiment of the present invention.

Referring to FIG. 19G, vial access system 312 of vial adapter 14 includes vial access housing 330 having first end 332 and opposing second end 334. First end 332 of vial access housing 330 includes a connection element or connection system 336. First connection element 336 is engageable with a connection element 120, 122 of an injector adapter 12 to secure the injector adapter 12 to vial adapter 14. In one embodiment, first end 332 of vial access housing 330 includes a second connection element or second connection system 339. Second connection element 339 is spaced a distance from first connection element 336. In one embodiment, second connection element 339 is spaced approximately 180 degrees (180°) from first connection element 336. Second connection element 339 is engageable with a connection element 120, 122 of an injector adapter 12 to secure the injector adapter 12 to vial adapter 14 such that significant relative movement between injector adapter 12 and vial adapter 14 is prevented.

In one embodiment, the first and second connection elements 336, 339 of vial adapter 14 form a second portion of a connection system of the present disclosure which is compatible with connection elements of an injector adapter which form a first portion of a connection system of the present disclosure as discussed in more detail below.

FIGS. 19A-19G illustrate another exemplary embodiment of the present disclosure. The connection system of first and second connection elements 336, 339 of vial adapter 14 illustrated in FIGS. 19A-19G include similar components to the connection system of first connection element 133 and second connection element 134 of IV line adapter 18 illustrated in FIGS. 12-14B, and the similar components are denoted by a reference number followed by the letter A. For the sake of brevity, these similar components and the similar steps of using the connection system of first and second connection elements 336, 339 of vial adapter 14 will not all be discussed in conjunction with the embodiment illustrated in FIGS. 19A-19G.

First end 332 of vial access housing 330 is substantially formed by a neck portion 333. In one embodiment, neck portion 333 may include a guiding groove arranged therein to guide corresponding guiding protrusions on a cannula adapter or syringe assembly, for example, to establish a secure attachment between the cannula adapter or syringe assembly and vial adapter 14 after which fluid communication can be established.

Referring to FIGS. 19A-19G, a vial connection member or vial engagement member 337 is disposed at second end 334 of vial access housing 330. In one embodiment, vial connection member 337 includes a plurality of vial grip members 338 that are disposed at second end 334 of vial access housing 330. Vial grip members 338 are attachable to a vial 90 to secure vial adapter 14 to the vial 90. Each vial grip member 338 includes a hook protrusion 340 arranged to engage a corresponding flange on a container such as a vial 90 as shown in FIGS. 20A and 20B. Vial connection member 337 of vial access housing 330 may be dimensioned to be attached to containers of any size and volume. In other embodiments, vial connection member 337 of vial access housing 330 may include other connection mechanisms for securing vial adapter 14 to vial 90 such as a threaded portion, a snap fit mechanism, locking tabs, or other similar mechanism.

A fluid transfer channel 342 extends substantially between first end 332 and second end 334 of vial access housing 330. The purpose of fluid transfer channel 342 is to permit a needle cannula to extend through vial access housing 330 of vial adapter 14 and to thereby permit fluid to be transferred through vial adapter 14.

Referring to FIG. 20B, a pierceable barrier member or vial seal membrane 344 is arranged in the fluid transfer channel 342 at first end 332 of vial access housing 330. The pierceable barrier member 344 provides for a liquid and gas tight seal between a piercing member and the pierceable barrier member 344 during fluid transfer so to minimize leakage and thereby prevent exposure of hazardous medicaments to a user. Vial seal membrane 344 provides a self-sealing seal that, with vial adapter 14 attached to vial 90 such that vial seal membrane 344 is aligned with vial septum 94, provides a leak-proof seal preventing any substance contained within vial chamber 96 from being exposed to a health care provider reconstituting, transporting, or administering a drug using system 10. Referring to FIGS. 23C-25, vial seal membrane 344, vial sleeve seal 350, and cannula seal 22 provide a leak-proof seal that is liquid tight and airtight preventing any substance residue from being exposed to a health care provider while reconstituting or withdrawing substance 98 from vial 90 to barrel 160 via cannula 20.

In one embodiment, vial seal membrane 344 comprises a resilient material. For example, vial seal membrane 344 is preferably a unitary device molded of any flexible, elastomeric material conventionally used for fabricating gas-proof closures. Vial seal membrane 344 may be formed of a natural rubber material, polyurethane elastomers, butyl rubbers, or similar materials. It is contemplated that vial seal membrane 344 is formed of a material having a Shore A hardness of approximately 10 to 50. It is also envisioned that vial seal membrane 344 can have other material hardness values that would provide an appropriate self-sealing material to provide a leak-proof seal with vial septum 94 of vial 90 and cannula seal 22, thereby preventing any liquid or medication residue from being exposed to a health care provider reconstituting, transporting, or administering a drug using system 10.

Protruding out from vial access housing 330 at second end 334 is a piercing member or spike member 346 which includes piercing tip 348. In one embodiment, fluid transfer channel 342 extends inside of spike member 346. The spike member 346 extends in a direction substantially parallel with the plurality of vial grip members 338 and serves the purpose of piercing a fluid container such as a vial 90 during assembly of vial adapter 14 to a vial 90 as is shown in greater detail in FIG. 20B.

In one embodiment, a vial sleeve seal 350 is disposed over the spike member 346. The vial sleeve seal 350 provides a seal between vial adapter 14 and a vial 90 with the piercing tip 348 of spike member 346 engaged with the vial 90. In one embodiment, vial sleeve seal 350 comprises a rubber spike sleeve.

Referring to FIGS. 19A-19F, pressure equalization system 314 includes pressure equalization housing 360 and toroidal expandable balloon 362 which includes an expansion chamber 366. Pressure equalization housing 360 defines a tapered exterior wall portion 361 and an interior annular ring cavity portion 363. In one embodiment, tapered exterior wall portion 361 includes a plurality of stabilizing ribs 365. In one embodiment, stabilizing ribs 365 may extend in an axial direction along tapered exterior wall portion 361 of pressure equalization housing 360 and the ribs 365 may be spaced around a periphery of pressure equalization housing 360. Expandable balloon 362 includes a variable volume. Pressure equalization housing 360 comprises a relatively rigid material and expandable balloon 362 comprises a relatively flexible material. In one embodiment, expandable balloon 362 comprises a thin, transparent plastic film that is attached to pressure equalization housing 360 in a gastight manner. In one embodiment, expandable balloon 362 is designed as a bellow which is compressible and extendable and thus the volume of the expansion chamber 366 of expandable balloon 362 can thereby be increased and decreased. In one embodiment, interior annular ring cavity portion 363 of pressure equalization housing 360 extends radially around vial access housing 330 and expandable balloon 362 extends radially around vial access housing 330.

Pressure equalization housing 360 provides a barrier wall member that protects expandable balloon 362 from being torn during engagement of a cannula with a vial, during transfer of a substance from a vial chamber to a barrel chamber via the cannula, and during disengagement of the cannula from the vial. In one embodiment, by having expandable balloon 362 extending radially around the entirety of vial access housing 330, the vial adapter 14 is balanced such that a center of mass is positioned at about a longitudinal axis of vial adapter 14. In one embodiment, expandable balloon 362 extends 360 degrees (360°) radially around vial access housing 330. In one embodiment, a portion of toroidal expandable balloon 362 is not covered by pressure equalization housing 60. In this manner, expandable balloon 362 is capable of expanding in an axial direction.

In one embodiment, pressure equalization housing 360 and vial access housing 330 are a single integral component. In another embodiment, pressure equalization housing 360 and vial access housing 330 are separate components and pressure equalization housing 360 is attachable to vial access housing 330 such that significant relative movement between pressure equalization housing 360 and vial access housing 330 is prevented.

Referring to FIG. 19F, a pressure normalization channel 370 extends from second end 334 of vial access housing 330 to exit aperture 364 of pressure equalization housing 360. Pressure normalization channel 370 is arranged to provide gas communication between the expandable balloon 362 and the interior of a vial 90 when the vial adapter 14 is connected to a vial 90. With vial adapter 14 connected to a vial 90, a syringe or cannula assembly may be used to inject fluid into the vial 90 or to withdraw fluid therefrom as described in more detail below. In one embodiment, pressure normalization channel 370 extends from a portion of piercing tip 348 of spike member 346 and substantially parallel with fluid transfer channel 342 inside spike member 346. The pressure normalization channel 370 diverts in a direction perpendicular to fluid transfer channel 342 substantially at shoulder portion 372 of pressure normalization channel 370. The pressure normalization channel 370 includes an inlet opening 374 arranged substantially at a portion of piercing tip 348 of spike member 346 and an outlet opening 376 positioned substantially at exit aperture 364 of pressure equalization housing 360.

Referring to FIGS. 19A and 19F, in one embodiment, the pressure normalization channel 370 comprises a filter 380 arranged to cover a region of the pressure normalization channel 370. The filter 380 serves the purpose of preventing any fluid from a container, such as a vial, from reaching expansion chamber 366 of expandable balloon 362. In one embodiment, the filter 380 is preferably a hydrophobic filter which permits gas to pass, but prevents liquid to pass. The filter 380 may be secured within pressure equalization housing 360 via filter holder 382.

In one embodiment, vial adapter 14 may also include a valve arrangement positioned in the proximity of outlet opening 376 of the pressure normalization channel 370. Such a valve arrangement prevents clogging of the filter 380 by providing a cracking pressure to the valve arrangement for the fluid which flows in a direction from the inlet opening 374 to the outlet opening 376 of the pressure normalization channel 370 while permitting preferably a minimal cracking pressure in the opposite direction.

The function and advantages of vial adapter 14, according to the present disclosure, will be described in greater detail. When preparing and administering drugs, care has be taken to minimize, or preferably eliminate, the risk of exposing people, such as medical and pharmacological personnel, to toxic substances. Some drugs must be dissolved or diluted before they are administered, which involves transferring a solvent from one container to a sealed vial containing the drug in powder or liquid form, by means of a needle, for example. Drugs may be inadvertently released into the atmosphere in gas form or by way of aerosolization, during the withdrawal of the needle from the vial, and while the needle is inside the vial, if any pressure differential between the interior of the vial and surrounding atmosphere exists. Vial adapter 14 of the present disclosure eliminates this problem by using pressure equalization system 314 of vial adapter 14 that may be attached to a vial during the preparation of drugs. The pressure equalization system 314 includes an expandable balloon 362 which in communication with the interior of the vial 90 ensures that neither an increased pressure nor a vacuum can occur inside the vial 90 when gas or liquid is injected into or withdrawn from the vial 90. In one embodiment, the expandable balloon 362 may be filled with cleaned or sterilized air prior to its use to ensure that the contents of the vial 90 do not become contaminated with air-borne particles such as dust, pollen, mold or bacteria, or other undesirable substances.

Referring to FIGS. 22-25, the vial adapter 14 is assembled via its connection element 336 of vial access housing 330 to a cannula 20 of injector adapter 12 which in turn can be connected to a fluid container, such as barrel assembly 16, and the vial adapter 14 is also assembled via its vial connection members 337 with a second fluid container, such as a vial 90. As vial adapter 14 is assembled with the vial 90, the piercing tip 348 of the spike member 346 is pierced through a septum 94 of the vial 90. Vial 90 may be a standard drug vial of any type having an open head portion covered by a pierceable septum of an elastomeric material. The walls 95 of vial 90 define a vial chamber 96 for containing a substance 98. The vial septum 94 is engaged with the head portion 93 of vial 90 to seal a substance within vial chamber 96. The plurality of vial grip members 338 fixedly connect vial adapter 14 to the vial 90 as the hook protrusions 340 of vial grip members 338 engage the corresponding flange 97 on vial 90 as shown in FIG. 20B. After assembly, a user is able to insert fluid into the vial 90, or optionally to retract fluid from the vial 90.

Figure 21A:
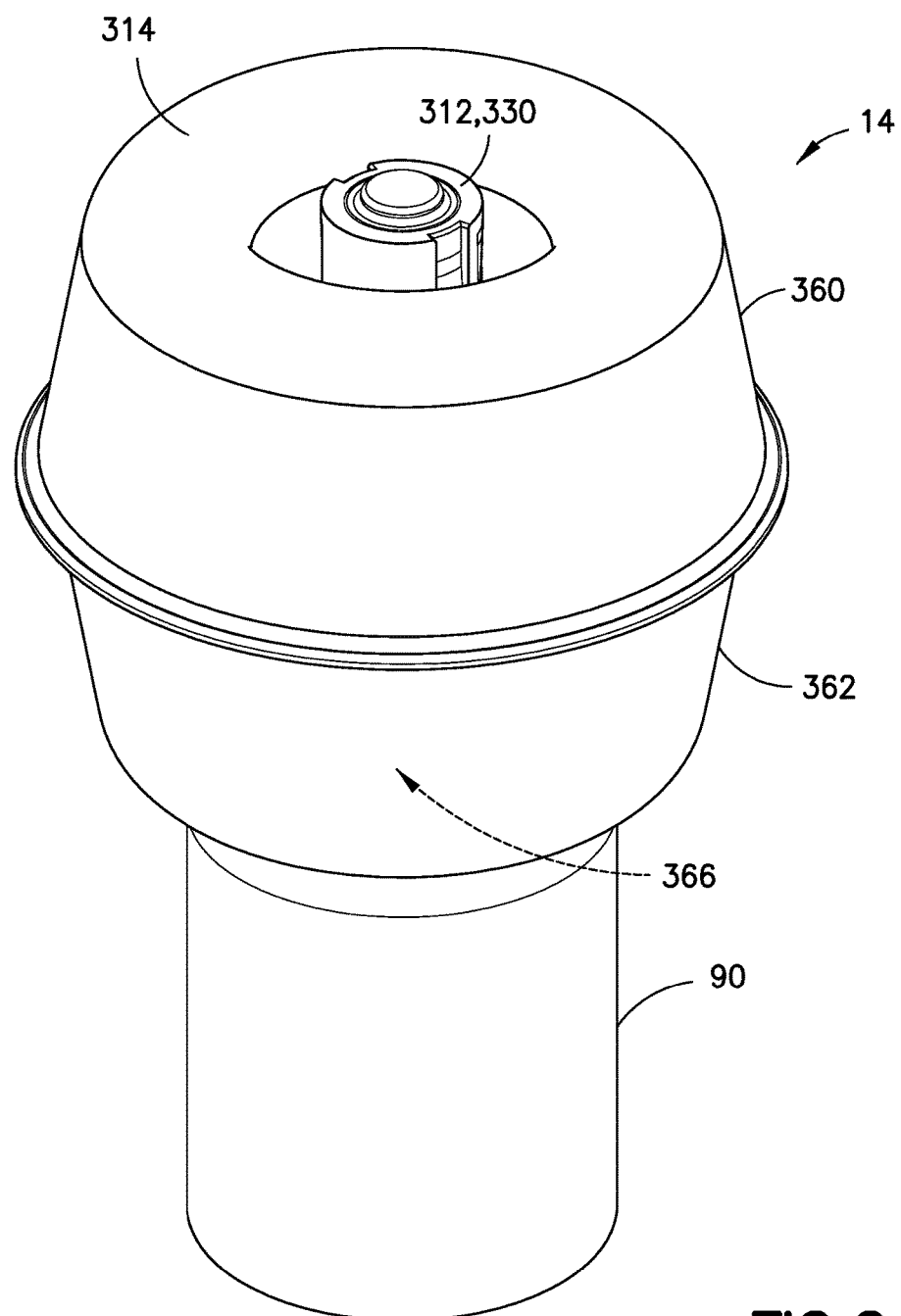
FIG. 21A is a perspective view of a vial adapter connected to a vial in accordance with an embodiment of the present invention.
Figure 21B:
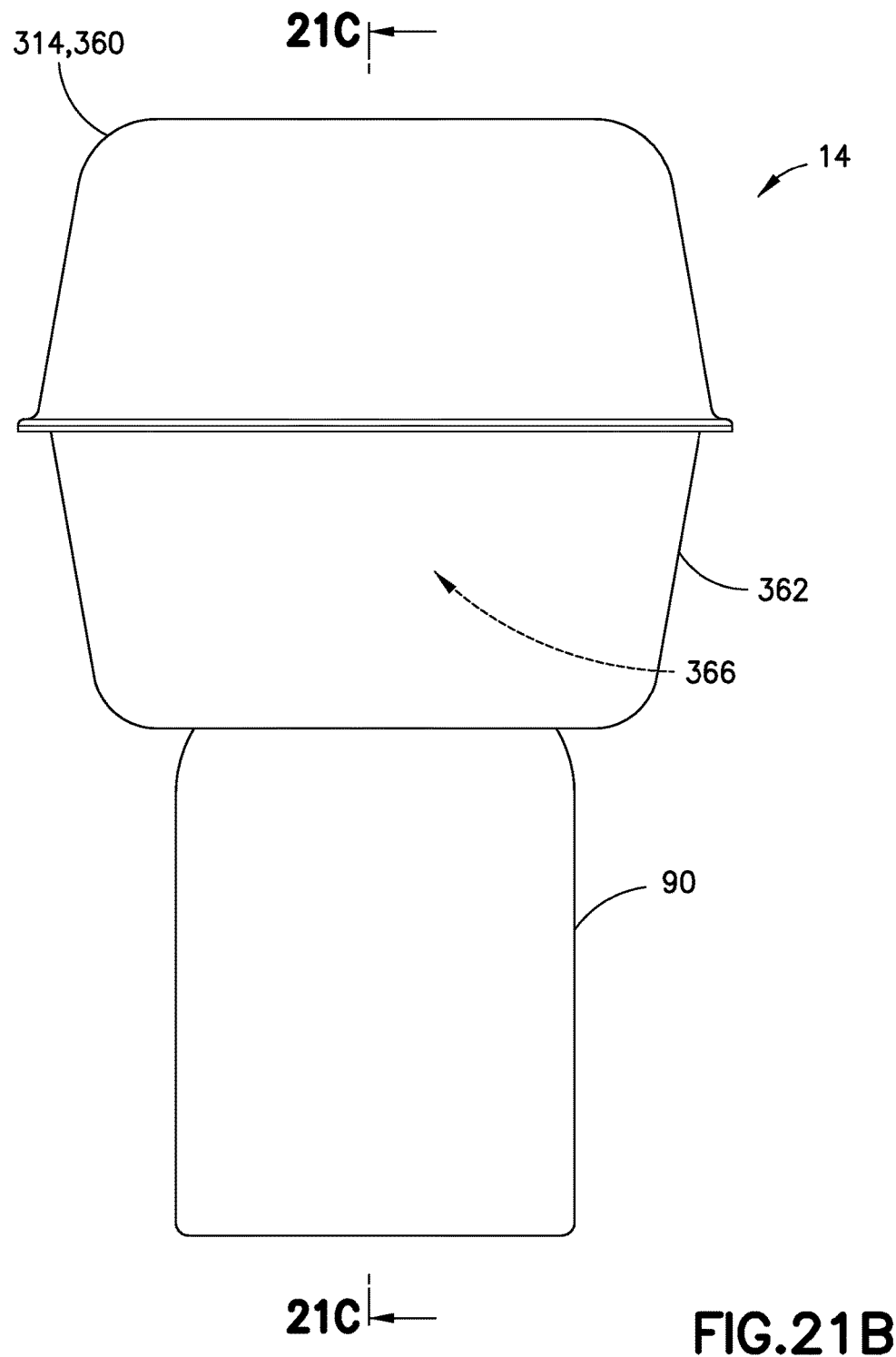
FIG. 21B is another perspective view of a vial adapter connected to a vial in accordance with an embodiment of the present invention.
Figure 21C:
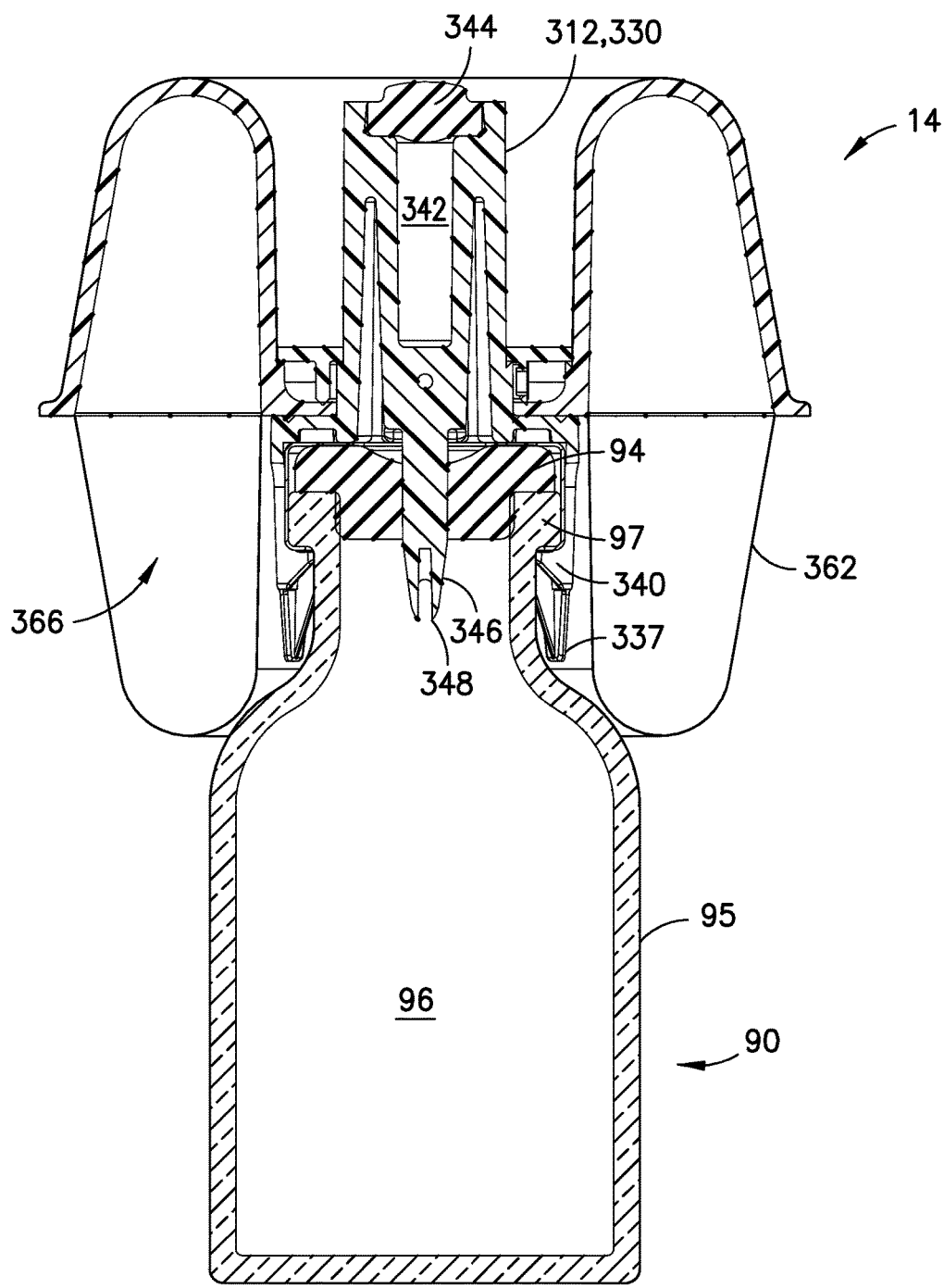
FIG. 21C is a cross-sectional view of a vial adapter connected to a vial taken along line 21C-21C of FIG. 21B in accordance with an embodiment of the present invention.
Figure 22:
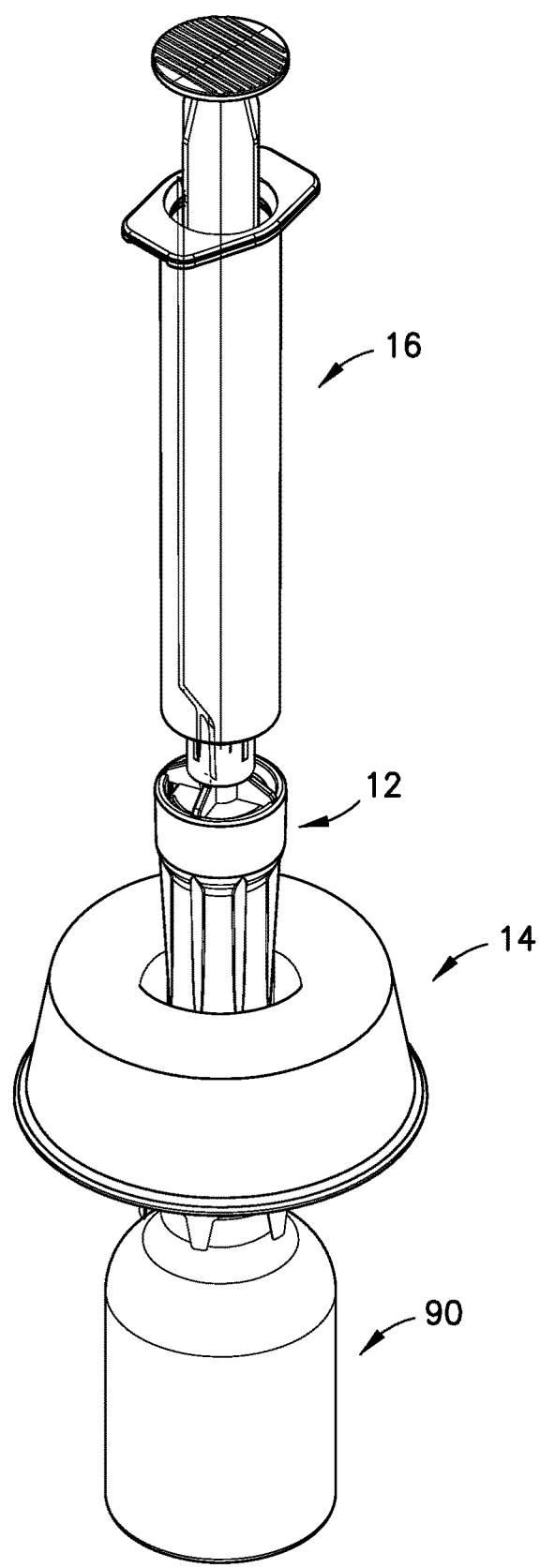
FIG. 22 is an assembled, perspective view of a system in accordance with an embodiment of the present invention.

As a fluid is inserted into the vial 90, using the cannula 20 and barrel assembly 16, an overpressure is created inside the vial 90. Pressure equalization system 314 of vial adapter 14 permits pressure equalization between the vial 90 and the expandable balloon 362. The pressure normalization channel 370 normalizes the pressure inside the vial 90 by relieving the pressure inside the vial 90 to the expansion chamber 366 of the expandable balloon 362 as shown in FIGS. 21A-21C.

In other words, FIGS. 22-25 and 21A-21C show the vial adapter 14 attached to the vial 90 and with cannula 20 inserted through the vial adapter 14 and into the interior of the vial 90. As a fluid is injected into the vial 90, or withdrawn from the vial 90, the pressure normalization channel 370 of the pressure equalization system 314 of vial adapter 14 permits gas to flow from the interior of the vial 90 into the expandable balloon 362 or from the expansion chamber 366 of the expandable balloon 362 to the vial 90, and thereby equalizes the pressure in the interior of the vial 90. Gas may enter the expandable balloon 362 via outlet opening 376, however gas cannot exit from the expandable balloon 362. This eliminates, or at least reduces the risk of any substance inside the vial 90 from being released into the atmosphere in gas form or by way of aerosolization during the insertion or withdrawal of a needle from the vial 90 or while a needle is inserted in the vial 90. It also eliminates, or reduces the risk of the vial 90 deforming due to the increased pressure inside the vial 90, whereby such deformation may cause leakage of the vial's 90 contents due to separation of the septum 94 of the vial 90 from the walls 95 of the vial 90, for example.

Referring to FIGS. 1-11C, the use of a connection system of the present disclosure to connect a first medical device component, e.g., injector adapter 12, to a second medical device component, e.g., IV line adapter 18, will now be described.

Figure 2:
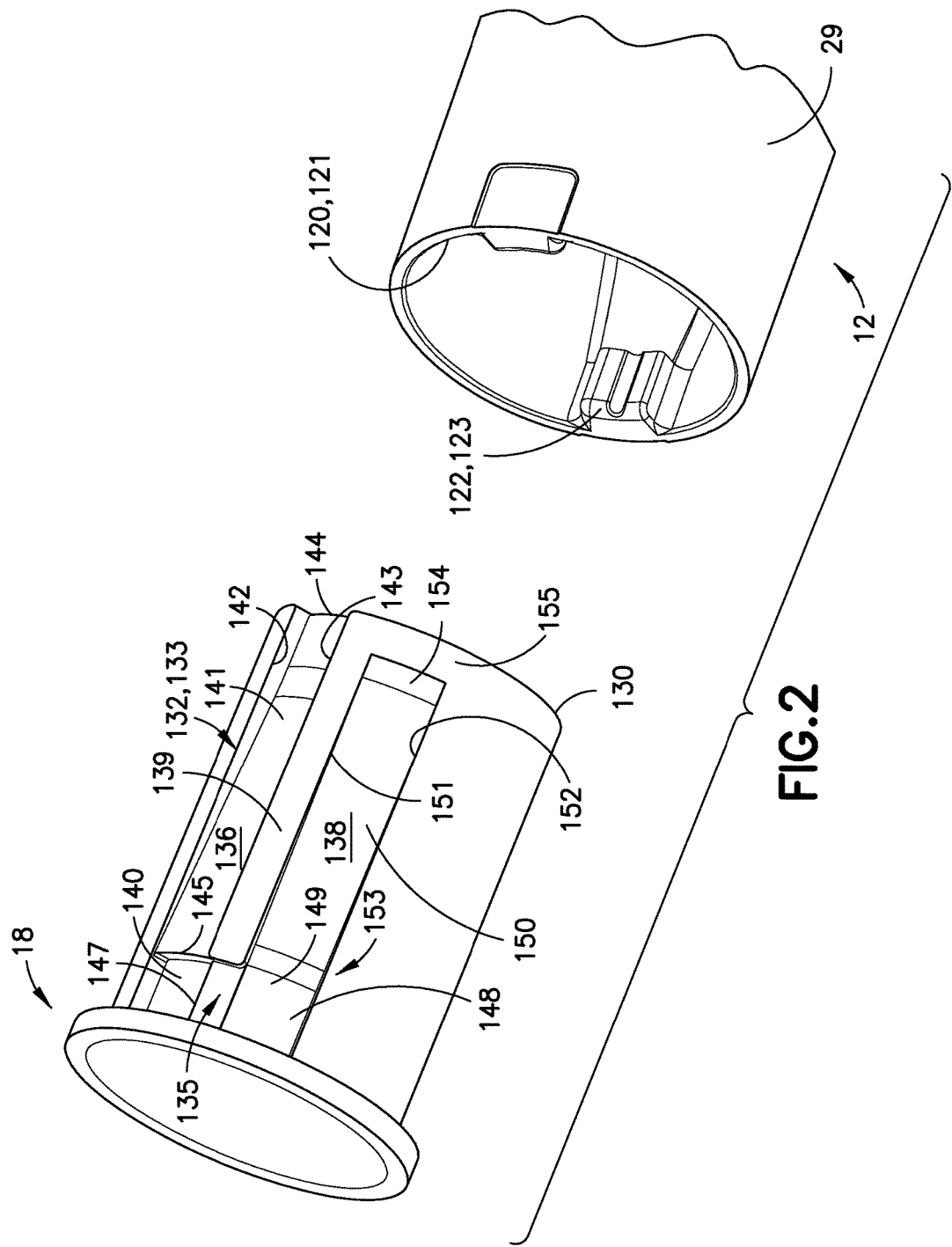
FIG. 2 is a detailed, fragmentary view of a portion of the first medical device component and a portion of the second medical device component of FIG. 1 including a connection system in accordance with an embodiment of the present invention.
Figure 5A:
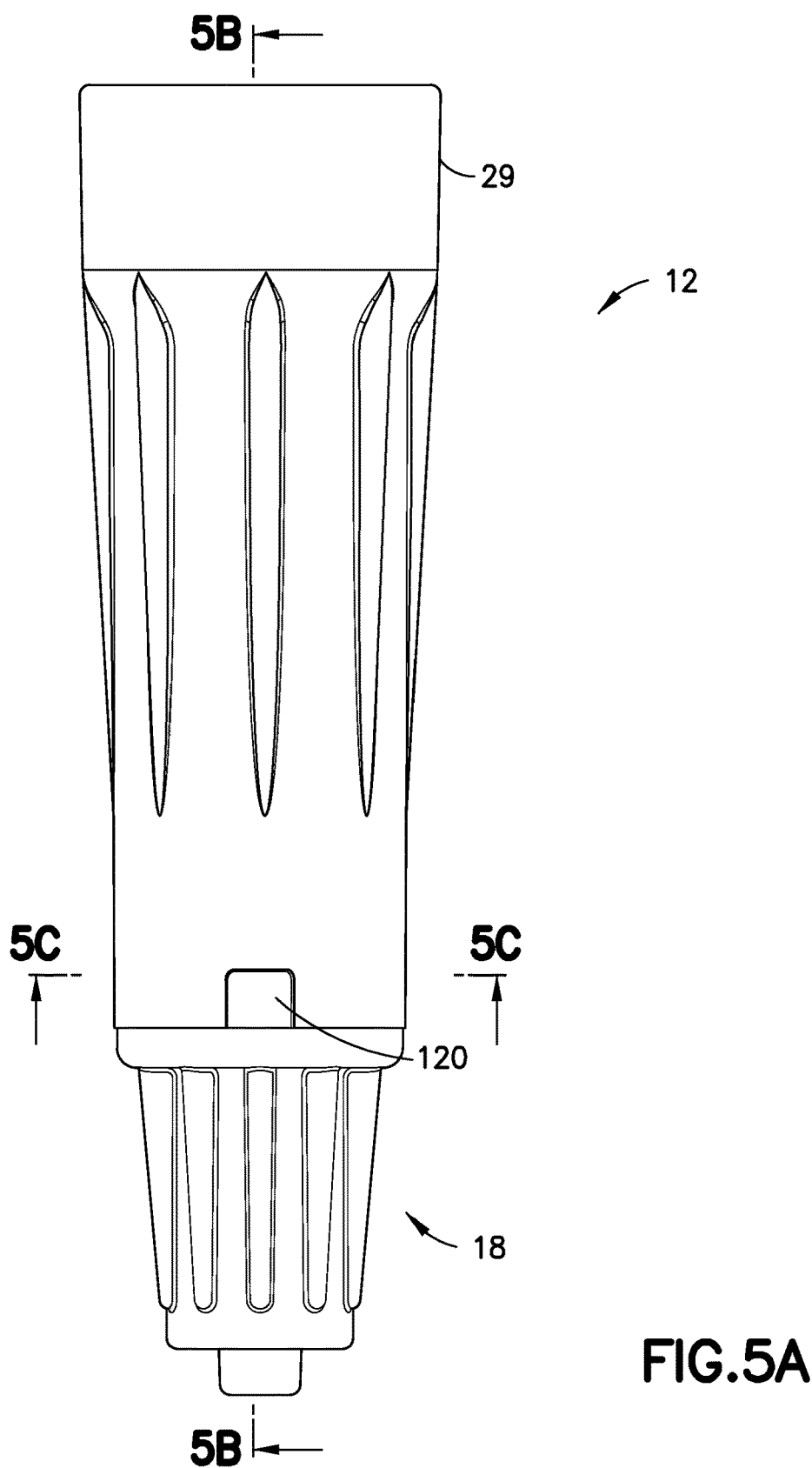
FIG. 5A is a perspective view of a first medical device component connected to a second medical device component by a connection system in accordance with an embodiment of the present invention.

Initially, the first connection element 120 of injector adapter 12 is aligned with the first connection path 136 of IV line adapter 18 and the second connection element 122 of injector adapter 12 is aligned with the second connection path 170 of IV line adapter 18 as shown in FIGS. 1, 2, and 9A. Next, a user can push injector adapter 12 and IV line adapter 18 together so that first connection element 120 of injector adapter 12 enters first connection path 136 of IV line adapter 18 and second connection element 122 of injector adapter 12 enters second connection path 170 of IV line adapter 18. The path that connection elements 120, 122 of injector adapter 12 follow, through respective connection paths 136, 170 of IV line adapter 18, is shown in the connection illustration of FIG. 3. As connection elements 120, 122 of injector adapter 12 are guided through respective connection paths 136, 170 of IV line adapter 18 from respective entry portions 144, 183 to respective exit portions 145, 184 in a direction generally along arrow A (FIG. 3), connection elements 120, 122 are compressed via the upwardly tapering guide surface 141, 180. In this manner, when connection elements 120, 122 reach the respective exit portions 145, 184, connection elements 120, 122 are elastically deformed such that connection elements 120, 122 snap into respective locking recesses or securement elements 140, 172 as shown in FIGS. 5A-5C. In this manner, as connection elements 120, 122 are elastically deformed such that connection elements 120, 122 snap into respective locking recesses or securement elements 140, 172, connection elements 120, 122 make an audible snapping or clicking sound that enables a user to be informed that a secure connection has been made. In other words, once connection elements 120, 122 slide over and past respective exit portions 145, 184 of tapered guide surfaces 141, 180, elastic connection elements 120, 122 snap back or return to their undeformed position and lock within respective securement elements 140, 172, i.e., with connection elements 120, 122 mechanically locked within respective securement elements 140, 172, injector adapter 12 is connected to IV line adapter 18, such that, significant relative movement between injector adapter 12 and IV line adapter 18 is prevented.

The locked position of FIG. 4 illustrates the elastically deformable connection elements 120, 122 of injector adapter 12 in a locked position in which connection elements 120, 122 are in their undeformed position and are locked within respective securement elements 140, 172. The unlocked position of FIG. 4 illustrates the elastically deformable connection elements 120, 122 of injector adapter 12 in a deformed position in which connection elements 120, 122 are deformed as they travel through the respective upwardly tapering guide surfaces 141, 180 of IV line adapter 18.

Figure 3:
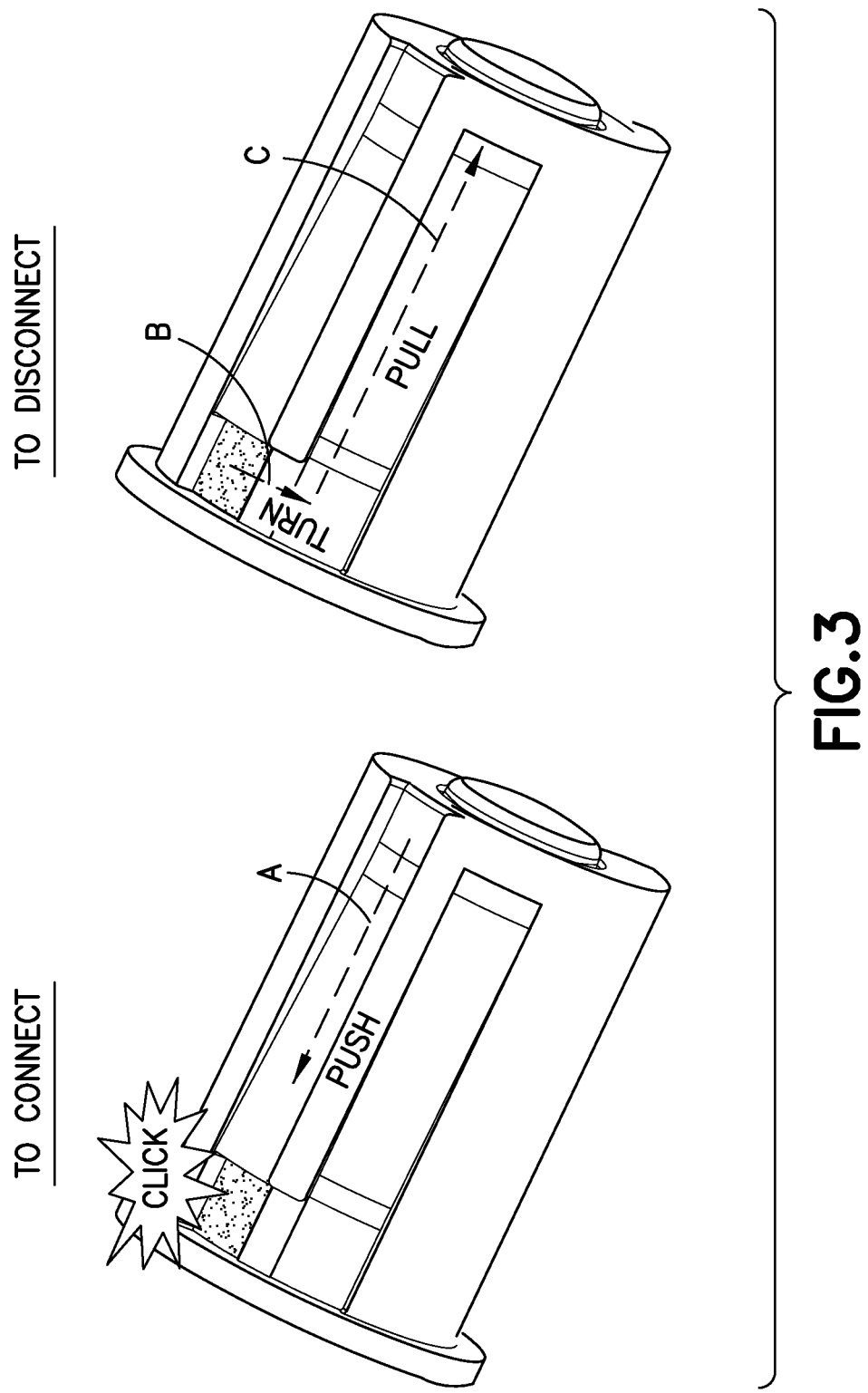
FIG. 3 is a perspective view of a portion of a connection system of the present disclosure illustrating a connection path that is distinct from a disconnection path in accordance with an embodiment of the present invention.
Figure 6A:
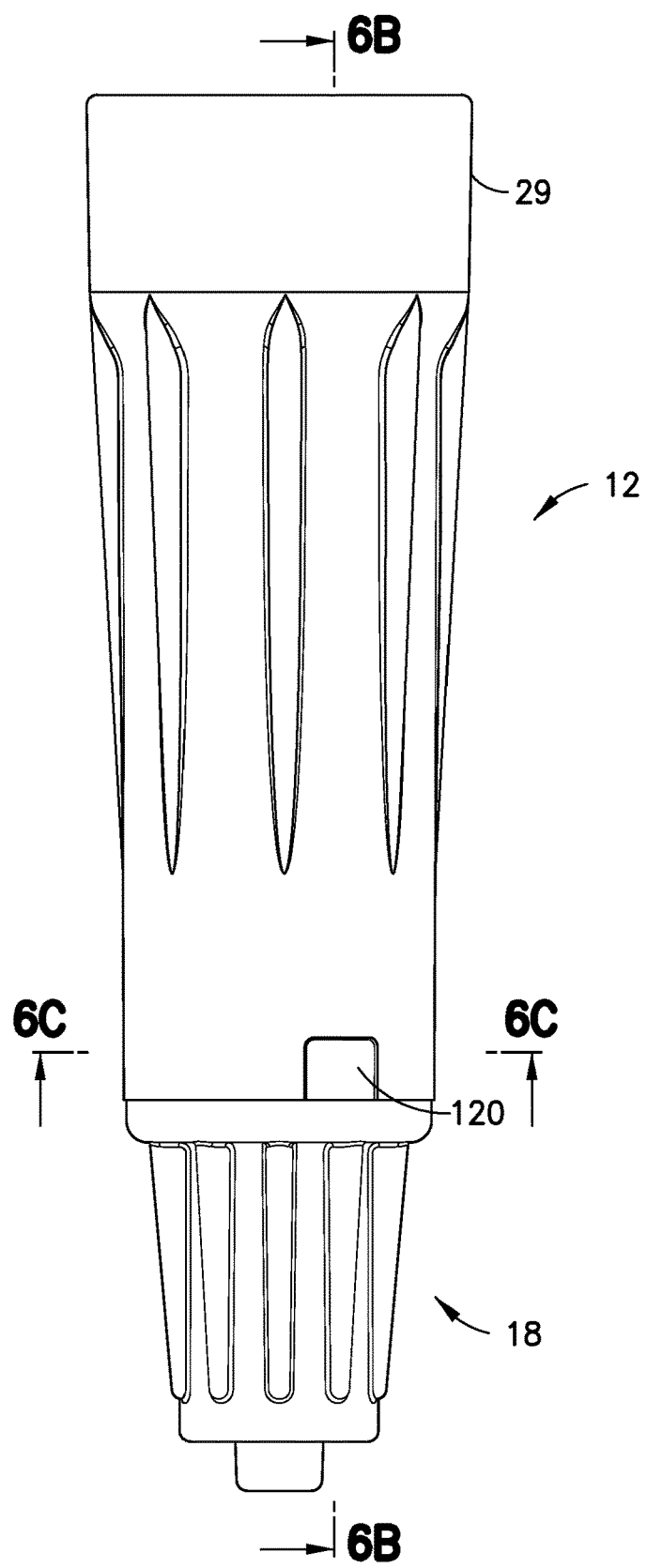
FIG. 6A is a perspective view of a first medical device component connected to a second medical device component by a connection system in accordance with an embodiment of the present invention.
Figure 7:
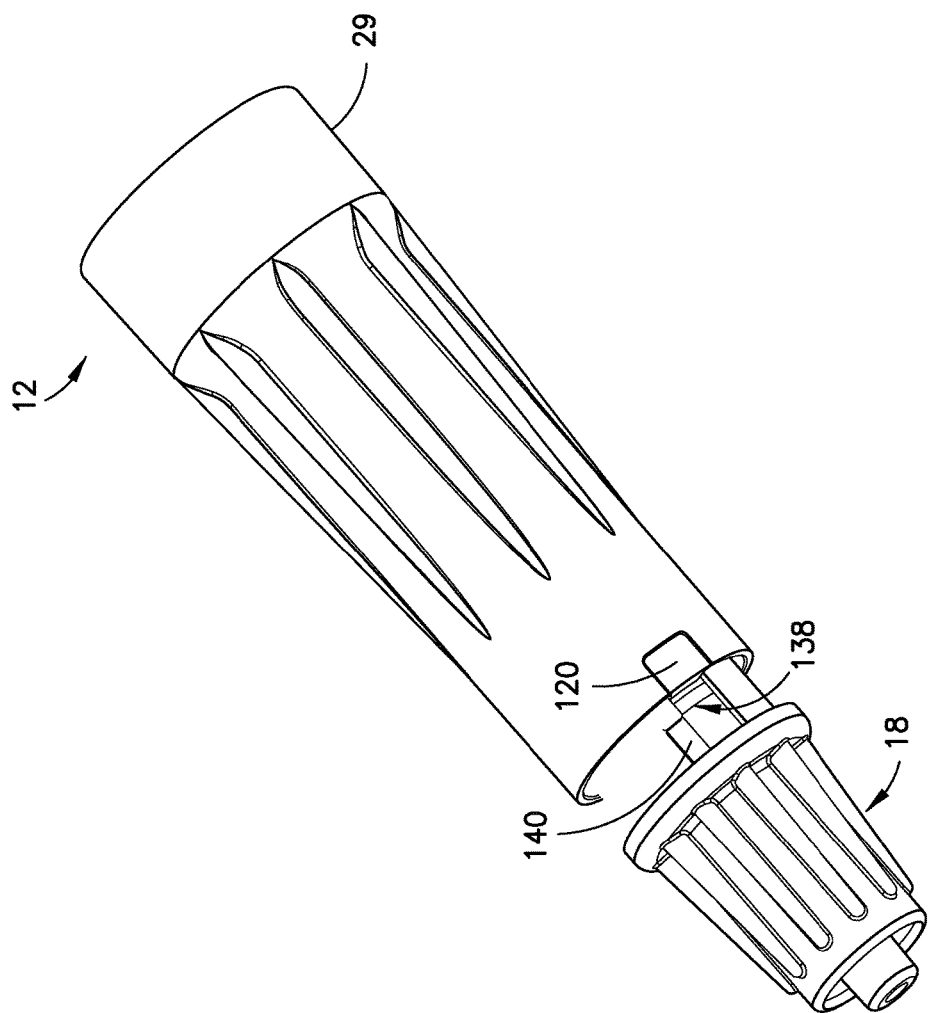
FIG. 7 is a perspective, cross-sectional view of a first medical device component connected to a second medical device component by a connection system in accordance with an embodiment of the present invention.
Figure 8A:
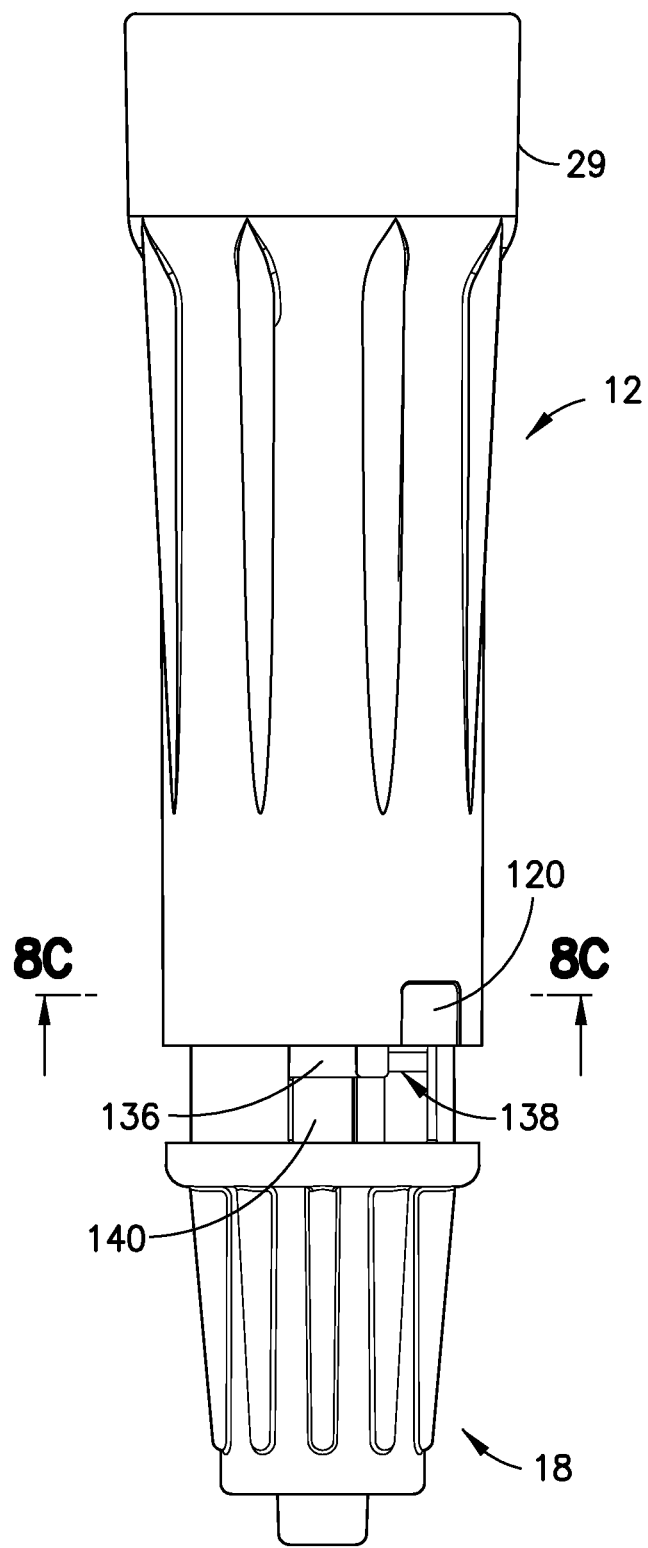
FIG. 8A is a perspective view of a first medical device component connected to a second medical device component by a connection system in accordance with an embodiment of the present invention.
Figure 10:
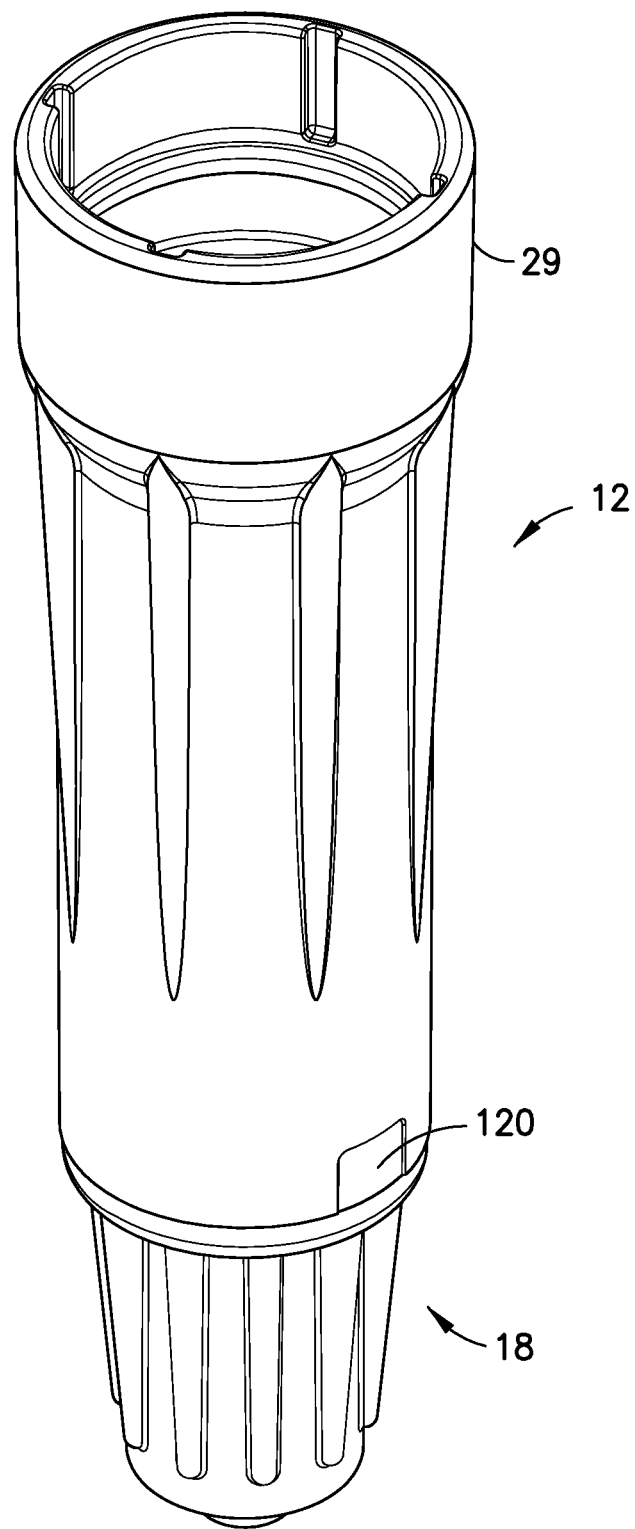
FIG. 10 is a perspective view of a first medical device component connected to a second medical device component by a connection system in accordance with an embodiment of the present invention.

Referring to FIG. 3, once it is desired to disconnect injector adapter 12 from IV line adapter 18, connection elements 120, 122 of injector adapter 12 can be rotated in a counter-clockwise direction generally along arrow B to rotate connection elements 120, 122 out of engagement with respective securement elements 140, 172. Step members 135, 173 provide a component that allows connection elements 120, 122 of injector adapter 12 to be rotated out from engagement with respective securement elements 140, 172. For example, as a rotational force is exerted on connection elements 120, 122 to move connection elements 120, 122 in a direction generally along arrow B to move connection elements 120, 122 out of securement elements 140, 172, connection elements 120, 122 cooperate with a respective tapered exit recess step 147, 191 of IV line adapter 18. The respective tapered exit recess steps 147, 191 of IV line adapter 18 provide a ramp surface to deform respective connection elements 120, 122 outwardly until connection elements 120, 122 advance beyond, i.e., slide over and past, respective top step surfaces 149, 193 of step members 135, 173 as shown in FIGS. 6A-6C. Once connection elements 120, 122 slide over and past respective top step surfaces 149, 193 of step members 135, 173, connection elements 120, 122 snap into respective entry portions 153, 188 of disconnection paths 138, 171. In this manner, as connection elements 120, 122 are elastically deformed such that connection elements 120, 122 snap into respective entry portions 153, 188 of disconnection paths 138, 171, connection elements 120, 122 make an audible snapping or clicking sound that enables a user to be informed that a disconnection has been made. As connection elements 120, 122 snap into respective entry portions 153, 188 of disconnection paths 138, 171, connection elements 120, 122 return to their undeformed or original position within respective entry portions 153, 188 of disconnection paths 138, 171. Also, step members 135, 173 can be used to tune resistance and provide tactile feel during a disconnection movement.

With connection elements 120, 122 in respective disconnection paths 138, 171 of IV line adapter 18, a pulling force may be exerted in a direction generally along arrow C (FIG. 3) to pull injector adapter 12 out from IV line adapter 18. As connection elements 120, 122 of injector adapter 12 are guided through respective disconnection paths 138, 171 of IV line adapter 18 from respective entry portions 153, 188 to respective exit portions 154, 189 in a direction generally along arrow C (FIG. 3), connection elements 120, 122 are compressed via the upwardly tapering guide surfaces 150, 185. To prevent injector adapter 12 from being easily removed from IV line adapter 18, barrier exit walls 155, 190 provide a physical barrier to prevent respective connection elements 120, 122 from being easily removed from disconnection paths 138, 171. Once a force is exerted to deform connection elements 120, 122 so they slide over and past respective barrier exit walls 155, 190, connection elements 120, 122 return to their undeformed or original position past barrier exit walls 155, 190 and injector adapter 12 is removed from IV line adapter 18 as shown in FIG. 1.

The connection system of the present disclosure provides for quick and intuitive coupling and decoupling of two opposing medical device components through the use of a connection path and a disconnection path, the connection path being distinct from the disconnection path. Furthermore, the connection system of the present disclosure provides audible and tactile connection feedback through the use of elastically deformable connection elements.

Figure 11B:
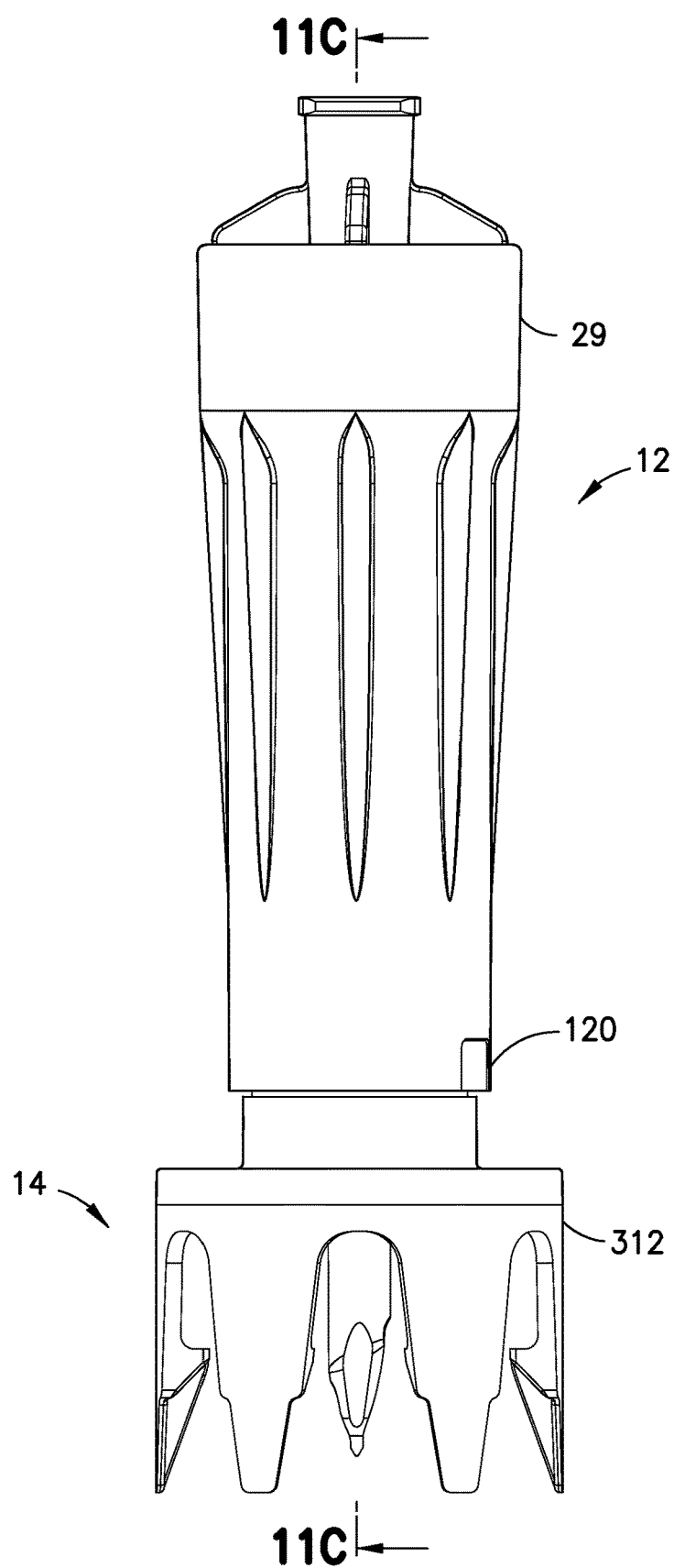
FIG. 11B is a side elevation view of a first medical device component connected to a second medical device component by a connection system in accordance with an embodiment of the present invention.
Figure 11C:
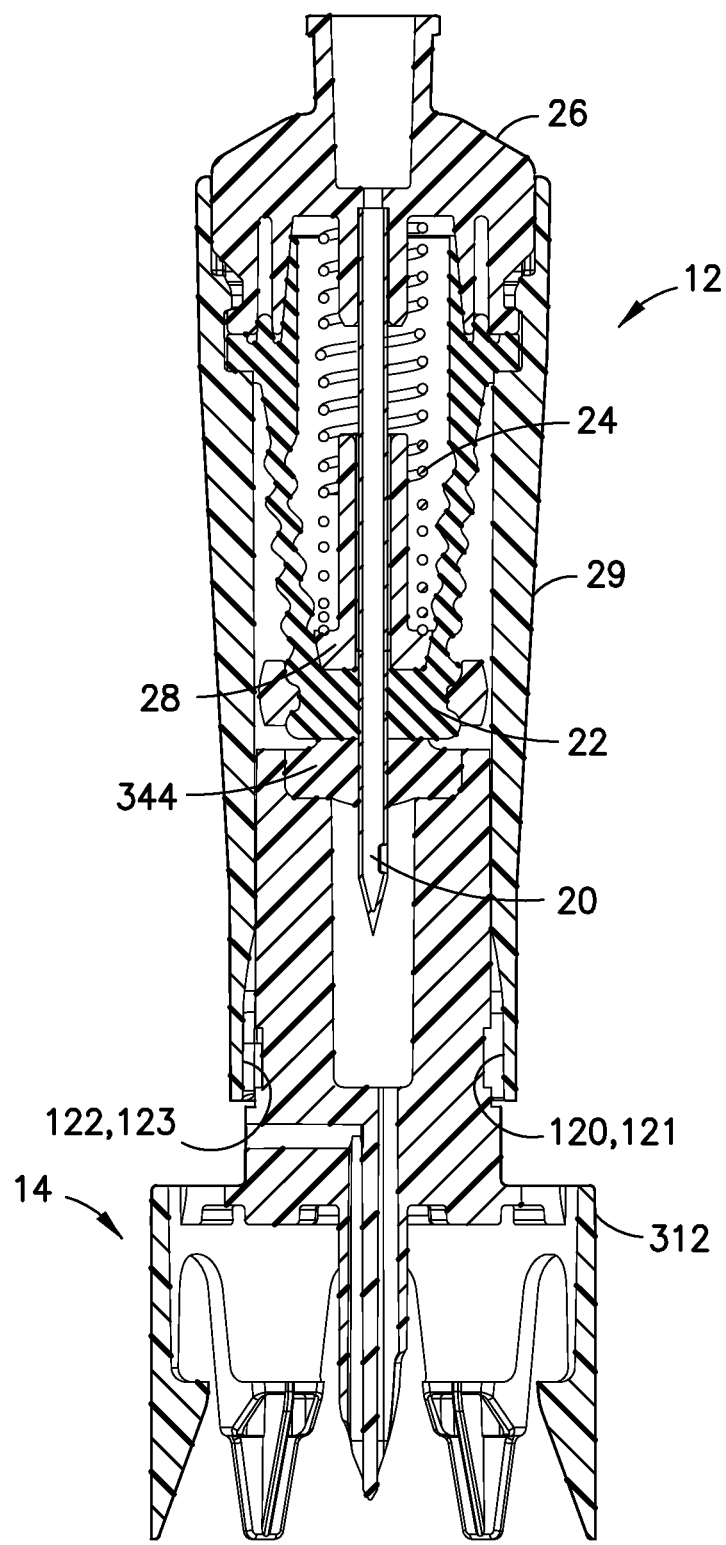
FIG. 11C is a cross-sectional view of the first medical device component connected to the second medical device component taken along line 11C-11C of FIG. 11B in accordance with an embodiment of the present invention.

FIGS. 11A-11C illustrate the use of a connection system of the present disclosure to connect injector adapter 12 to vial adapter 14. As previously discussed, the connection system of first and second connection elements 336, 339 of vial adapter 14, illustrated in FIGS. 19A-19G, include similar components to the connection system of first connection element 133 and second connection element 134 of IV line adapter 18 illustrated in FIGS. 12-14B, and the similar components are denoted by a reference number followed by the letter A. For the sake of brevity, the similar steps of the use of a connection system of the present disclosure to connect injector adapter 12 to vial adapter 14 will not be described in detail as the steps are the same as described above to connect injector adapter 12 to IV line adapter 18.

Figure 27:
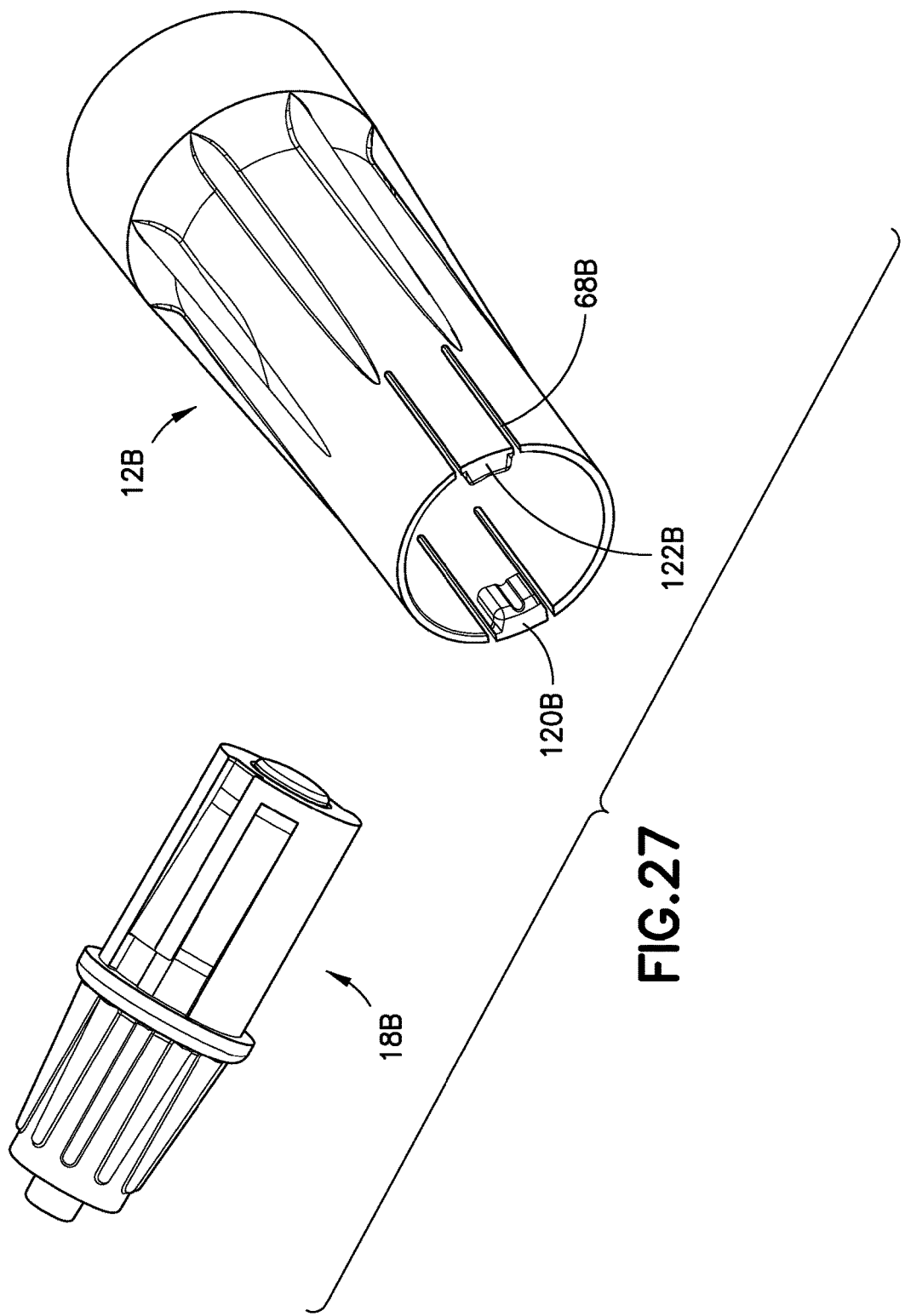
FIG. 27 is an exploded, perspective view of a first medical device component and a second medical device component including a connection system in accordance with another embodiment of the present invention.
Figure 28:
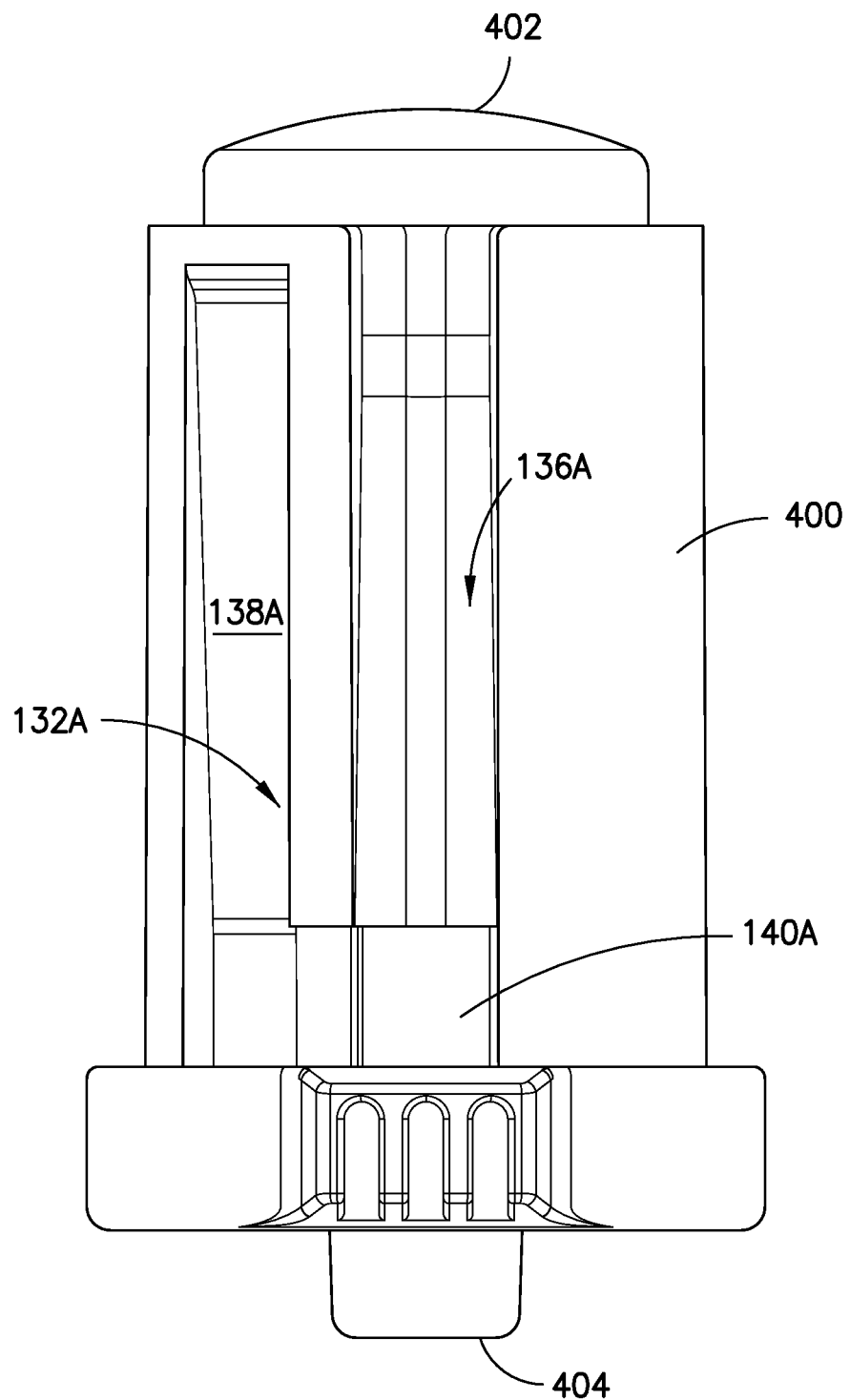
FIG. 28 is a perspective view of a connection system in accordance with another embodiment of the present invention.

FIG. 27 illustrates a further exemplary embodiment of an IV line adapter 18B and an injector adapter 12B. In one embodiment, injector adapter 12B includes slits 68B on opposing sides of connection elements 120B, 122B.

FIGS. 28-35 illustrate another exemplary embodiment. The embodiment illustrated in FIGS. 28-35 includes similar components to the embodiment illustrated in FIGS. 1-26, and the similar components are denoted by a reference number followed by the letter A. For the sake of brevity, these similar components and the similar steps of using connection system 132A (FIGS. 28-35) will not all be discussed in conjunction with the embodiment illustrated in FIGS. 28-35.

Referring to FIGS. 28-35, in one embodiment, connection system 132A includes a connector 400, a membrane 402, and a first luer component 404 which are compatible with a second luer component 406 and an IV line 408 as will be discussed in more detail below.

Referring to FIGS. 28-31, connector 400 includes first end 410, opposing second end 412, and annular protrusion 414. In one embodiment, connector 400 comprises an IV line adapter connector component. Connector 400 provides a compact and accessible connector for connecting a cartridge or barrel containing a reconstituted drug to an intravenous line or an injection apparatus for administering a drug to a patient. First end 410 of connector 400 includes a first connection element 133A of connection system 132A. First connection element 133A of connector 400 forms a portion of a connection system of the present disclosure which is compatible with a connection system 120, 122 of injector adapter 12 which forms another portion of a connection system of the present disclosure as discussed above.

Figure 30:
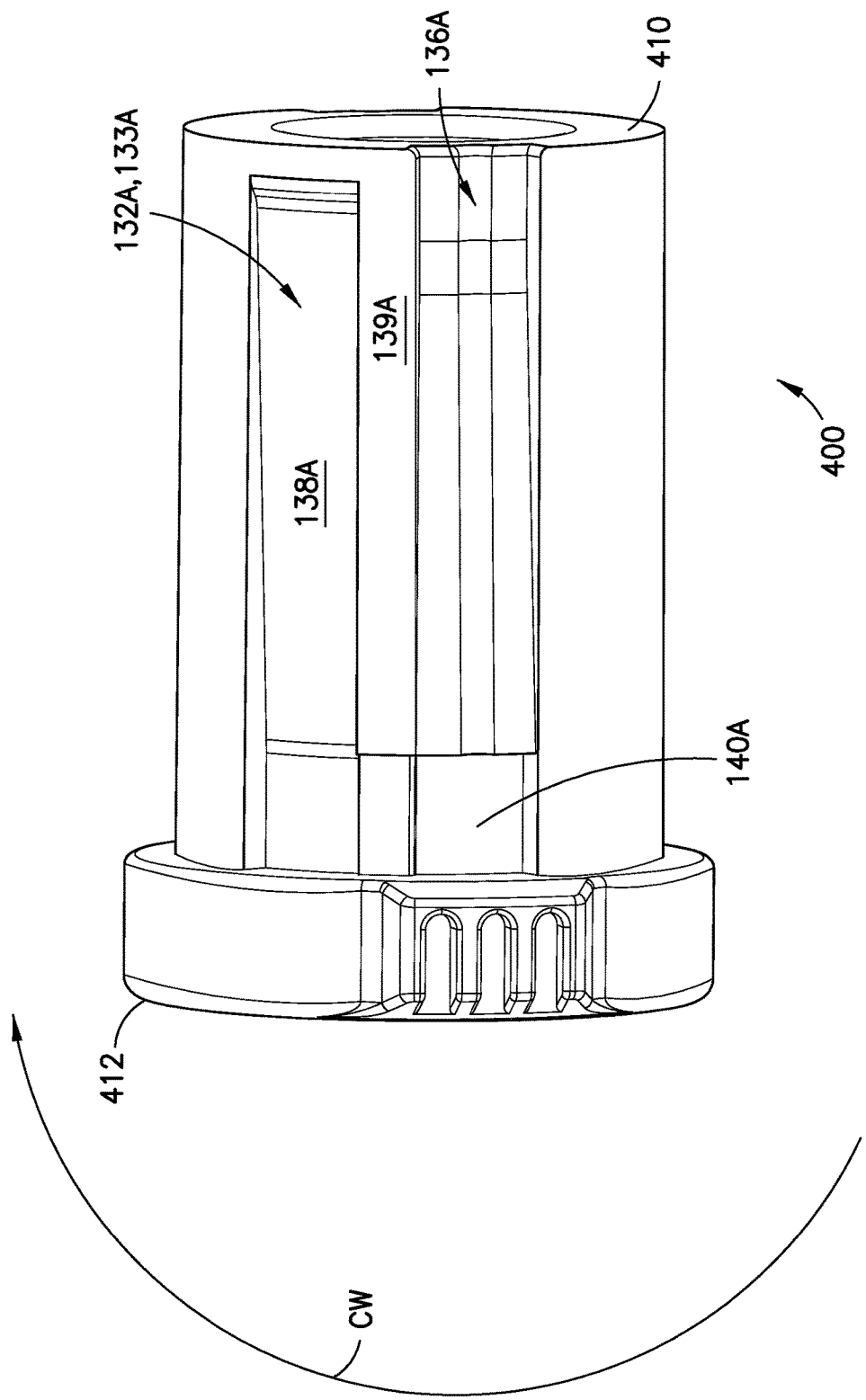
FIG. 30 is a perspective view of a connector in accordance with another embodiment of the present invention.
Figure 31:
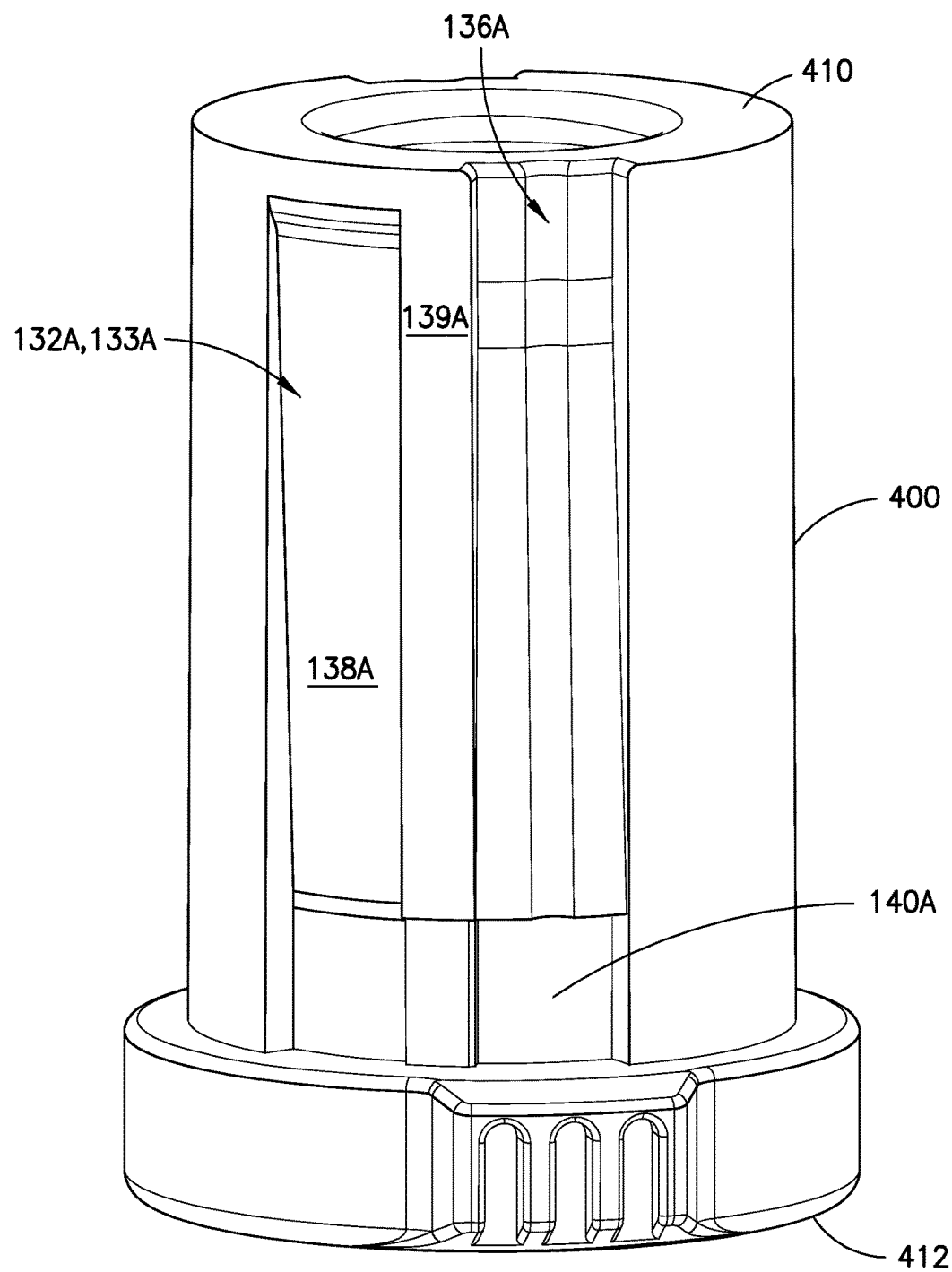
FIG. 31 is a side, perspective view of a connector in accordance with another embodiment of the present invention.

Referring to FIG. 30, first connection element 133A of connector 400 includes a first connection path 136A, a first disconnection path 138A, and a first securement element 140A disposed between the first connection path 136A and first disconnection path 138A. In one embodiment, first connection path 136A, first disconnection path 138A, and first securement element 140A together generally define a U-shaped path. First connection path 136A is distinct from first disconnection path 138A. In this manner, the distinct connection and disconnection paths allow for the fine tuning of tactile and audible responses separately for connection and disconnection movements as described in detail above. In one embodiment, divider wall 139A is disposed between first connection path 136A and first disconnection path 138A. Referring to FIG. 30, connection system 132A of connector 400 includes first disconnection path 138A that is located on an opposite side of first connection path 136A relative to the embodiment illustrated in FIG. 2. In this manner, connection system 132A of connector 400 requires an injector, such as injector adapter 12, to be rotated in a clockwise direction to disconnect the injector from connector 400. In this manner, during the disconnecting step, an overall connector tightening to an IV line results during the use of connection system 132A as will be described in more detail below.

Figure 29:
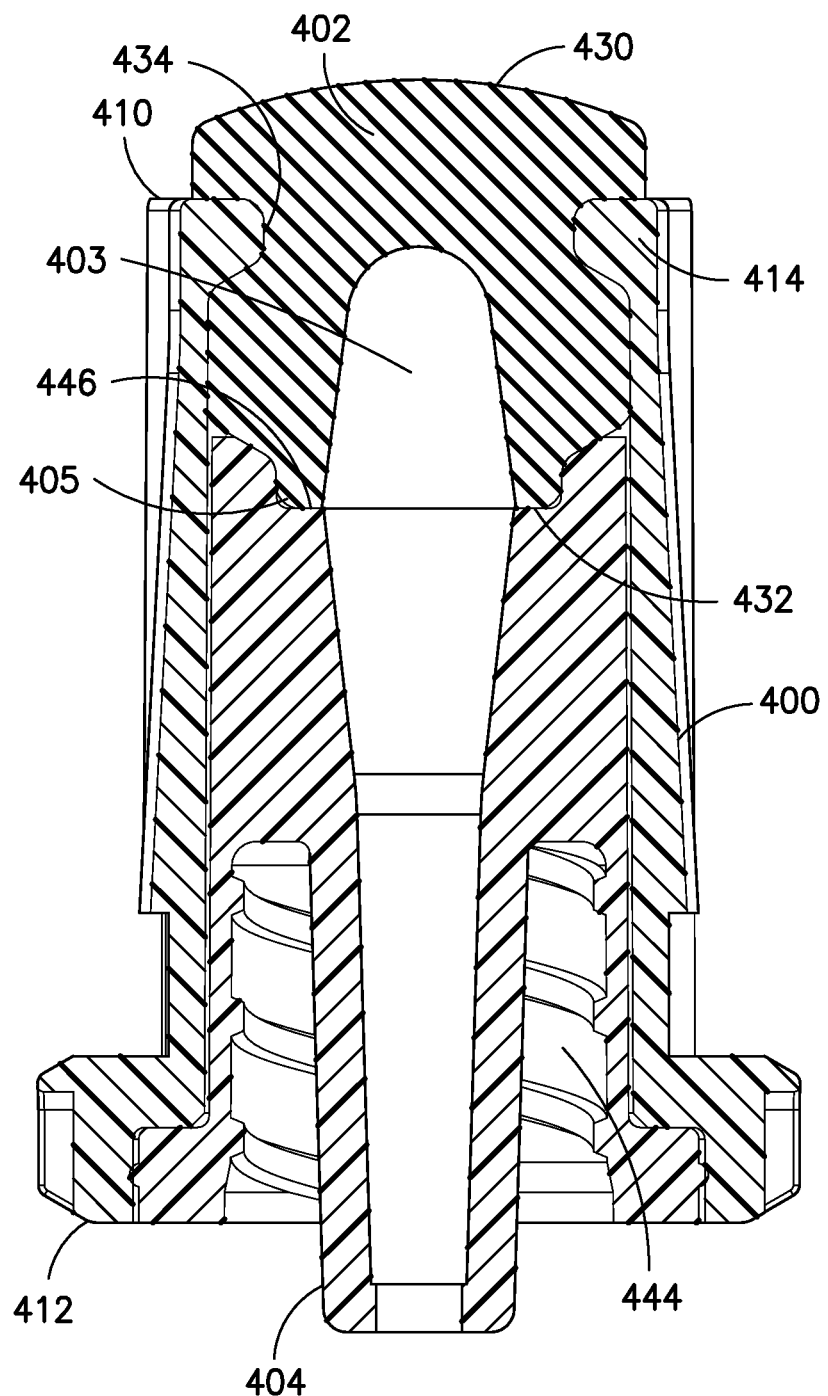
FIG. 29 is a cross-sectional view of the system of FIG. 28 in accordance with another embodiment of the present invention.
Figure 32:
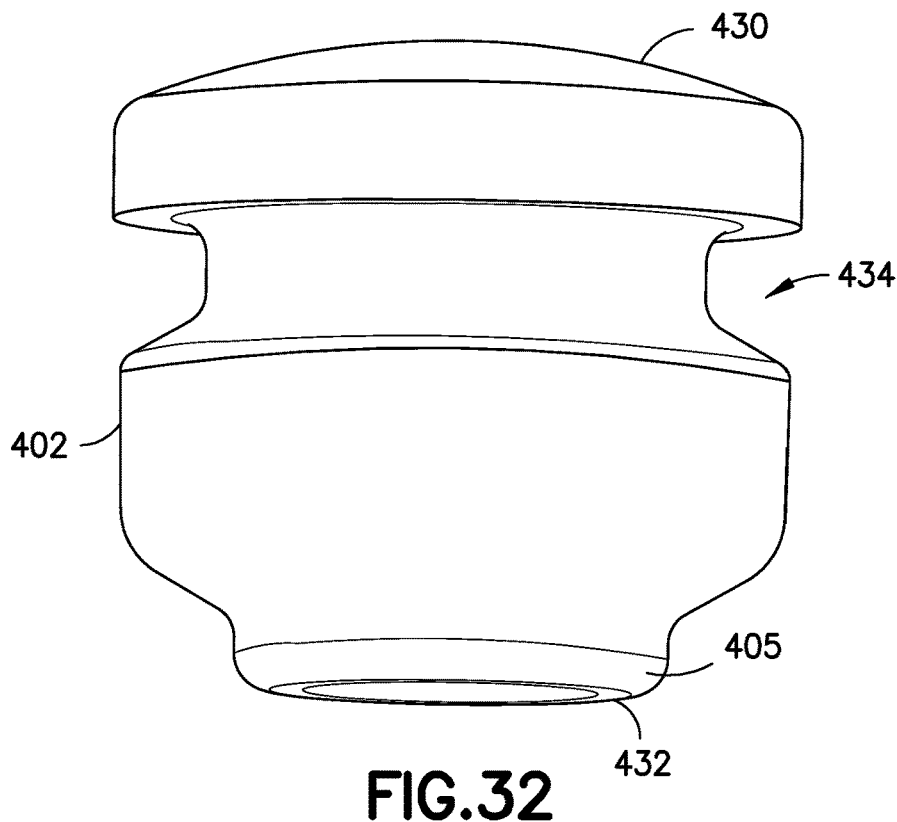
FIG. 32 is a perspective view of a membrane in accordance with another embodiment of the present invention.
Figure 33:
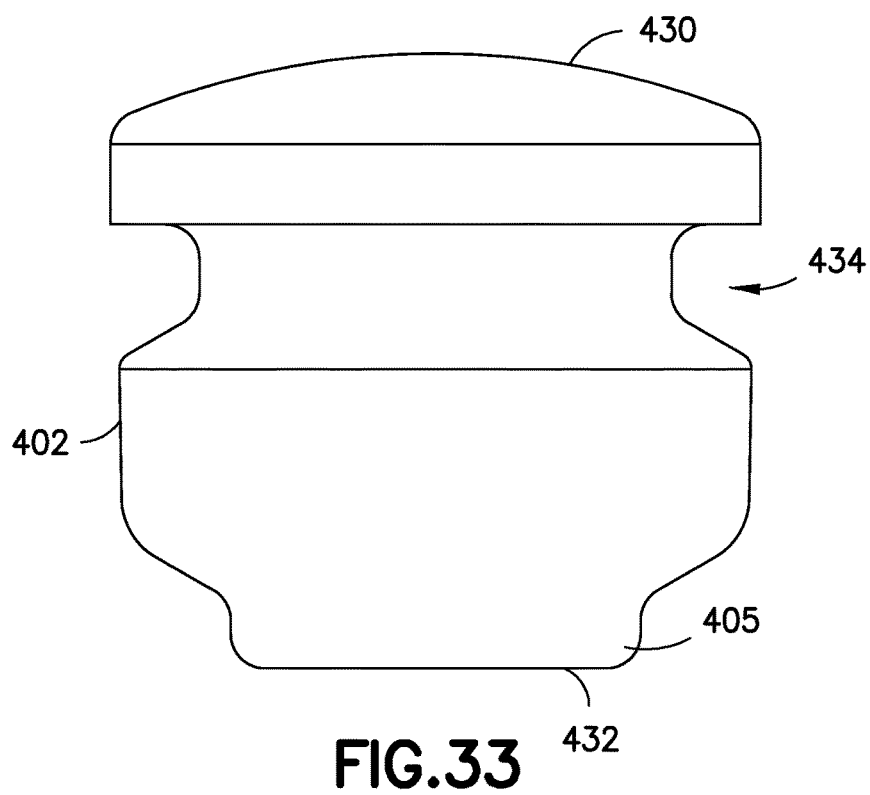
FIG. 33 is a side elevation view of a membrane in accordance with another embodiment of the present invention.

Referring to FIGS. 29, 32, and 33, in one embodiment, system 132A includes a pierceable barrier membrane 402. Membrane 402 includes a first end 430, opposing second end 432, and an annular groove 434. Referring to FIG. 29, membrane 402 is attachable to first end 410 of connector 400 by a press fit or interference fit. In one embodiment, membrane 402 is attached to connector 400 by pressing membrane 402 within first end 410 of connector 400 such that annular protrusion 414 of connector engages annular groove 434 of membrane 402 to secure membrane 402 to connector 400 as shown in FIG. 29. The assembly of the membrane 402 within a corresponding connector is described in more detail below. The first end 430 of the membrane 402 defines a convex surface, although other suitable shaped surfaces may be utilized. The second end 432 of the membrane 402 defines a cavity 403 that extends toward the first end 430 of the membrane 402. The cavity 403 terminates between the first end 430 and second end 432 of the membrane at about half a length of the membrane 402. The terminal end of the cavity 403 may define a concave surface, although other suitable shaped surfaces may be utilized. The cavity 403 tapers and narrows as it extends toward the first end 430 of the membrane 402. The second end 432 of the membrane 402 includes an annular projection 405 extending away from the second end 432 of the membrane 402.

The pierceable barrier membrane 402 provides for a liquid and gas tight seal between a piercing member of a barrel assembly and the pierceable barrier membrane 402 during fluid transfer of a medication to a patient so to minimize leakage and thereby prevent exposure of hazardous medicaments to a user. Barrier membrane 402 provides a self-sealing seal that, with a barrel assembly attached to connector 400, provides a leak-proof seal preventing any substance being administered to a patient from being exposed to a health care provider administering the medication. In one embodiment, barrier membrane 402 comprises a resilient material. For example, barrier membrane 402 is preferably a unitary device molded of any flexible, elastomeric material conventionally used for fabricating gas-proof closures. Barrier membrane 402 may be formed of a natural rubber material, polyurethane elastomers, butyl rubbers, or similar materials.

Figure 34:
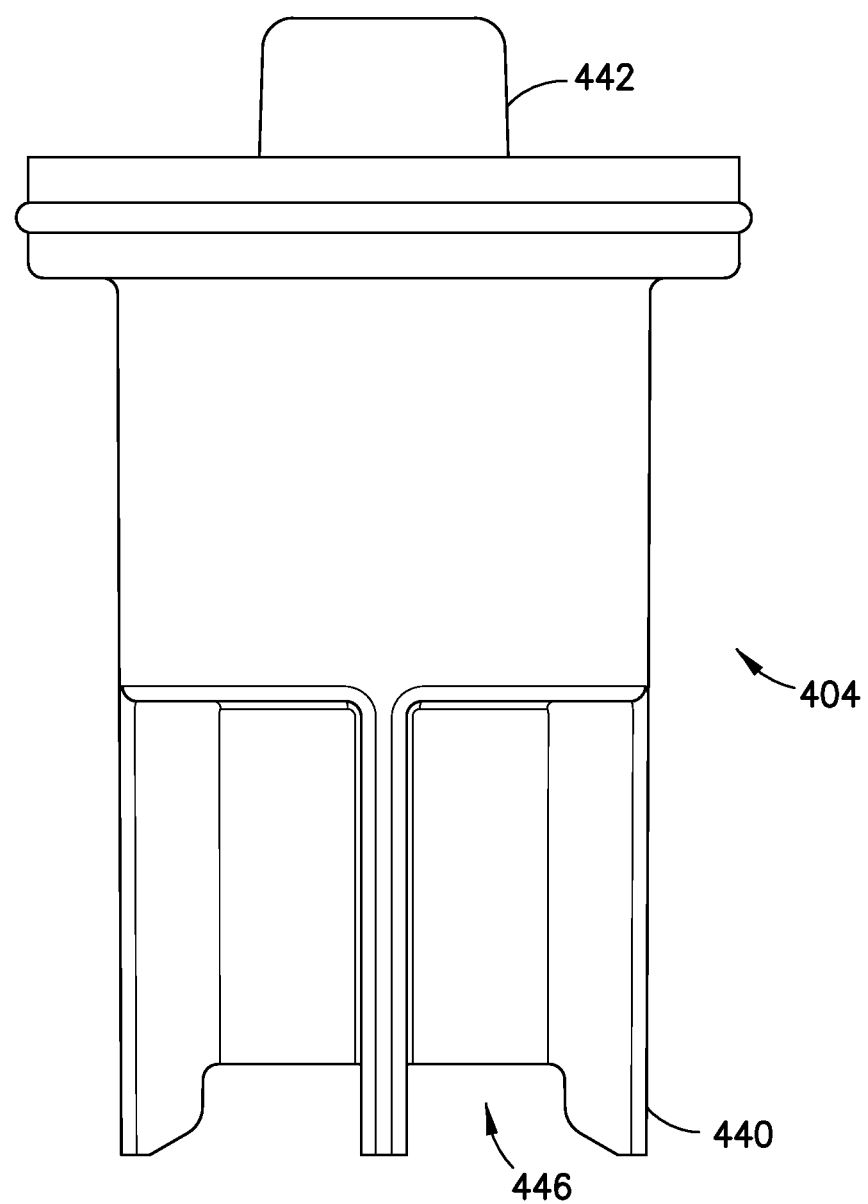
FIG. 34 is a perspective view of a first luer component in accordance with another embodiment of the present invention.
Figure 35:
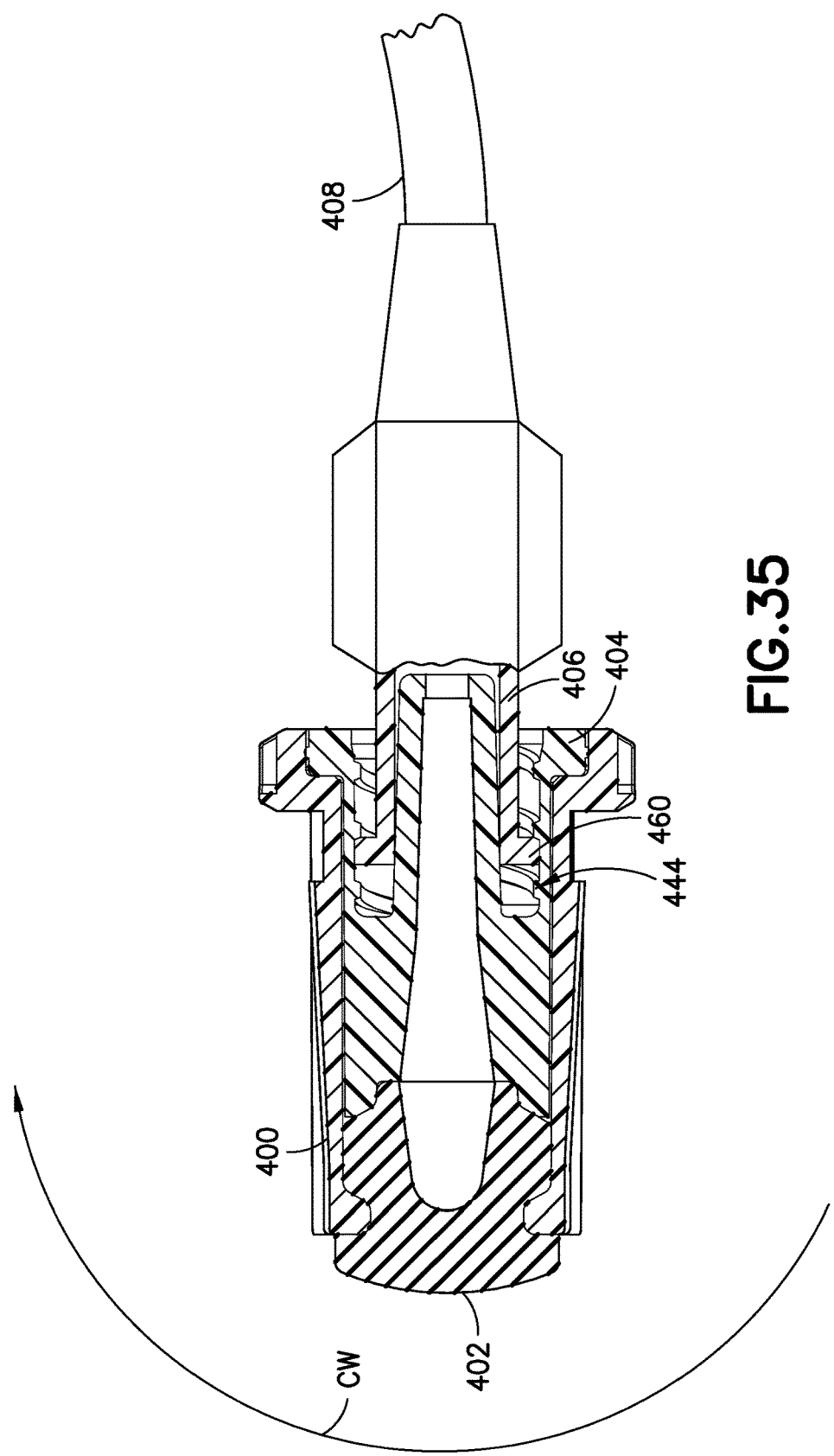
FIG. 35 is a perspective view of a connection system and a first luer component connected to a second luer component and an IV line in accordance with another embodiment of the present invention.

Referring to FIGS. 29 and 34, in one embodiment, system 132A includes a male or first luer component 404. First luer component 404 includes first end 440, opposing second end 442, threaded portion 444, and membrane receiving portion 446. Referring to FIG. 35, a female or second luer component 406 is attached to an end of IV line 408. The threaded portion 444 of first luer component 404 is engageable with a threaded portion 460 (FIG. 35) of second luer component 406 to secure first luer component 404 to second luer component 406 and IV line 408 as shown in FIG. 35. First luer component 404 is rotated in a clockwise direction generally along arrow CW (FIG. 35) relative to second luer component 406 to tighten and secure threaded portion 444 of first luer component 404 to threaded portion 460 of second luer component 406.

Referring to FIG. 29, first luer component 404 is attachable to second end 412 of connector 400 by a press fit or interference fit. In one embodiment, first luer component 404 is attached to connector 400 by pressing first luer component 404 within second end 412 of connector 400 such that second end 432 of membrane 402 engages membrane receiving portion 446 of first luer component 404 to secure first luer component 404, membrane 402, and connector 400 theretogether as shown in FIG. 29.

Referring to FIGS. 28-35, the use of connection system 132A of the present disclosure to connect a first medical device component, e.g., injector adapter 12, to a second medical device component, e.g., connector 400, will now be described. For the sake of brevity, the similar steps of using connection system 132A (FIGS. 28-35) will not all be discussed in conjunction with the embodiment illustrated in FIGS. 28-35. Connection system 132A includes similar steps as discussed in detail above with regards to connection system 132.

Referring to FIG. 35, once it is desired to disconnect an injector from connector 400, the injector can be rotated in a clockwise direction generally along arrow CW to rotate the injector out of engagement with first securement element 140A of connector 400 and to disconnect the injector from connector 400. In this manner, during the disconnecting step, an overall connector 400 tightening to an IV line 408 results during the use of connection system 132A. For example, during the disconnecting step, rotation in a clockwise direction to disconnect the injector from connector 400 also causes the threaded portion 444 of first luer component 404 to tighten to threaded portion 460 of second luer component 406 thereby tightening connector 400 to IV line 408.

Figure 36:
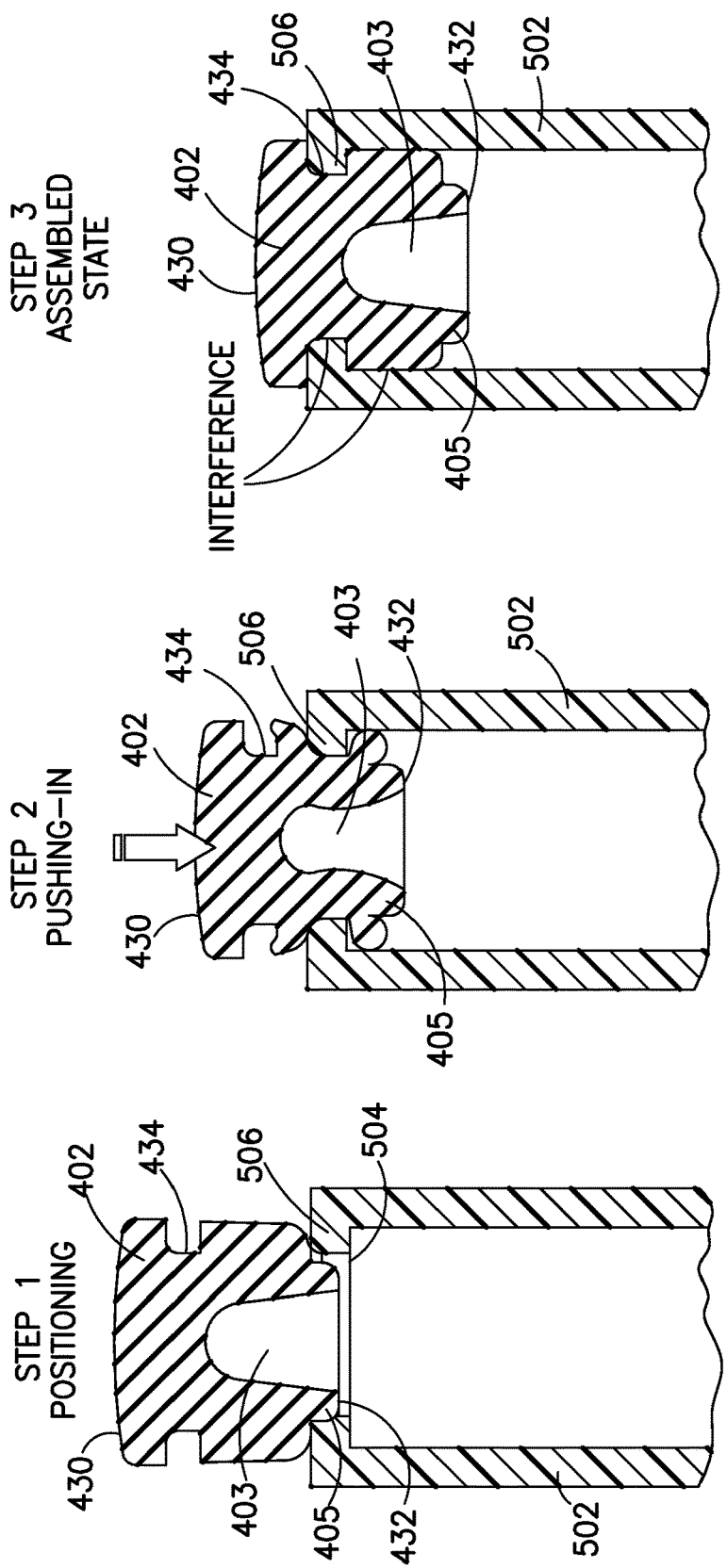
FIG. 36A is a cross-sectional view of a first step in assembling the membrane of FIG. 32 with a connector according to one embodiment of the present invention.
FIG. 36B is a cross-sectional view of a second step in assembling the membrane of FIG. 32 with a connector according to one embodiment of the present invention.
FIG. 36C is a cross-sectional view of a third step in assembling the membrane of FIG. 32 with a connector according to one embodiment of the present invention.

Referring to FIGS. 36A-36C, in one embodiment, the membrane 402 is assembled with a corresponding connector 502 by initial positioning the opposing end 432 of the membrane 402 within a central opening 504 of the connector 502 as shown in FIG. 36A. Referring to FIG. 36B, the membrane 402 is then pushed or forced into the opening 504 and past the annular protrusion 506 of the connector 502. The annular protrusion 506 compresses and engages the membrane 402 as the membrane 402 is inserted into the connector 502. Referring to FIG. 36C, the membrane 402 is pushed into the connector 502 until the annular groove 434 of the membrane 402 is aligned with and receives the annular protrusion 506 of the connector 502 thereby creating an interference fit between the connector 502 and the membrane 402. In particular, the intermediate portion of the membrane 402 between the first end 430 and the opposing end 432 of the membrane has an interference fit with the connector 502, which creates a positive internal pressure to promote self-sealing when pierced with a cannula or engaged with another connector. Further, when the membrane 402 is assembled with the connector 502, the first end 430 of the membrane extends beyond the connector 502 so that when the membrane 402 and connector 502 are mated with a corresponding membrane and connector, the first end 430 of the membrane is not restricted thereby improving the resealing performance of the membrane 402 when pierced by a cannula.

Figure 37:
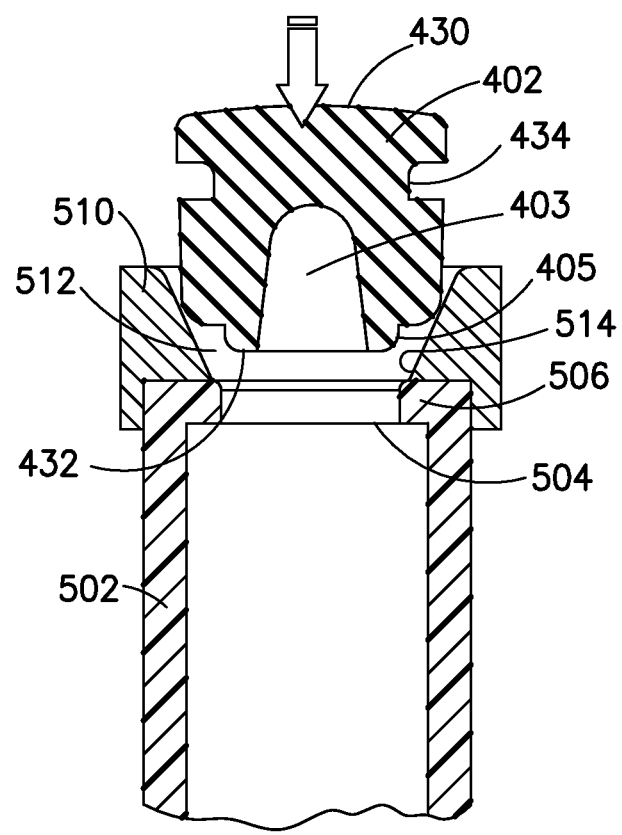
FIG. 37 is a cross-sectional view of a second step in assembling the membrane of FIG. 32 with a connector according to a further embodiment of the present invention.

Referring to FIG. 37, in one embodiment, an assembly tool 510 is provided to assist in the second step of inserting the membrane 402 within the connector 502. The assembly tool 510 includes a central opening 512 and a tapered surface 514, such as a frusto-conical shaped surface. The central opening 512 of the assembly tool 510 is aligned with the opening 504 of the connector 502. After positioning the membrane 402 adjacent to the assembly tool 510, the membrane is then pushed and inserted into the opening 512 of the assembly tool 510 with the membrane 402 engaging the tapered surface 514 of the tool 510 to compress the membrane and allow for easier insertion of the membrane 402 into the connector 502. The membrane 402 is otherwise assembled with the connector 502 in the same manner as described above in connection with FIGS. 36A-36C with the annular groove 434 of the membrane receiving the annular protrusion 506 of the connector 502.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A system comprising:
   a first medical device component having a first end, a second end, and a sidewall extending therebetween, the sidewall having an exterior surface and an interior surface, the interior surface of the sidewall having a first projecting element; and
   a second medical device component having a first connection channel, a first disconnection channel, and a first securement element comprising a recess disposed between the first connection channel and the first disconnection channel, the first connection channel distinct from the first disconnection channel and separated therefrom by a wall,
   wherein with the first projecting element of the first medical device component received within the first connection channel of the second medical device component, the first connection channel guides the first projecting element to the first securement element,
   wherein with the first projecting element engaged with the first securement element, the first medical device component is secured to the second medical device component, and
   wherein with the first projecting element of the first medical device component received within the first disconnection channel of the second medical device component, the first disconnection channel guides the first projecting element from the first disconnection channel thereby disengaging the first medical device component from the second medical device component.

2. The system of claim 1, wherein the first medical device component is an injector adapter and the second medical device component is a vial adapter.

3. The system of claim 1, wherein the first medical device component is an injector adapter and the second medical device component is an IV line adapter.

4. The system of claim 1, wherein the interior surface of the sidewall of the first medical device component includes a second projecting element spaced from the first projecting element.

5. The system of claim 4, wherein the second medical device component further includes a second connection channel, a second disconnection channel, and a second securement element disposed between the second connection channel and the second disconnection channel, the second connection channel distinct from the second disconnection channel.

6. The system of claim 5, wherein with the second projecting element of the first medical device component received within the second connection channel of the second medical device component, the second connection channel guides the second projecting element to the second securement element,
   wherein with the second projecting element engaged with the second securement element, the first medical device component is secured to the second medical device component, and
   wherein with the second projecting element of the first medical device component received within the second disconnection channel of the second medical device component, the second disconnection channel guides the second projecting element out from the second disconnection channel thereby disengaging the first medical device component from the second medical device component.

7. The system of claim 6, wherein the second medical device component further includes a first step member disposed between the first securement element and the first disconnection channel and a second step member disposed between the second securement element and the second disconnection channel.

8. The system of claim 7, wherein with the first projecting element engaged with the first securement element, rotation of the first medical device component in a counter-clockwise direction relative to the second medical device component disengages the first projection element from the first securement element and moves the first projection element over the first step member and into the first disconnection channel.

9. The system of claim 7, wherein with the second projecting element engaged with the second securement element, rotation of the first medical device component in a counter-clockwise direction relative to the second medical device component disengages the second projection element from the second securement element and moves the second projection element over the second step member and into the second disconnection channel.

10. The system of claim 7, wherein with the first projecting element engaged with the first securement element, rotation of the first medical device component in a clockwise direction relative to the second medical device component disengages the first projection element from the first securement element and moves the first projection element over the first step member and into the first disconnection channel.

11. The system of claim 7, wherein with the second projecting element engaged with the second securement element, rotation of the first medical device component in a clockwise direction relative to the second medical device component disengages the second projection element from the second securement element and moves the second projection element over the second step member and into the second disconnection channel.

12. The system of claim 1, wherein the first projecting element comprises an elastically deformable tab.

13. A system comprising:
an injector adapter enclosing a cannula, the injector adapter having a first end, a second end, and a sidewall extending therebetween, the sidewall having an exterior surface and an interior surface, the interior surface of the sidewall having a first projecting element; and
a vial adapter attachable to a vial, the vial adapter having a vial seal, a first connection channel, a first disconnection channel, and a first securement element comprising a recess and disposed between the first connection channel and the first disconnection channel, the first connection channel distinct from the first disconnection channel and separated therefrom by a wall,
wherein with the first projecting element of the injector adapter received within the first connection channel of the vial adapter, the first connection channel guides the first projecting element to the first securement element,
wherein with the first projecting element engaged with the first securement element, the injector adapter is secured to the vial adapter, and
wherein with the first projecting element of the injector adapter received within the first disconnection channel of the vial adapter, the first disconnection channel guides the first projecting element out from the first disconnection channel thereby disengaging the injector adapter from the vial adapter.

14. The system of claim 13, wherein the interior surface of the sidewall of the injector adapter includes a second projecting element spaced from the first projecting element.

15. The system of claim 14, wherein the vial adapter further includes a second connection channel, a second disconnection channel, and a second securement element disposed between the second connection channel and the second disconnection channel, the second connection channel distinct from the second disconnection channel.

16. The system of claim 15, wherein with the second projecting element of the injector adapter received within the second connection channel of the vial adapter, the second connection channel guides the second projecting element to the second securement element,
wherein with the second projecting element engaged with the second securement element, the injector adapter is secured to the vial adapter, and
wherein with the second projecting element of the injector adapter received within the second disconnection channel of the vial adapter, the second disconnection channel guides the second projecting element out from the second disconnection channel thereby disengaging the injector adapter from the vial adapter.

17. The system of claim 15, wherein the second securement element comprises a recess.

18. The system of claim 16, wherein the vial adapter further includes a first step member disposed between the first securement element and the first disconnection channel and a second step member disposed between the second securement element and the second disconnection channel.

19. The system of claim 18, wherein with the first projecting element engaged with the first securement element, rotation of the injector adapter in a counter-clockwise direction relative to the vial adapter disengages the first projection element from the first securement element and moves the first projection element over the first step member and into the first disconnection channel.

20. The system of claim 18, wherein with the second projecting element engaged with the second securement element, rotation of the injector adapter in a counter-clockwise direction relative to the vial adapter disengages the second projection element from the second securement element and moves the second projection element over the second step member and into the second disconnection channel.

21. The system of claim 18, wherein with the first projecting element engaged with the first securement element, rotation of the injector adapter in a clockwise direction relative to the vial adapter disengages the first projection element from the first securement element and moves the first projection element over the first step member and into the first disconnection channel.

22. The system of claim 18, wherein with the second projecting element engaged with the second securement element, rotation of the injector adapter in a clockwise direction relative to the vial adapter disengages the second projection element from the second securement element and moves the second projection element over the second step member and into the second disconnection channel.

23. The system of claim 14, wherein the second projecting element comprises an elastically deformable tab.

24. The system of claim 13, wherein the first projecting element comprises an elastically deformable tab.

* * * * *